(12) United States Patent
Raju

(10) Patent No.: US 6,261,818 B1
(45) Date of Patent: Jul. 17, 2001

(54) CARK PROTEIN AND NUCLEIC ACID MOLECULES AND USES THEREFOR

(75) Inventor: Jeyaseelan Raju, Acton, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/291,839

(22) Filed: Apr. 14, 1999

Related U.S. Application Data

(60) Provisional application No. 60/111,938, filed on Dec. 11, 1998.

(51) Int. Cl.$^7$ ............................. C12P 21/06; C12N 9/00; C12N 9/12; C12N 1/20; C12N 15/00
(52) U.S. Cl. ............................. 435/194; 435/6; 435/15; 435/69.1; 435/252.3; 435/320.1; 435/325; 536/23.1; 536/23.2
(58) Field of Search ................................ 435/6, 15, 69.1, 435/183, 194, 252.3, 320.1, 325; 536/23.1, 23.2

(56) References Cited

PUBLICATIONS

Hsu, S–C. et al. "Modulation of transcriptional regulation by LEF–1 in response to Wnt–1 signaling and association with beta–catenin," *Mol. Cell. Biol.*, 18(8): 4807–4818 (1998).
Hubbard,S.R., et al. "Crystal structure of the tyrosine kinase domain of the human insulin receptor," *Nature*, 372 (6508): 746–753 (1994).
Hwang,D.M., et al. "Analysis of expressed sequence tags from a fetal human heart cDNA library," *Genomics*, 30 (2): 293–298 (1995).
Irie,K., et al. "A new protein kinase, SSP31, modulating the SMP3 gene–product involved in plasmid maintenance in *Saccharomyces cerevisiae*," *Gene*, 108 (1): 139–144 (1991).
Jeyaseelan, R et al. "A novel cardiac–restricted target for doxorubicin: Carp, a nuclear modulator of gene expression in cardiac progenitor cells and cardiomyocytes," *J. Biol. Chem.*, 272(5):22800–22808 (1997).
Johnston,M., et al. "Complete nucleotide sequence of *Saccharomyces cerevisiae* chromosome VIII," *Science*, 265 (5181): 2077–2082 (1994).
Katoh,M., et al. "Cloning and characterization of MST, a novel (putative) serine/threonine kinase with SH3 domain," *Oncogene*, 10 (7): 1447–1451 (1995).
Laidlaw,S.M., et al. "Fowlpox virus encodes nonessential homologs of cellular alpha–SNAP, PC–1, and an orphan human homolog of a secreted nematode protein," *J. Virol.*, 72 (8): 6742–6751 (1998).
Lambert,S., et al. "cDNA sequence for human erythrocyte ankyrin," *Proc. Natl. Acad. Sci. U.S.A.*, 87 (5): 1730–1734 (1990).
Lee,K.S. et al. "Dominant mutations in a gene encoding a putative protein kinase (BCK1) bypass the requirement for a *Saccharomyces cerevisiae* protein kinase C homolog," *Mol. Cell. Biol.*, 12 (1): 172–182 (1992).

Lisziewicz,J., et al. "Isolation and nucleotide sequence of a *Saccharomyces cerevisiae* protein kinase gene suppressing the cell cycle start mutation cdc25," *J. Biol. Chem.*, 262 (6): 2549–2553 (1987).
Lux,S.E., et al. "Analysis of cDNA for human erythrocyte ankyrin indicates a repeated structure with homology to tissue–differentiation and cell–cycle control proteins," *Nature*, 344 (6261): 36–42 (1990).
Miosga,T., et al. "Sequence and function analysis of a 9.74 kb fragment of *Saccharomyces cerevisiae* chromosome X including the BCK1 gene," *Yeast*, 10 (11): 1481–1488 (1994).
Mohammadi,M., et al. "Structure of the FGF receptor tyrosine kinase domain reveals a novel autoinhibitory mechanism," *Cell*, 86 (4): 577–587 (1996).
Novak, A. et al. "Cell adhesion and the integrin–linked kinase regulate the LEF–1 and beta–catenin signaling pathways," *PNAS USA*, 95: 4374–4379 (1998).
Otsuka,A.J., et al. "An ankyrin–related gene (unc–44) is necessary for the proper axonal guidance in *Caenorhabditis elegans*," *J. Cell Biol.*, 129 (4): 1081–1092 (1995).
Otto,E., et al. "Isolation and characterization of cDNAs encoding human brain ankyrins reveal a family of alternatively spliced genes," *J. Cell Biol.*, 114 (2): 241–253 (1991).
Percival–Smith,A. et al. "Characterization and mutational analysis of a cluster of three genes expressed preferentially during sporulation of *Saccharomyces cerevisiae*," *Mol. Cell. Biol.*, 6 (7): 2443–2451 (1986).
Radeva, G. et al. "Overexpression of the integrin–linked kinase promotes anchorage–independent cell cycle progression," *J. Biol. Chem.*, 272(21): 13937–13944 (1997).
Rhodes,N., et al. "STE11 is a protein kinase required for cell–type–specific transcription and signal transduction in yeast," *Genes Dev.*, 4 (11): 1862–1874 (1990).
Russo,A.A., et al. "Structural basis of cyclin–dependent kinase activation by phosphorylation," *Nat. Struct. Biol.*, 3 (8): 696–700 (1996).
Saito, H. et al. "Regulation of a novel gene encoding a lysyl oxidase–related protein in cellular adhesion and senescence," *J. Biol. Chem.*, 272(13):8157–8160 (1997).

(List continued on next page.)

*Primary Examiner*—Ponnathapu Achutamurthy
*Assistant Examiner*—Manjunath N. Rao
(74) *Attorney, Agent, or Firm*—Lahive & Cockfield, LLP; Amy E. Mandragouras; Maria C. Laccotripe

(57) ABSTRACT

The invention provides isolated nucleic acids molecules, designated CARK nucleic acid molecules. The invention also provides antisense nucleic acid molecules, recombinant expression vectors containing CARK nucleic acid molecules, host cells into which the expression vectors have been introduced, and nonhuman transgenic animals in which a CARK gene has been introduced or disrupted. The invention still further provides isolated CARK proteins, fusion proteins, antigenic peptides and anti-CARK antibodies. Diagnostic methods utilizing compositions of the invention are also provided.

110 Claims, 17 Drawing Sheets

OTHER PUBLICATIONS

Sivasubramanian, N. et al., Cardiac myotrophin exhibits rel/NF–kB interacting activity in vitro,*J. Biol. Chem.,* 271(5): 2812–2816 (1996).

Somers, S.S. et al. "Comparison of transforming growth factor beta and a human tumour–derived suppressor factor," *Cancer Immunology Immunotherapy,* 33:217–22 (1991).

Tan,J.L. et al. "Developmentally regulated protein–tyrosine kinase genes in *Dictyostelium discoideum,*" *Mol. Cell. Biol.,* 10: 3578–3583 (1990).

Tanaka,T., et al. "Construction of a Normalized Directionally Cloned cDNA Library from Adult Heart and Analysis of 3040 Clones by Partial Sequencing," *Genomics,* 35: 231–235 (1996).

Tse,W.T., et al. Isolation and chromosomal localization of a novel nonerythroid ankyrin gene, *Genomics,* 10 (4): 858–866 (1991).

Toda, T., et al. "Three different genes in *S. cerevisiae* encode the catalytic subunits of the cAMP–dependent protein kinase," *Cell,* 50: 277–287 (1987).

Jeffrey, P.D. et al. "Mechanism of CDK activation revealed by the structure of a cyclinA–CDK2 complex," *Nature,* 376:313–320 (1995).

Vandenbol,M., et al. "Sequencing and analysis of a 20.5 kb DNA segment located at the left arm of yeast chromosome XI," *Yeast,* 10 Suppl A: S25–S33 (1994).

Xu, W., et al. "Three dimensional structure of the tyrosine kinase c–Src," *Nature,* 385 (6617): 595–602 (1997).

White,R.A., et al. "Murine erythrocyte ankyrin cDNA: highly conserved regions of the regulatory domain," *Mamm. Genome,*3 (5): 281–285 (1992).

Wilson,R., et al. "2.2 Mb of contiguous nucleotide sequence from Chromosome III of *C. elegans,*" *Nature,* 368 (6466): 32–38 (1994).

Wu,L.C., et al. "Identification of a RING protein that can interact in vivo with the BRCA1 gene product," *Nature Genet.,* 14 (4): 430–440 (1996).

Wu,C., et al. "Integrin–linked protein kinase regulates fibronectin matrix assembly, E–cadherin expression, and tumorigenicity," *J. Biol. Chem.,* 273(1): 528–536 (1998).

Zou, Y. et al. "CARP, a cardiac ankyrin repeat protein, is downstream in the Nkx2–5 homeobox gene pathway," *Development,* 124(4): 793–804 (1997).

Copy of Blast® search (EST database) using the CARP2 nucleic acid sequence.

Copy of Blast® search (NRN database) using the CARP2 nucleic acid sequence.

Copy of Blast® search (NRP database) using the CARP2 amino acid sequence.

Copy of Blast® search (Patent–2 database) using the CARP2 amino acid sequence.

Copy of Blast® search (PDB database) using the CARP2 amino acid sequence.

Copy of Blast® search (PDB database) using the CARP2 kinase domain amino acid sequence.

Copy of Blast® search (Patent–2 database) using the CARP2 kinase domain amino acid sequence.

Copy of Blast® search (Yeast database) using the CARP2 amino acid sequence.

Copy of Blast® search (Yeast database) using the CARP2 kinase domain amino acid sequence.

Copy of Blast® search (NRP database) using the CARP2–prot amino acid sequence.

Copy of Blast® search (NRP database) using the CARP2 kinase domain amino acid sequence.

GenBank Accession No. 1942427, Chain A, Cyclin A—Cyclin–Dependent Kinase 2 Complex.

GenBank Accession No. 1942625, Chain A, Phosphorylated Cyclin–Dependent Kinase–2 Bound To Cyclin A.

GenBank Accession No. 2194103, Chain A, Src Family Kinase Hck–Amp–Pnp Complex.

GenBank Accession No. 2392334; chain A, crystal structure of the tyrosine–protein kinase domain of fibroblast growth factor receptor 1.

GenBank Accession No. OKBYC1; Protein Kinase (EC 2.7.1.37), Camp–dependent, catalytic chain 1–yeast.

GenBank Accession No. 2392337 for crystal structure of human tyrosine–protein kinase c–src.

GenBank Accession No. 999510 for insulin receptor (tyrosine kinase domain) mutant with cys 981 replaced by ser and tyr 984 replaced by phe.

GenBank Accession No. A35670; Protein–tyrosine kinase (EC 2.7.1.112) 1–slime mold (dictyostelium discoideum).

GenBank Accession Number AA758546; ah70b01.s1 Soares_testis_NHT *Homo sapiens* cDNA clone 1320937 3', mRNA sequence.

GenBank Accession No. AA389675, M186 Fetal heart, Lambda ZAP Express *Homo sapiens* cDNA 5'.

GenBank Accession No. AA938871; OP74ALL.S1 Soares_NFL_T_GBC_S1 *Homo Sapiens* cDNA clone image: 1582556 3'.

GenBank Accession No. 2781357; F2401.13.

GenBank Accession No. AF024491; *Caenorhabditis elegans* cosmid C24A1.

GenBank Accession No. AF068261; *Ratus norvegicus* pancreatic serine threonine kinase mRNA.

GenBank Accession No. AI040439; ow16c03.x1 Soares_parathyroid_tumor_NbHPA *Homo Sapiens* cDNA clone image: 1646980 3' similar to WP:C24A1.3 CE08335.

GenBank Accession No. AI289394; qw21h08.x1 NCI_CGAP_Ut4 *Homo sapiens* cDNA clone image:1991775 3'.

GenBank Accession No. AI333762; qp98h10.x1 Soares_fetal_lung_NbHL19W *Homo Sapiens* cDNA clone image: 1931107 3' similar to WP:C24A1.3 CE08335.

GenBank Accession No. AI375137; tc09g12.x1 Soares_NhHMPu_S1 *Homo Sapiens* cDNA clone image: 2063398 3' similar to WP:C24A1.3 CE08335.

GenBank Accession No. AI377988; te61c04.x1 Soares_NFL_T_GBC_S1 *Homo Sapiens Sapiens* cDNA clone image: 2091174 3'.

GenBank Accession No. AJ006408; Fowlpox virus strain ank2, ank3, snap, cel1/dnaseII and pc1 genes.

GenBank Accession No. CAA20048; Putative protein.

GenBank Accession No. AQ242835; HS_2061_A1_G12_T7 CIT Approved Human Genomic Sperm Library D *Homo sapiens* genomic clone Plate=2061 Col=23 Row=M.

GenBank Accession No. B35049; Ankyrin 1, erythrocyte form 3—human.

GenBank Accession No. C03950; Human heart cDNA (YNakamura) *Homo Sapiens* cDNA clone 3NHC2459.

GenBank Accession No. D10389; Yeast DNA for Ssp31 protein kinase.

GenBank Accession No. M17074; Yeast (*S. cerevisiae*) cAMP–dependent kinase subunit (TPK3) gene.

GenBank Accession No. M33784; *D.discoideum* protein–tyrosine kinase–2 (DPYK2) mRNA.

GenBank Accession No. M33785; *D.discoideum* protein–tyrosine kinase–1 (DPYK1) mRNA.
GenBank Accession No. M67449; Glycine max protein kinase (PK6) mRNA, complete cds.
GenBank Accession No. P05986; Camp dependent protein kinase type 3 (PKA3).
GenBank Accession No. P06244; Camp–dependent protein kinase type 1 (PKA 1) (CDC25 suppressing protein kinase) (PK–25).
GenBank Accession No. P08458; Sporulation–specific protein 1.
GenBank Accession No. P16157; Ankyrin R (Ankyrins 2.1 and 2.2) (Erythrocyte ankyrin).
GenBank Accession No. P18160; Non–receptor tyrosine kinase spore lysis A (Tyrosine–protein kinase 1).
GenBank Accession No. P23561; Serine/Threonine–protein kinase STE11.
GenBank Accession No. P38692; Serine/Threonine–protein kinase NRK1 (N–rich kinase 1).
GenBank Accession No. Q01389; Serine/Threonine protein kinase BCK1/SLK1/SSP31.
GenBank Accession No. Q01485; Ankyrin, brain variant 2 (Ankyrin B) (Ankyrin, Nonery throid).
GenBank Accession No. Q02357; Ankyrin.
GenBank Accession No. X16609; Human mRNA for ankyrin (variant 2.1).
GenBank Accession No. X56958; *Homo Sapiens* mRNA for ankyrin, Brank–2 protein.
GenBank Accession No. X60227; *S.Cerevisiae* BCK1 gene for protein kinase.
GenBank Accession No. Z48615; *H.sapiens* MST mRNA for serine/threonine kinase.
GenBank Accession No. R57737; F5349 fetal heart *Homo Sapiens* cDNA clone F5349 5' end.
GenBank Accession No. Z97337; *Arabidopsis thaliana* DNA chromosome 4, ESSA 1 contig fragment No. 2.
GenBank Accession No. Z98551; *Plasmodium falciparum* MAL3P6.
GenBank Accession No. S51380; Protein kinase STE11 (EC 2.7.1.–)—yeast.
GenBank Accession No. U01064; *Dictyostelium discoideum* AX2 protein tyrosine kinase mRNA.
GenBank Accession No. U21734; *Caenorhabditis Elegans* ankyrin–related protein UNC–44 (unc–44).
GenBank Accession No. U39847; *Caenorhabditis Elegans* AO13 ankyrin, AO66 ankyrin and AO49 ankyrin (unc–44) gene, three alternatively spliced forms.
GenBank Accession No. U50071; *Caenorhabditis Elegans* cosmid B0350.
GenBank Accession No. U65916; *Rattus Norvegicus* ankyrin mRNA, membrane binding domain.

GenBank Accession No. U76638; Human BRCA1–associated RING domain protein (BARD1) mRNA.
Baumeister, A. et al. "Accumulation of muscle Ankyrin repeat protein transcript reveals local activation of primary myotube end compartments during muscle morphogenesis," *J. Cell. Biol*, 139(5): 1231–1242 (1997).
Bevan, M. et al. "Analysis of 1.9 Mb of contiguous sequence from chromosome 4 of Arabidopsis thaliana," *Nature*,391 (6666):485–488 (1998).
Cairns,B. R., et al. "Order of action of components in the yeast pheromone response pathway revealed with a dominant allele of the STE1 1 kinase and the multiple phosphorylation of the STE7 kinase," *Genes Dev.*, 6(7):1305–1318 (1992);.
Cannon, J. F. et al. "Characterization of Saccharomyces cerevisiae genes encoding subunits of cyclic AMP–dependent protein kinase," *Mol. Cell. Biol.*, 7(8):2653–2663 (1987);.
Sicheri. F. et al. "Crystal structure of the Src family tyrosine kinase Hck," *Nature*, 385:602–609 (1997);.
Costigan,C., et al. "A synthetic lethal screen identifies SLK1, a novel protein kinase homolog implicated in yeast cell morphogenesis and cell growth," *Mol. Cell. Biol.* 12, (3):1162–1178 (1992);.
Delcommenne, M. et al. "Phosphoinositide–3–OH kinase–dependent regulation of glycogen synthase kinase 3 and protein kinase B/AKT by the intergrin–linked kinase," *PNAS USA*95:11211–11216 (1998);.
Eber, S. W. et al. "Ankyrin–1 mutations are a major cause of dominant and recessive hereditary spherocytosis," *Nat. Genet.*, 13(2):214–218 (1985);.
Ebina, Y., et al. "The human insulin receptor cDNA: the structural basis for hormon–activated transmembrane signalling," *Cell*, 40 (4):747–758 (1985);.
Fearon,K. et al. "Structure and function of MRP20 and MRP49, the nuclear genes for two proteins of the 54 S subunit of the yeast mitochondrial ribosome," *J. Biol. Chem.*, 267(8): 5162–5170 (1992);.
Feng,X.–H., et al. "Cloning and characterization of a novel member of protein kinase family from soybean," *Biochim. Biophys. Acta.*, 1172: 200–204 (1993);.
Gallagher, P.G. et al. "An alternate promoter directs expression of a truncated, muscle–specific isoform of the human ankyrin 1 gene," *J. Biol. Chem.*, 273(3):1339–1348 (1998);.
Goto, K. et al. "A 104–kDa diacyglycerol kinase containing ankyrin–like repeats localizes in the cell nucleus," *PNAS USA*, 93: 11196–11201 (1996);.

Nucleic Acid Sequence

```
GTCGACCCACGCGTCCGGCCCTGGAGAAAGGAAGAAACTTATAATAAATG
GGAAATTATAAATCTAGACCAACCCAAACTTGTACTGATGAATGGAAGAA
AAAAGTCAGTGAATCATATGTTATCACAATAGAAAGATTAGAAGATGACC
TGCAGATCAAGGAAAAGAACTGACAGAACTAAGGAATATATTTGGCTCT
GATGAAGCCTTCAGTAAAGTCAATTTAAATTACCGCACTGAAAATGGGCT
GTCTCTACTTCATTTATGTTGCATTTGTGGAGGCAAGAAATCACATATTC
GAACTCTTATGTTGAAAGGGCTCCGCCCATCTCGACTGACAAGAAATGGA
TTTACAGCCTTGCATTTAGCAGTTTACAAGGATAATGCAGAATTGATCAC
TTCTCTGCTTCACAGTGGAGCTGATATACAGCAGGTTGGATACGGTGGCC
TCACTGCCCTCCATATTGCTACAATAGCTGGCCACCTAGAGGCTGCTGAT
GTGCTGTTGCAACATGGAGCTAATGTCAATATTCAAGATGCAGTTTTTTT
CACTCCATTGCATATTGCAGCGTACTATGGACATGAACAGGTAACTCGCC
TTCTTTTGAAATTTGGTGCTGATGTAAATGTAAGTGGTGAAGTTGGAGAT
AGACCCCTCCACCTAGCATCTGCAAAAGGATTCTTGAATATTGCAAAACT
CTTGATGGAAGAAGGCAGCAAAGCAGATGTGAATGCTCAAGATAATGAAG
ACCATGTCCCACTCCATTTCTGTTCTCGATTTGGACACCATGATATAGTT
AAGTATCTGCTGCAAAGTGATTTGGAAGTTCAACCTCATGTTGTTAATAT
CTATGGAGATACCCCCTTACACCTGGCATGCTACAATGGCAAATTTGAAG
TTGCCAAGGAAATCATCCAAATATCAGGAACAGAAAGTCTGACTAAGGAA
AACATCTTCAGTGAAACAGCTTTTCATAGTGCTTGTACCTATGGCAAGAG
CATTGACCTAGTCAAATTTCTTCTTGATCAGAATGTCATAAACATCAACC
ACCAAGGAAGGGATGGGCACACTGGATTACACTCTGCTTGCTACCACGGT
CACATTCGCCTGGTTCAGTTCTTACTGGATAATGGAGCTGATATGAATCT
AGTGGCTTGTGATCCCAGCAGGTCTAGTGGTGAAAAGATGAGCAGACAT
GTTTGATGTGGGCTTATGAAAAGGGCATGATGCCATTGTCACACTCCTG
AAGCATTATAAGAGACCACAAGATGAATTGCCCTGTAATGAATATTCTCA
GCCTGGAGGAGATGGCTCCTATGTGTCTGTTCCATCACCCTTGGGGAAGA
TTAAAAGCATGACAAAAGAGAAGGCAGATATTCTCCTCCTAAGAGCTGGA
TTGCCTTCACATTTCCATCTTCAGCTCTCAGAAATTGAGTTCCATGAGAT
TATTGGCTCAGGTTCTTTTGGGAAAGTATATAAAGGACGATGCAGAAATA
AAATAGTGGCTATAAAACGTTATCGAGCCAATACCTACTGCTCCAAGTCA
GATGTGGATATGTTTTGCCGAGAGGTGTCCATTCTCTGCCAGCTCAATCA
TCCCTGCGTAATTCAGTTTGTGGGTGCTTGCTTGAATGATCCCAGCCAGT
TTGCCATTGTCACTCAATACATATCAGGGGGTTCTCTGTTCTCCCTCCTT
CATGAGCAGAAGAGGATTCTTGATTTGCAGTCTAAATTAATTATTGCAGT
AGATGTTGCCAAAGGCATGGAGTACCTTCACAACCTGACACAGCCAATTA
TACATCGTGACTTGAACAGTCACAATATTCTTCTCTATGAGGATGGGCAT
GCTGTGGTGGCAGATTTTGGAGAATCAAGATTTCTACAGTCTCTGGATGA
AGACAACATGACAAAACAACCTGGGAACCTCCGTTGGATGGCTCCTGAGG
TGTTCACGCAGTGCACTCGGTACACCATCAAAGCAGATGTCTTCAGCTAT
GCTCTGTGTCTGTGGGAATTCTCACTGGCGAAATTCCATTCGCTCATCT
CAAGCCAGCGGCTGCGGCAGCAGACATGGCTTACCACCACATCAGACCTC
CCATTGGCTATTCCATTCCCAAGCCCATATCATCTCTGCTGATACGAGGG
TGGAACGCATGTCCTGAAGGAAGACCCGAATTTTCTGAAGTTGTCATGAA
GTTAGAAGAGTGTCTCTGCAACATTGAGCTGATGTCTCCTGCATCAAGTA
ACAGCAGTGGGTCTCTCTCACCTTCTTCTTCTTCTGATTGCCTGGTGAAC
CGGGGAGGACCTGGCCGGAGTCATGTGGCAGCATTAAGAAGTCGTTTCGA
ATTGGAATATGCTCTAAATGCAAGGTCCTATGCTGCTTTGTCCCAAAGTG
CTGGACAATATTCCTCTCAAGGTCTGTCTTTGGAGGAGATGAAAGAAGT
CTTCAATACACACCCATTGACAAATATGGCTATGTATCCGATCCCATGAG
CTCAATGCATTTTCATTCTTGCCGAAATAGTAGCAGCTTTGAGGACAGCA
GCTGACAGCATTCGGCGTATACCTAAGGAGAGTTTTTTCCCCGAACTGAC
AGCAACGATTCCAACCACGGCAAGCTGGCTTCCAACTATAACATTTTACT
CTCAAAGGTCTCCTTAAATTGGGCTTGTTTTTACTTGTCCTATTTAATTC
```

Fig. 1

```
CCCACTATTAGCAGGCTTTGGATTTGTGCCTAAGGAATAATATGCAAAAG
AACCAAGACAGAATGTATATGAAGAATTGTTTTTAATTTTGTAAATTAAA
AAAAAATTTAGATCGTTACTTGGAAATGGAGCCTAAGTCTGTGGTGGACA
GATAATAATTATGTTTTCCTGGGCTGAATTATGTAGACTTGTGTTTGACA
GCTATGGGTTTATTTCTTAGAACATTGTTCATTTTCTTTTCTCATTATGT
TACTTCTAGTGTTCACCTCTGTGATTAAAGATTCTTTGGTGAAATAGAAA
AAAAAAAAAAAAAAAGGGCGGCCGC
```

Amnino Acid Sequence

```
MGNYKSRPTQTCTDEWKKKVSESYVITIERLEDDLQIKEKELTELRNIFGSDEAFSKVNL
NYRTENGLSLLHLCCICGGKKSHIRTLMLKGLRPSRLTRNGFTALHLAVYKDNAELITSL
LHSGADIQQVGYGGLTALHIATIAGHLEAADVLLQHGANVNIQDAVFFTPLHIAAYYGHE
QVTRLLLKFGADVNVSGEVGDRPLHLASAKGFLNIAKLLMEEGSKADVNAQDNEDHVPLH
FCSRFGHHDIVKYLLQSDLEVQPHVVNIYGDTPLHLACYNGKFEVAKEIIQISGTESLTK
ENIFSETAFHSACTYGKSIDLVKFLLDQNVININHQGRDGHTGLHSACYHGHIRLVQFLL
DNGADMNLVACDPSRSSGEKDEQTCLMWAYEKGHDAIVTLLKHYKRPQDELPCNEYSQPG
GDGSYVSVPSPLGKIKSMTKEKADILLLRAGLPSHFHLQLSEIEFHEIIGSGSFGKVYKG
RCRNKIVAIKRYRANTYCSKSDVDMFCREVSILCQLNHPCVIQFVGACLNDPSQFAIVTQ
YISGGSLFSLLHEQKRILDLQSKLIIAVDVAKGMEYLHNLTQPIIHRDLNSHNILLYEDG
HAVVADFGESRFLQSLDEDNMTKQPGNLRWMAPEVFTQCTRYTIKADVFSYALCLWEILT
GEIPFAHLKPAAAAADMAYHHIRPPIGYSIPKPISSLLIRGWNACPEGRPEFSEVVMKLE
ECLCNIELMSPASSNSSGSLSPSSSSDCLVNRGGPGRSHVAALRSRFELEYALNARSYAA
LSQSAGQYSSQGLSLEEMKRSLQYTPIDKYGYVSDPMSSMHFHSCRNSSSFEDS
```

Fig. 1 cont.

```
           M E E I - - - - - - - - - E W - K T - S - - - - - - - -   Majority
                        |                   |                   |
                       10                  20                  30
                        |                   |                   |
 1   M G N Y K S R P T Q T C T D E W K K V S E S Y V I T I E R       CARP2/prot
 1   M E K K - - - - - - - - S E E - - - - - - - - - - - - - - -    A.thaliana kinase2
 1   M S G - - - - - - - - - - - - - - - - - - - - - - - - L C - -  A.thaliana3
 1   M S C S S S S G S E G E E E G F D A - - - - - - - - - - - -    Arabidopsis thaliana
 1   M R T F - - - - - - - - S D E L K K I S E G Y S V V R S R       c.elegans kinase
 1   - - - - - - - - - - - - - - - - - - - - - - - - - - - - -      D.discoideum (A35670)
 1   G T E T - - - - - - - - T - - - - R M E E D - Q I S C - S       D.Discoideum (U01064)
 1   M E E E E G - - - - A V A K E W G T T P A G P V W T A V F D     H.sapiens (Z48615)
 1   M E E E E G - - - - A V A K E W G T T P A G P V W T A V F D     Homo sapiens (Z48615)
 1   M E H I Q G - - - - - - - - A W - K T I S N G F - - - - - -     Human raf1 (W13107)
 1   M E H I Q G - - - - - - - - A W - K T I S N G F - - - - - -     Human Raf1kinase (R98215)
 1   M G E D - - - - - - - - G N S W I R R T N F S - H T V C H R     Soybean kinase (M67449)

- - - - - - - - - - L - - - - - - - - - - - - - - - -   Majority
                        |                   |                   |
                       40                  50                  60
                        |                   |                   |
31   L E D D L Q I K - - - - - - - - - - - - E K E L T E L R N       CARP2/prot
 8   - - - - - - - - - - - - - - - - - - - - - - - - - - - - -      A.thaliana kinase2
 6   F N - - - - - P F R L - - - - - - - - - - - - - - - - - - -    A.thaliana3
19   - - - - - - - - - - Y R K G G Y H A V R I G D P F S G G R Y     Arabidopsis thaliana
23   L S D D V R S R S N L G W V D V Q I A A F E K S L E D F K Q     c.elegans kinase
 1   - - - - - - - - - - - - - - - - - - - - - - - - - - - - -      D.discoideum (A35670)
16   I D - - - - - V Y A Y A F V - - - - - - - - - - - - - L W E     D.Discoideum (U01064)
27   Y E A A G D E E L T L R R G D - R V Q V L S Q D - - - - - C     H.sapiens (Z48615)
27   Y E A A G D E E L T L R R G D - R V Q V L S Q D - - - - - C     Homo sapiens (Z48615)
16   - - - - - - - - - - - - - - G F K D A V F D G S - - - - - -    Human raf1 (W13107)
16   - - - - - - - - - - - - - - G F K D A V F D G S - - - - - -    Human Raf1kinase (R98215)
22   L D - - - - - P A R L G S I - - - - - - - - - - - - - P I S    Soybean kinase (M67449)

- - - - - - - - - - - - - - - - - - - - - - - - - - -  Majority
                        |                   |                   |
                       70                  80                  90
                        |                   |                   |
48   I F G S D E A F S K V N L N Y R T E N G L S L L H L C C I C     CARP2/prot
 8   - - - - - - - - - - - - - - - - - - - - - - - - - - - - -      A.thaliana kinase2
12   - - - - - - - - R W - - - - - - - - - - - - - - - - - - -      A.thaliana3
39   I A Q R K L G W - - - - - - - - - - - - - - - - - - - - -      Arabidopsis thaliana
53   H M C P E N A - - - - - - E L K S T Q L L S L F H I I C A -     c.elegans kinase
 1   - - - - - - - - - - - - - - - - - - - - - - - - - - - - -      D.discoideum (A35670)
28   A L T S H L P F R K - - - - - - - - - - - - - - - - - - -      D.Discoideum (U01064)
51   A V S G D E G W W T G Q L - - - P S G R V G V F P S N Y V A     H.sapiens (Z48615)
51   A V S G D E G W W T G Q L - - - P S G R V G V F P S N Y V A     Homo sapiens (Z48615)
26   - - - - - - - - - - - - - - - - - - - - - - S C I S            Human raf1 (W13107)
26   - - - - - - - - - - - - - - - - - - - - - - S C I S            Human Raf1kinase (R98215)
34   V Q S E Q K S R P S - - - - - - - - - - - - - - - - - - -      Soybean kinase (M67449)
```

Fig. 3

```
         - - S - A - - - - L Q - - L P N L R P - - - - - L - E - - -   Majority
                       |               |                   |
                      100             110                 120
                       |               |                   |
 78  G G K K S H I R T L - - M L K G L R P - - - - - - S R L T         CARP2/prot
  8  - - - - - - - - - - - - - - - - - - - - - - - - - - - - -         A.thaliana kinase2
 14  - - S L R S K L P L E P S L P N L P C N P S S S K T N R - -       A.thaliana3
 47  - - - - - - - - - - - - - - - - - - - - - - - - - - - - -         Arabidopsis thaliana
 76  G H S D S Q P E K L Q F L I D N L P K E S S I T L I S S Q S       c.elegans kinase
  1  - - - - - - - - - - - - - - - - - - - - - - - - - - - - -         D.discoideum (A35670)
 38  - - F N D I S V A A K V A Y E N L R P K I P T S - C P L - -       D.Discoideum (U01064)
 78  P G A P A A P A G L Q - - L P Q E I P F H E L Q L E E I I G       H.sapiens (Z48615)
 78  P G A P A A P A G L Q - - L P Q E I P F H E L Q L E E I I G       Homo sapiens (Z48615)
 30  P T I V Q - - - - - Q F G Y Q R - R A S D D G K L T D P S K       Human raf1 (W13107)
 30  P T I V Q - - - - - Q F G Y Q R - R A S D D G K L T D P S K       Human Raf1kinase (R98215)
 44  - - S K A Q R H P M T Y K Q R S L S P L P E T Y L S E A - -       Soybean kinase (M67449)

- - - - - - - - - - - - R G A R T L V K K R F A A - - D D S   Majority
                       |               |                   |
                      130             140                 150
                       |               |                   |
 99  R N G F T A L H L A V Y K D N A E L I T S L L H S G - A D I       CARP2/prot
  8  - - - - - - - - - - - D G N N T T K E K I F - - - - - - -         A.thaliana kinase2
 40  - - - - - - - - - - Y A E A E T M E K K R F D S - - M E S         A.thaliana3
 47  - - - - - G Q F S T V W L A Y D T L T S T Y V A L K I Q K S       Arabidopsis thaliana
106  A N G F T P L H I A I Y R G D V A I L K A L I A T K L V D L       c.elegans kinase
  1  - - - - - - - - - - - - - - - - - - - - - - - - - - - - -         D.discoideum (A35670)
 63  - - - - - - - - - - - F I - R K L I N R C W A P - - L P S         D.Discoideum (U01064)
106  V G G F G K V Y R A L W R G E E V A V K - - - A A R L D P E       H.sapiens (Z48615)
106  V G G F G K V Y R A L W R G E E V A V K - - - A A R L D P E       Homo sapiens (Z48615)
 54  T S N T I R V F L P - - N K Q R T V V N V R N G M S L H D C       Human raf1 (W13107)
 54  T S N T I R V F L P - - N K Q R T V V N V R N G M S L H D C       Human Raf1kinase (R98215)
 70  - - - - - - - - - - - F R E A R - L E Q K R F S T - - P N P       Soybean kinase (M67449)

- - - - - - - - L - - L - - - - - - G - - - - - - - - - G     Majority
                       |               |                   |
                      160             170                 180
                       |               |                   |
128  Q Q V G Y G G L T A L H I A T I A G H L E A A D V L L Q H G       CARP2/prot
 19  - R A D K I D L K S L D - - - - - - - - - - - - - - - - -         A.thaliana kinase2
 57  W - - - - - - S M I L E S E N V E T - - - - - - - - - - -         A.thaliana3
 72  A Q Q F A Q A A - - - - - - - - - - - - - - - - - - - - -         Arabidopsis thaliana
136  D Q S G R H L L P A L H L A A M I G D S E M L T I L L N S G       c.elegans kinase
  1  - - - - - - - - - - - - - - - - - - - - - - - - - - - - -         D.discoideum (A35670)
 78  D R P T F N D I L K L - F D H L E G - - - - - - - - - - -         D.Discoideum (U01064)
133  K D P A V T A E Q V C Q E A R L F G A L Q H P N I I A L R G       H.sapiens (Z48615)
133  K D P A V T A E Q V C Q E A R L F G A L Q H P N I I A L R G       Homo sapiens (Z48615)
 82  - - - - - - - - - - - - - - - - - - - L M K A L K V R G           Human raf1 (W13107)
 82  - - - - - - - - - - - - - - - - - - - L M K A L K V R G           Human Raf1kinase (R98215)
 86  R R E K R I M G K L L N K D S R E T - - - - - - - - - - -         Soybean kinase (M67449)
```

Fig. 3 cont.

```
                                          - - R - - -    Majority
                    |              |              |
                   190            200            210
                    |              |              |
158  A N V N I Q D A V F F T P L H I A A Y Y G H E Q V T[R]L L L   CARP2/prot
 30  - - - - - - - - - - - - - - - - - - - - - - - - - - - - -   A.thaliana kinase2
 69  - - - - - - - - - - - - - - - - - - - - - - - - - - - - -   A.thaliana3
 80  - - - - - - - - - - L H E I E F L S A A A D G D L - -       Arabidopsis thaliana
166  A N I H V T D F V H F T A L H C A T Y F G Q E N A V[R]T L I   c.elegans kinase
  1  - - - - - - - - - - - - - - - - - - - - - - - - - - - - -   D.discoideum (A35670)
 95  - - - - - - - - - - - - - - - - - - - - - - - - - - - - -   D.Discoideum (U01064)
163  A C L N P P H L C L - - - - - V M E Y A R G G A L S[R]V L A   H.sapiens (Z48615)
163  A C L N P P H L C L - - - - - V M E Y A R G G A L S[R]V L A   Homo sapiens (Z48615)
 91  - - L Q P E C C A V F R L L H E - - - - H K G K K A[R]L D W   Human raf1 (W13107)
 91  - - L Q P E C C A V F R L L H E - - - - H K G K K A[R]L D W   Human Raf1kinase (R98215)
104  - - - - - - - - - - - - - - - - - - - - - - - - - - - - -   Soybean kinase (M67449)

- - - - - - - - - - - - - - - - - - - - - - - - - - L - - - -   Majority
                    |              |              |
                   220            230            240
                    |              |              |
188  K F G A D V N V S G E V G D R P L H L A S A K G F[L]N I A K   CARP2/prot
 30  - - - - - - - - - - - - - - - - - - - - - - - - - - - - -   A.thaliana kinase2
 69  - - - - - - - - - - - - - - - - - - - - - - - - - - - - -   A.thaliana3
 95  - - - - - - - - - - D K T K C V V R L I D H F K H S G         Arabidopsis thaliana
196  S A S A N L N L G G A V N D R P I H L A A A K G L T S I T K   c.elegans kinase
  1  - - - - - - - - - - - - - - - - - - - - - - - - - - - - -   D.discoideum (A35670)
 95  - - - - - - - - - - - - - - - - - - - - - - - - - - - - K   D.Discoideum (U01064)
188  G R R V P P H V - - - L V N W A V Q V A R G M N Y[L]H N D A   H.sapiens (Z48615)
188  G R R V P P H V - - - L V N W A V Q V A R G M N Y[L]H N D A   Homo sapiens (Z48615)
115  N T D A A S L I G E E L - - - - - - - - - Q V D F[L]D H - -   Human raf1 (W13107)
115  N T D A A S L I G E E L - - - - - - - - - Q V D F[L]D H - -   Human Raf1kinase (R98215)
104  - - - - - - - - - - - - - - - - - - - - - - - - - - - - K   Soybean kinase (M67449)

- - - L - - - - - - - - - - L - - - - - - - - K L A - - - 1     Majority
                    |              |              |
                   250            260            270
                    |              |              |
218  - - -[L]L M E E G S K A D V N A Q D N E D H V P[L]H F C S R   CARP2/prot
 30  - - - - - - - - - - - - - - - - - R Q L E K H[L]S - - - -   A.thaliana kinase2
 69  - - - - - - - - - - - - - - - - - - - - - - - - - - - - -   A.thaliana3
122  P - - - - - - - - - - - - - - - - - - - - - N G Q H L C - -   Arabidopsis thaliana
226  - - -[L]L L E - - A K A D P[L]L A D D E G N Q A[L]H Y A A K   c.elegans kinase
  1  - - - - - - - - - - - - - - - - - - - - - - - - - - - - -   D.discoideum (A35670)
 96  - - -[L]F F S S P G I L R S[L]N N D Q E V E R E[L]Q - - - -   D.Discoideum (U01064)
215  P V P I I H R D L K S I N I[L]I L E A I E N H N[L A]- - - -   H.sapiens (Z48615)
215  P V P I I H R D L K S I N I[L]I L E A I E N H N[L A]- - - -   Homo sapiens (Z48615)
134  - V P[L]T T H N F A R K T F[L]- - - - - - - -[K L A]F C D -   Human raf1 (W13107)
134  - V P[L]T T H N F A R K T F[L]- - - - - - - -[K L A]F C D -   Human Raf1kinase (R98215)
105  - - - - - - E S S S K S P S R S P N R Q V K S[K]N R - - - -   Soybean kinase (M67449)
```

Fig. 3 cont

```
          - - - - - - - F L - - - - - - - - - - - - - - - - - Y - - -   Majority
                        |                 |                 |
                       280               290               300

245 F G H H D I V K Y L L Q S D L E V Q P H V V - - N I Y G - -   CARP2/prot
 38 - - - - - - - - - - - - - - - - - - - - - - - - - - - - - -   A.thaliana kinase2
 69 - - - - - - - - - - - - - - - - - - - - - - - - - - - - - -   A.thaliana3
119 - - - - M V L E F L - - - - - - - - - - - - - - - - - - - -   Arabidopsis thaliana
251 S G S L V I L N M L I K Q V R G T N D R I C A R N L Y G - -   c.elegans kinase
  1 - - - - - - - - - - - - - - - - - - - - - - - - - - - - - -   D.discoideum (A35670)
119 - - - - - - - - - - - - - - - - - - - - - - - - - - - - - -   D.Discoideum (U01064)
241 D T V L K I T D F G L A R E W H K T T K M S A A G T Y A W M   H.sapiens (Z48615)
241 D T V L K I T D F G L A R E W H K T T K M S A A G T Y A W M   Homo sapiens (Z48615)
154 - - - - I C Q K F L L N G F R - - - - - - C Q T C G Y K F H   Human raf1 (W13107)
154 - - - - I C Q K F L L N G F R - - - - - - C Q T C G Y K F H   Human Raf1kinase (R98215)
125 - - - - - - - - - - - - - - - - - - - - - - - - - - - - - -   Soybean kinase (M67449)

- - - - - L - - - - - K - - V W S - I L Q - L L - - - - - -   Majority
                        |                 |                 |
                       310               320               330

271 - D T P L H L A C Y N G K F E V A K E I I Q I S G T E S L T   CARP2/prot
 38 - - - - - - - - - - - R - - V W S R N L E - - - - - - V N     A.thaliana kinase2
 69 - - - - - - - - - - - - - W E - - - - - - - - - - - - A S     A.thaliana3
125 G D S L L R L I R Y N Q - - - - - - - - - - - - - - - - -     Arabidopsis thaliana
279 - D T A L H L S C Y S G R L D I V K S I L D S S P T N I V N   c.elegans kinase
  1 - - - - - - - - - - - - - - - - - - - - - - - - - - - - - -   D.discoideum (A35670)
119 - - - - - - - - - - K K E R F N E I T E F L R G K K - -       D.Discoideum (U01064)
271 A P E V I R L S L F S K S S D V W S - - F G V L L W E L L T   H.sapiens (Z48615)
271 A P E V I R L S L F S K S S D V W S - - F G V L L W E L L T   Homo sapiens (Z48615)
174 E H C S T K V P - - - T M C V D W S N I R Q L L L - - - -     Human raf1 (W13107)
174 E H C S T K V P - - - T M C V D W S N I R Q L L L - - - -     Human Raf1kinase (R98215)
125 - - - - - - - - - - K D S A W T K L L D N G G G K I T A       Soybean kinase (M67449)

- E - - - - - - - - - - - - - - - - - - - - - - - - -   Majority
                        |                 |                 |
                       340               350               360

300 K E N I F S E T A F H S A C T Y G K S I D L V K F L L D Q N   CARP2/prot
 48 P K A - - - - - - - - - - - - - - - - - - - - - - - - - - -   A.thaliana kinase2
 73 K G E - - - - - - - - - - - - - - - - - - - - - - - - - - -   A.thaliana3
137 - - - - Y K G L K L N - - - - - - K V R E I C R C I L - - -   Arabidopsis thaliana
308 M E N V F S E T P L H A A C T G G K S I E L V S F L M K Y P   c.elegans kinase
  1 - - - - - - - - - - - - - - - - - - - - - - - - - - - - - -   D.discoideum (A35670)
135 - - - - - - - - - - - - - - - - - - - - - - - - - - - - - -   D.Discoideum (U01064)
299 G E V P Y R E I D - A L A V A Y G - - V A M N K L T L P I P   H.sapiens (Z48615)
299 G E V P Y R E I D - A L A V A Y G - - V A M N K L T L P I P   Homo sapiens (Z48615)
196 - - - - F P N S T I - - - - G D S G V P A L P S L T M R - -   Human raf1 (W13107)
196 - - - - F P N S T I - - - - G D S G V P A L P S L T M R - -   Human Raf1kinase (R98215)
143 V E T - - - - - - - - - - - - - - - - - - - - - - - - - - -   Soybean kinase (M67449)
```

Fig. 3 cont.

```
                                                                    Majority
              |                   |                   |
             370                 380                 390
              |                   |                   |
330 V I N I N H Q G R D G H T G L H S A C Y - - - - H G H I R L    CARP2/prot
 51 - - - - - - - - - - - - - - - - - - - - - - - - - - - - - -    A.thaliana kinase2
 76 - - - - - - - - - - - - - - - - - - - - - - - - - - - - - -    A.thaliana3
154 - - - - - - - - - - - T G L - - - - - - - - - - - - - - - -    Arabidopsis thaliana
338 G V D P N Y Q G Q D G H T A L H S A C Y - - - - H G H L R I    c.elegans kinase
  1 - - - - - - - - - - - - - - - - - - - - - - - - - - - - - -    D.discoideum (A35670)
135 - - - - - - - - - - - - - - - - - - - - - - - - - - - - - -    D.Discoideum (U01064)
326 S T C P E P F A R - - - - - L L E E C W D P D P H G R P D F    H.sapiens (Z48615)
326 S T C P E P F A R - - - - - L L E E C W D P D P H G R P D F    Homo sapiens (Z48615)
216 - - - - - - - - - - - - - - - - - - - - - - - - - - - - R M    Human raf1 (W13107)
216 - - - - - - - - - - - - - - - - - - - - - - - - - - - - R M    Human Raf1kinase (R98215)
146 - - - - - - - - - - - - - - - - - - - - - - - - - - - - - -    Soybean kinase (M67449)

- - - L - - - - - - - - - - - - - - - - - - - - - - - E - -   Majority
              |                   |                   |
             400                 410                 420
              |                   |                   |
356 V Q F L - - L D N G A D M N L V A - - - - - - - - - - - - -    CARP2/prot
 51 - - - - - - - - - - - - - - - - - - - - - - - - - K E E -     A.thaliana kinase2
 76 - - - - - - - - - - - - - - - - - - - - - - - - - R E E -     A.thaliana3
157 - D Y L H R - - - - - - - - - - - - - - - - - - - - - - - -   Arabidopsis thaliana
364 V Q Y L - - L E N G A D Q S L A S R A F E G - G A L R Q Q -    c.elegans kinase
  1 - - - - - - - - - - - - - - - - - - R P F G G - - - - - - -   D.discoideum (A35670)
135 - - - - - - - - - - - - - - - - - - - - - - - - - - - - - -   D.Discoideum (U01064)
351 G S I L K R L E V I E Q S A L F Q M P L E S F H S L Q E D W    H.sapiens (Z48615)
351 G S I L K R L E V I E Q S A L F Q M P L E S F H S L Q E D W    Homo sapiens (Z48615)
218 R E S V S R M P V S S Q H R Y S T P H A F T F N T S S P S S    Human raf1 (W13107)
218 R E S V S R M P V S S Q H R Y S T P H A F T F N T S S P S S    Human Raf1kinase (R98215)
146 - - - - - - - - - - - - - - - - - - - - - - - - - A E E -     Soybean kinase (M67449)

Majority
              |                   |                   |
             430                 440                 450
              |                   |                   |
371 - - - - - - - C D P S R S S G E K - - - - - - - - - - - - -    CARP2/prot
 54 - - - - - - - - - - - - - - - - - - - - - - - - - - - - - -    A.thaliana kinase2
 79 - - - - - - - - - - - - - - - - - - - - - - - - - - - - - -    A.thaliana3
162 E L G M I H - - - - - - - - - S D L K P E N I L L C S T I D    Arabidopsis thaliana
390 - - - - - - - A G P G T N R P S K V A S A I M A L N R S D T    c.elegans kinase
  6 - - - - - - - - - - - - - - - - - - - - - - - - - - - - - -    D.discoideum (A35670)
135 - - - - - - - - - - - - - - - - - - - - - - - - - - - - - -    D.Discoideum (U01064)
381 K L E I Q H M F D D L R T K E K E L R S R E E E L L R A - -    H.sapiens (Z48615)
381 K L E I Q H M F D D L R T K E K E L R S R E E E L L R A - -    Homo sapiens (Z48615)
248 E - - - - - - G S L S Q R Q R S T S T P N V H M V S T T L      Human raf1 (W13107)
248 E - - - - - - G S L S Q R Q R S T S T P N V H M V S T T L      Human Raf1kinase (R98215)
149 - - - - - - - - - - - - - - - - - - - - - - - - - - - - - -    Soybean kinase (M67449)
```

Fig. 3 cont.

```
                    - - - - - - - - - - - - - - - - - - - - - W E L D - - - - -    Majority
                    ─────────────────────────────────────────────────────────────
                              |                   |                  |
                             460                 470                480
                              |                   |                  |
381  - - - - - - - - - - - - D E Q T C L M W A Y E K G H D A                         CARP2/prot
 54  - - - - - - - - - - - - - - - - - - - W E I D - - - - -                         A.thaliana kinase2
 79  - - - - - - - - - - - - - - - - - - - W T A D - - - - -                         A.thaliana3
183  P A K D P - - - - - - - - - - - - - - - - - - V R S G                           Arabidopsis thaliana
413  P S S N A S Y N S T V S L D D Q Q T P V I W A Y E R G H D A                     c.elegans kinase
  6  - - - - - - - - - - - - - - - - - - - W E T Q S S - - -                         D.discoideum (A35670)
135  - - - - - - - - - - - - - - - - - - - - E I K - - - - -                         D.Discoideum (U01064)
409  - A Q E Q R F Q E E Q L R R R E Q E L A E R E M D I V E R E                     H.sapiens (Z48615)
409  - A Q E Q R F Q E E Q L R R R E Q E L A E R E M D I V E R E                     Homo sapiens (Z48615)
271  P V D S - R M I E D A I R S H S E S A S P S A L S S S P N N                     Human raf1 (W13107)
271  P V D S - R M I E D A I R S H S E S A S P S A L S S S P N N                     Human Raf1kinase (R98215)
149  - - - - - - - - - - - - - - - - - - - W N V D - - - - -                         Soybean kinase (M67449)

L - - - - - - - - - - - - - - - - - - - - - - - - - - - - - - -                Majority
     ─────────────────────────────────────────────────────────────────
                              |                   |                  |
                             490                 500                510
                              |                   |                  |
397  I V T L L K H Y K - - R P Q D E L P C N E Y S Q P G - - - -                     CARP2/prot
 58  - - - - - - - - - - - - - - - - - - - - - - - - - - - -                         A.thaliana kinase2
 83  - - - - - - - - - - - - - - - - - - - - - - - - - - - -                         A.thaliana3
192  L T P L L - - - - - E K P E G N A N G G A - - - S T M N L I                     Arabidopsis thaliana
443  I V A L L K H Y A A - R T V E G D V C S E Y S - - S - - - -                     c.elegans kinase
 12  - - - - L S H P P S - R P P - - - - - - - - - - - - - -                         D.discoideum (A35670)
138  - - - - - - - - - - - - - - - - - - - - - - - - - - - -                         D.Discoideum (U01064)
438  L H L L M C Q L S Q E K P R V R K R K G N F K R A V L K L R                     H.sapiens (Z48615)
438  L H L L M C Q L S Q E K P R V R K R K G N F K R A V L K L R                     Homo sapiens (Z48615)
300  L S P - - - - - - - - - - - - - - - T G W S Q P K - - - -                       Human raf1 (W13107)
300  L S P - - - - - - - - - - - - - - - T G W S Q P K - - - -                       Human Raf1kinase (R98215)
153  - - - - - - - - - - - - - - - - - - - - - - - - - - - -                         Soybean kinase (M67449)

- - - - - - - - P - - - - - - - - - - - - - - - - L - - R -                    Majority
     ─────────────────────────────────────────────────────────────
                              |                   |                  |
                             520                 530                540
                              |                   |                  |
421  G D G S Y V S V P S P L G K I K S M T K E K A D I L L R A                       CARP2/prot
 58  - - - - - - - - - - - - - - - - - - - - - - - - - - - -                         A.thaliana kinase2
 83  - - - - - - - - - - - - - - - - - - - - - - - - - - - -                         A.thaliana3
214  E - - - - - - - - - - - - - - - - - - - K K L K R R A                           Arabidopsis thaliana
466  G E S S Y T P L P S P M G R L T S L T R D K A D L L Q L R S                     c.elegans kinase
 21  - - - - - - P P P P P P P Q L P - - - - - - - - - - - -                         D.discoideum (A35670)
138  - - - - - - - - - - - - - - - - - - - - - - - - - - - -                         D.Discoideum (U01064)
468  E G S S H I S L P S G F E H - - K I T V Q A S P T L D K R K                     H.sapiens (Z48615)
468  E G S S H I S L P S G F E H - - K I T V Q A S P T L D K R K                     Homo sapiens (Z48615)
310  - - - - - T P V P A Q R E R A P V S G T Q E K N K I R P R G                     Human raf1 (W13107)
310  - - - - - T P V P A Q R E R A P V S G T Q E K N K I R P R G                     Human Raf1kinase (R98215)
153  - - - - - - - - - - - - - - - - - - - - - - - - - - - -                         Soybean kinase (M67449)
```

Fig. 3 cont.

```
            - - D - - - - - - - - L S E L E F G L R I G S G S F G T V Y   Majority
                          |                   |                     |
                         550                 560                   570

151 G L P S H F - - H L Q L S E I E F H E I I G S G S F G K V Y   CARP2/prot
 58 - - - - - - - - - - - L A K L E T S N V I A R G T Y G T V Y   A.thaliana kinase2
 33 - - - - - - - - - - - L S Q L F I G N K F A S G A H S R I Y   A.thaliana3
222 K R A - - - - - - - - - - - - - - - - - - - - - - - - - - -   Arabidopsis thaliana
496 A L P A P F - - H L C L A E I E F Q E S I G S G S F G K V Y   c.elegans kinase
 81 - V R S E Y - - E I D F N E L E F G Q T I G K G F F G E V K   D.discoideum (A35670)
138 - - - - - - - - - - - F D E V A I V E K V G A G S F A N V F   D.Discoideum (U01064)
496 G S D G A S - - P P A S P S I I P R L R A I R L T P V D C G   H.sapiens (Z48615)
496 G S D G A S - - P P A S P S I I P R L R A I R L T P V D C G   Homo sapiens (Z48615)
335 Q R D S S Y Y W E I E A S E V M L S T R I G S G S F G T V Y   Human raf1 (W13107)
335 Q R D S S Y Y W E I E A S E V M L S T R I G S G S F G T V Y   Human Raf1kinase (R98215)
153 - - - - - - - - - - - M S Q L F F G L K F A H G A H S R L Y   Soybean kinase (M67449)

K G I Y R G - D V A V K I L K R G D P - - E - - - - - K - E   Majority
                          |                   |                     |
                         580                 590                   600

479 K G R C R N K I V A I K R - Y R A N - - - - - T Y C S K S D   CARP2/prot
 77 K G I Y D G Q D V A V K V L D W E D D G N E T T A K T A T N   A.thaliana kinase2
102 R G I Y K Q R A V A V K M V R I P T H K E E T R - - A K L E   A.thaliana3
225 - - - - - - - - - - - - - - - - - - - - - - - - - - - - - -   Arabidopsis thaliana
524 K G T Y R G K L V A V K R - Y R A M - - - - - A F G C K S E   c.elegans kinase
 58 R G Y W R E T D V A I K I Y R D Q - - - - - - F K T K S S     D.discoideum (A35670)
157 L G I W N G Y K V A I K I L K N E S I S N D E K - - - - - -   D.Discoideum (U01064)
524 G S S S G S S S G G S G T W S R G G P P K K E E L V G G K K   H.sapiens (Z48615)
524 G S S S G S S S G G S G T W S R G G P P K K E E L V G G K K   Homo sapiens (Z48615)
365 K G K W H G - D V A V K I L K V V D P T P E - - - - - - - Q   Human raf1 (W13107)
365 K G K W H G - D V A V K I L K V V D P T P E - - - - - - - Q   Human Raf1kinase (R98215)
172 H G V Y K D E A V A V K I I M V P E D D G N G A L A S R L E   Soybean kinase (M67449)

K Q - F R N E V S V L S K L R H P N V V Q F V G A - L - - -   Majority
                          |                   |                     |
                         610                 620                   630

503 V D M F C R E V S I L C Q L N H P C V I Q F V G A C L - N -   CARP2/prot
107 R A L F R Q E V T V W H K L N H P N V T K F V G A S M G T T   A.thaliana kinase2
130 Q Q - F K S E V A L L S R L F H P N I V Q F I A A C K - - -   A.thaliana3
225 - - - - - - - - - V A K I S E R R V S M V T G E - - - - -     Arabidopsis thaliana
548 T D M L C R E V S I L S R L A H P N V V A F V G T S L - D -   c.elegans kinase
 82 L V M F Q N E V G I L S K L R H P N V V Q F L G A C T A G -   D.discoideum (A35670)
181 - - - F I K E V S S L I K S H H P N V V T F M G A - - - - -   D.Discoideum (U01064)
554 K G R T W G P S S T L Q K E R V G G E E R L K G - - L G E G   H.sapiens (Z48615)
554 K G R T W G P S S T L Q K E R V G G E E R L K G - - L G E G   Homo sapiens (Z48615)
387 F Q A F R N E V A V L R K T R H V N I L L F M G Y - - - - -   Human raf1 (W13107)
387 F Q A F R N E V A V L R K T R H V N I L L F M G Y - - - - -   Human Raf1kinase (R98215)
202 K Q - F I R E V T L L S R L H H Q N V I K F S A A C R - - -   Soybean kinase (M67449)
```

Fig. 3 cont.

```
                  - - - - - - - - - - - - D P H H L C I V T E Y L S G G S L  Majority
                                        |                |                |
                                       640              650              660
531 - - - - - - - - - - - - D P S Q F A I V T Q Y I S G G S L  CARP2/prot
137 N L N I R S A D S K G S L P Q Q A C C V V E Y L P G G T L  A.thaliana kinase2
156 - - - - - - - - - - - - K P P V Y C I I T E Y M S Q G N L  A.thaliana3
240 - - - - - - - - - - - - - - - - - - - - - - - - - - - - - Arabidopsis thaliana
576 - - - - - - - - - - - - D P S Q F A I I T E F V E N G S L  c.elegans kinase
111 - - - - - - - - - - - - G E D H C I V T E W M G G G S L    D.discoideum (A35670)
203 - - - - - - - - - - R I D P P - - C I F T E Y L Q G G S L  D.Discoideum (U01064)
582 S K Q W S S S A P N L G K S P K H T P I A P G F A S L N E M  H.sapiens (Z48615)
582 S K Q W S S S A P N L G K S P K H T P I A P G F A S L N E M  Homo sapiens (Z48615)
412 - - - - - - - - - - - - M T K D N L A I V T Q W C E G S S L  Human raf1 (W13107)
412 - - - - - - - - - - - - M T K D N L A I V T Q W C E G S S L  Human Raf1kinase (R98215)
228 - - - - - - - - - - - - K P P V Y C I I T E Y L A E G S L    Soybean kinase (M67449)

R E H L H - E D - K F S L L P - - - - - - - - L K I A L D I  Majority
                            |                |                |
                           670              680              690
548 F S L H E Q K - - - R I L D - - L Q S K - - L I I A V D V    CARP2/prot
167 K Q H L I - R H K S K K L A F K A V - - - - - I K L A L D L  A.thaliana kinase2
173 R M Y L N - K K E P Y S L S I E T V - - - - - L R L A L D I  A.thaliana3
240 - - - - - - - - - - - - - - - - - - - - - - - - - - - - -   Arabidopsis thaliana
593 F R R E N G E R K N Y R V M D - - P A F R - - L R I S L D V  c.elegans kinase
128 R Q F L T D H - - - F N L L E Q N P H I R - - L K L A L D I  D.discoideum (A35670)
220 Y D V L H - - I Q K I K L N P L M M - - - - - Y K M I H D L  D.Discoideum (U01064)
612 E E F A E A E D G G S S V P P S P Y S T P S Y L S V P L P A  H.sapiens (Z48615)
612 E E F A E A E D G G S S V P P S P Y S T P S Y L S V P L P A  Homo sapiens (Z48615)
430 Y K H L H V Q E T K F Q M F Q - - - - - - - L I D I A R Q T  Human raf1 (W13107)
430 Y K H L H V Q E T K F Q M F Q - - - - - - - L I D I A R Q T  Human Raf1kinase (R98215)
245 R A Y L H - K L E H Q T I S L Q K L - - - - - I A F A L D I  Soybean kinase (M67449)

A R G M E Y L H - - - A Q P I I H R D L K S H N I L L D E -  Majority
                       |                |                |
                      700              710              720
571 A K G M E Y L H N - L T Q P I I H R D L N S H N I L L Y - -  CARP2/prot
191 A R G L S Y L H - - - S E K I V H R D V K T E N M L L D A Q  A.thaliana kinase2
197 S R G M E Y L H - - - S Q G V I H R D L K S N N L L L N D E  A.thaliana3
240 - - - - - - - - - - E A S S K T E K S L D G I D M - - - - -  Arabidopsis thaliana
619 A R G M R Y L H E S A A K P V I H R D L N S H N I L I H - -  c.elegans kinase
153 A K G M N Y L H G W - T P P I L H R D L S S R N I L L D H N  D.discoideum (A35670)
243 S L G M E H L H - - - S I Q M L H R D L T S K N I L L D E F  D.Discoideum (U01064)
642 E P S P G A R A P W E P T P S A P P A R W G H G - - - - A R  H.sapiens (Z48615)
642 E P S P G A R A P W E P T P S A P P A R W G H G - - - - A R  Homo sapiens (Z48615)
453 A Q G M D Y L H - - - A K N I I H R D M K S N N I F L H E G  Human raf1 (W13107)
453 A Q G M D Y L H - - - A K N I I H R D M K S N N I F L H E G  Human Raf1kinase (R98215)
269 A R G M E Y I H - - - S Q G V I H R D L K P E N I L I N E D  Soybean kinase (M67449)
```

Fig. 3 cont.

```
                    - R V K - - - - - - - - - - - - - I A D F G L A R - L E A -    Majority
                                    |                         |                    |
                                   730                       740                  750
                                    |                         |                    |
598 - - - - - - - - - - - E D G H A V V A D F G E S R F L Q S -    CARP2/prot
218 K N L K - - - - - - - - - - - - - I A D F G V A R - V E A -    A.thaliana kinase2
224 M R V K - - - - - - - - - - - - - V A D F G T S C - L E T -    A.thaliana3
255 - - - - - - - - - - - - - - R C K V V D F G N A C - - - - W    Arabidopsis thaliana
647 - - - - - - - - - - - A D G R S V V A D F G E S R F V C Q -    c.elegans kinase
182 I D P K N P L V S S R Q D I K C K I S D F G L S R - L K K -    D.discoideum (A35670)
270 K N I K - - - - - - - - - - - - - I A D F G L A - - - T T -    D.Discoideum (U01064)
668 R R C D L A L L G C - - - - - - - A T L L G A V G L G A D -    H.sapiens (Z48615)
668 R R C D L A L L G C - - - - - - - A T L L G A V G L G A D -    Homo sapiens (Z48615)
480 L T V K - - - - - - - - - - - - - I G D F G L A T V K S R W    Human raf1 (W13107)
480 L T V K - - - - - - - - - - - - - I G D F G L A T V K S R W    Human Raf1kinase (R98215)
296 N H L K - - - - - - - - - - - - - I A D F G I A C - E E A -    Soybean kinase (M67449)

L A D D Q A A D G T G T L R W M A P E V F I - - K G G P Y S    Majority
                          |                         |                    |
                         760                       770                  780
                          |                         |                    |
616 L D E D N M T K Q P G N L R W M A P E V F T - - Q C T R Y T    CARP2/prot
233 L N P K D M T G E T G T L G Y M A P E V - I - - D G K P Y N    A.thaliana kinase2
239 - Q C R E A K G N M G T Y R W M A P E M - I - - K E K P Y T    A.thaliana3
267 - A D K Q F A E E I Q T R Q Y R A P E V I L K - - - S G Y S    Arabidopsis thaliana
665 R E D E N L T K Q P G N L R W M A P E V F S - - Q S G K Y D    c.elegans kinase
210 E Q A S Q M T Q S V G C I P Y M A P E V F - - - K G D S N S    D.discoideum (A35670)
283 L S D D M T L S G I T N P R W R S P E L - T - - K G L V Y N    D.Discoideum (U01064)
690 V A E A R A A D G E E Q R R W L D G L F F P - - R A G R F P    H.sapiens (Z48615)
690 V A E A R A A D G E E Q R R W L D G L F F P - - R A G R F P    Homo sapiens (Z48615)
497 S G S Q Q V E Q P T G S V L W M A P E V I R M Q D N N P F S    Human raf1 (W13107)
497 S G S Q Q V E Q P T G S V L W M A P E V I R M Q D N N P F S    Human Raf1kinase (R98215)
311 - S C D L L A D D P G T Y R W M A P E M - I - - K R K S Y G    Soybean kinase (M67449)

R K V D V Y S F G L V L W E L V T G E L P F A H L N P - V Q    Majority
                          |                         |                    |
                         790                       800                  810
                          |                         |                    |
644 I K A D V F S Y A L C L W E I L T G E I P F A H L K P - A A    CARP2/prot
260 R R C D V Y S F G I C L W E I Y C C D M P Y P D L S F - V D    A.thaliana kinase2
265 R K V D V Y S F G I V L W E L T A L L P F Q G M T P - V Q    A.thaliana3
293 F S V D M W S F G C T A F E L V T G D M L F A P K D G N - -    Arabidopsis thaliana
693 R K V D V F S F A L V I W E I H T A E L P F S H L K P - A A    c.elegans kinase
237 E K S D V Y S Y G M V L F E L L T S D E P Q Q D M K P - M K    D.discoideum (A35670)
310 E K V D V Y S F G L V V Y E I Y T G K I P F E G L D G - T A    D.Discoideum (U01064)
718 R G L S P P A R P H G R R E D V G P G L G L A P S A T L V S    H.sapiens (Z48615)
718 R G L S P P A R P H G R R E D V G P G L G L A P S A T L V S    Homo sapiens (Z48615)
527 F Q S D V Y S Y G I V L Y E L M T G E L P Y S H I N N R D Q    Human raf1 (W13107)
527 F Q S D V Y S Y G I V L Y E L M T G E L P Y S H I N N R D Q    Human Raf1kinase (R98215)
337 K K V D V Y S F G I V L Y E L M T G T I P Y E D M N P - I Q    Soybean kinase (M67449)
```

Fig. 3 cont.

```
         A A F A V A Y G N A R P P L P S D C - - - - P A A L S S L I   Majority
                           |                 |                 |
                          820               830               840

673 A A A D M A Y H H I R P P I G Y S - - - - I P K P I S S L L   CARP2/prot
289 V S S A V L H N L R P E I P R C - - - - P T A L A G I M       A.thaliana kinase2
294 A A F A V A E K N E R P P L P A S C - - - - Q P A L A H L I   A.thaliana3
321 - - - - - G Y G E D E D H L A - - - - - - - - - - - - - -     Arabidopsis thaliana
722 A A A E M T Y K R G R P T L P N Q P T A Q F P A H I L S L I   c.elegans kinase
266 M A H L A Y E S Y R P P I P L T T S S K W K E - - - - I L     D.discoideum (A35670)
339 S A A K A F E N Y R P A I P P D C - - - - P V S L R K L I     D.Discoideum (U01064)
748 L S S V S D C N S T R S L L R S D S D E A A P A A P S P P P   H.sapiens (Z48615)
748 L S S V S D C N S T R S L L R S D S D E A A P A A P S P P P   Homo sapiens (Z48615)
557 I I F M V G R G Y A S P D L S K L Y K N C - P K A M K R L V   Human raf1 (W13107)
557 I I F M V G R G Y A S P D L S K L Y K N C - P K A M K R L V   Human Raf1kinase (R98215)
366 A A F A V N K N S R P I I P S N C - - - - P P A M R A L I     Soybean kinase (M67449)

A Q C W A P N P S K R P S F S E I V - - - L E - - - - - - -   Majority
                           |                 |                 |
                          850               860               870

699 I R G W N A C P E G R P E F S E V V M K - L E E C L C N I E   CARP2/prot
315 K T C W D G N P Q K R P E M K E V V K M - L E G V - - D T S   A.thaliana kinase2
320 K R C W S E N P S K R P D F S N I V A V - L E K Y - - D E C   A.thaliana3
331 - - - - - - - - - - - - - - - L M M E L - - - - - - - -       Arabidopsis thaliana
752 P Q A W H P E S S S R P D F V E I V - - - - - - - - - - A     c.elegans kinase
292 T Q C W D S N P D S R P T F K Q I I V H - L K E - - - - - -   D.discoideum (A35670)
365 T K C W A S D P S Q R P S F T E I L T E - L E T M - - K S K   D.Discoideum (U01064)
778 S P P - A P T P T P S P S T N P L V D L E L E S F K K D P R   H.sapiens (Z48615)
778 S P P - A P T P T P S P S T N P L V D L E L E S F K K D P R   Homo sapiens (Z48615)
586 A D C V K K V K E E R P L F P Q I L - - - - - - - - - - -     Human raf1 (W13107)
586 A D C V K K V K E E R P L F P Q I L - - - - - - - - - - -     Human Raf1kinase (R98215)
392 E Q C W S L Q P D K R P E F W Q V V K I - L E Q F - - E S -   Soybean kinase (M67449)

- - - - P - S V T S - - S L S L - - - - T P S - - - - - - -   Majority
                           |                 |                 |
                          880               890               900

728 L - M S P A S S N S S G S L S P - - - - S S S S D C L V N R   CARP2/prot
342 K - G G G M I P E - - - - - - - - - - - - - - - - - - - -     A.thaliana kinase2
347 V - K E G L P L T S H A S L T K - - - - T K K A - - - - - -   A.thaliana3
336 - - - - - - - - - - - - L G K M P R K I A I G G A - - - -     Arabidopsis thaliana
771 L - L E P H V E S T H T D I S A - - - - P S T V - - - - - -   c.elegans kinase
315 - - M E D Q G V S S F A S V P V - - - - Q T - - - - - - -     D.discoideum (A35670)
392 F - I K Q L S F L N D - - L I Q - - - - N P D - - - - - - -   D.Discoideum (U01064)
807 Q S L T P T H V T A A C A V S R G H R R T P S D G A L G Q R   H.sapiens (Z48615)
807 Q S L T P T H V T A A C A V S R G H R R T P S D G A L G Q R   Homo sapiens (Z48615)
604 - - - - - - - - - - - S S I E L L Q H S L P K - - - - I N R   Human raf1 (W13107)
604 - - - - - - - - - - - S S I E L L Q H S L P K - - - - I N R   Human Raf1kinase (R98215)
418 - - - - - S L A S D G T L S L - - - - V P N P - - - - - -     Soybean kinase (M67449)
```

Fig. 3 cont.

```
         - - - - - - - H - - - - - - - - - - - - - - - -      Majority
         |               |               |
        910             920             930

753 G G P G R S - H V A A L R S R F E L E Y A L N A R S Y A A L   CARP2/prot
350 - - - - - - - - - - - - - - - - - - - - - - - - - - - -     A.thaliana kinase2
366 - - - - - - - - - - - - - - - - - - - - - - - - - - - -     A.thaliana3
349 - - - K S K D Y F D R H G D L K R I R R L - - - - K Y W P L   Arabidopsis thaliana
790 - - - - - S - Q L T S Q W E Q L S V A - P P P A S K F P P I   c.elegans kinase
331 - - - - - - - - - - - - - - - - - - - - - - - - - - - -     D.discoideum (A35670)
408 - - - - - - - - - - - - - - - - - - - - - - - - - - - -     D.Discoideum (U01064)
837 G P P E P A G H G P G P R D L L D F P R L P D P Q A L F P A   H.sapiens (Z48615)
837 G P P E P A G H G P G P R D L L D F P R L P D P Q A L F P A   Homo sapiens (Z48615)
619 S A S E P S L H R A A H T E D I N - - - - - - - - - - -     Human raf1 (W13107)
619 S A S E P S L H R A A H T E D I N - - - - - - - - - - -     Human Raf1kinase (R98215)
432 - - - - - - - - - - - - - - - - - - - - - - - - - - - -     Soybean kinase (M67449)

- - - - - - - - - - - - L T - D P - K G P - - - - - - D  Majority
         |               |               |
        940             950             960

782 S Q S A G Q Y S S - - Q G L S L E E M K R S L Q Y T P - I D   CARP2/prot
350 - - - - - - - - - - - - - - D Q S R G C F C - - - - - -     A.thaliana kinase2
366 - - - - - - - - - - - - I L D H L K G C V T S I S - - S     A.thaliana3
372 D R - - - - - - - - - - - L L I D K Y K L P E A E A K E F A   Arabidopsis thaliana
813 L S A L H G I A A - - T G - T V E E L R Q R - - - - - - I D   c.elegans kinase
331 - - - - - - - - - - - - - - - - - - - - - - - - - - I D     D.discoideum (A35670)
408 - - - - - - - - - - - - - - D D Y N N L N Y D E E V D       D.Discoideum (U01064)
867 R R R P P E F P G R P T T L T F A P R P R P A A S R P R L D   H.sapiens (Z48615)
867 R R R P P E F P G R P T T L T F A P R P R P A A S R P R L D   Homo sapiens (Z48615)
636 - - - - - - - - - - A C T L T T S P - - - - - - - - - -     Human raf1 (W13107)
636 - - - - - - - - - - A C T L T T S P - - - - - - - - - -     Human Raf1kinase (R98215)
432 - - - - - - - - - - - - C W D H K G L L H W I Q K L G       Soybean kinase (M67449)

P F - - - - - - - - L - I - P - - - P - - - - - - - -   Majority
         |               |               |
        970             980             990

809 K Y - - - - - - - G Y V S D P M S S M H F H S C R N S S S F   CARP2/prot
358 - F - - - - - - - A P A R G P                               A.thaliana kinase2
380 P F - - - - - - - S S S S V P V N - - - - - - - - - - -     A.thaliana3
391 E F - - - - L T P I L E F A P E K R P T A Q Q C - - - - L   Arabidopsis thaliana
834 N N - - - - - - - G Y V I N - - - - - - - - - - - - - -     c.elegans kinase
333 T G - - - - - - - V Y - - - - - - - - - - - - - - - - -     D.discoideum (A35670)
422 S                                                           D.Discoideum (U01064)
897 P W K L V S F G R T L T I S P P S R P D T P E S P G P P S V   H.sapiens (Z48615)
897 P W K L V S F G R T L T I S P P S R P D T P E S P G P P S V   Homo sapiens (Z48615)
644 - - R L P N F                                               Human raf1 (W13107)
644 - - R L P V F                                               Human Raf1kinase (R98215)
448 P L - - - - - - - H Q N S G P V P K P K F - - - - - - -     Soybean kinase (M67449)
```

Fig. 3 cont.

```
                                                  Majority
              |            |
             1000         1010
              |            |
832 E - - - - - - - - - - - - - - - - - - - - - D S S   CARP2/prot
364                                                     A.thaliana kinase2
390 - - - - - - - - - - - - - - - - - - - - - - - - A   A.thaliana3
412 D H P W M N V T T Q N D A E N V D D Q M N N L H I K G   Arabidopsis thaliana
841 - - - - - - - - - - - - - - - - - - - - - - - K S   c.elegans kinase
337 - - - - - - - - - - - - - - - - - - - - - - - - A   D.discoideum (A35670)
422                                                     D.Discoideum (U01064)
927 Q P T L L D M D M E G Q N Q D S T V P L C G A H G S H   H.sapiens (Z48615)
927 Q P T L L D M D M E G Q N Q D S T V P L C G A H G S H   Homo sapiens (Z48615)
648                                                     Human raf1 (W13107)
648                                                     Human Raf1kinase (R98215)
462 - - - - - - - - - - - - - - - - - - - - - - - - T   Soybean kinase (M67449)
```

Fig. 3 cont.

```
Protein Family / Domain Matches, HMMer version 2

Searching for complete domains
hmmpfam - search a single seq against HMM database
HMMER 2.1.1 (Dec 1998)
Copyright (C) 1992-1998 Washington University School of Medicine
HMMER is freely distributed under the GNU General Public License (GPL).
------------------------------------------------
HMM file:                 /prod/ddm/seqanal/PFAM/pfam3.4/Pfam
Sequence file:            /tmp/orfanal.13255.aa
------------------------------------------------
 Query: sequence13252

Scores for sequence family classification (score includes all domains):
Model      Description                                      Score    E-value   N
-----      -----------                                      -----    -------  ---
ank        PF00023 Ank repeat                               207.5     2e-58    9
pkinase    PF00069 Eukaryotic protein kinase domain         201.9   9.9e-57    1

Parsed for domains:
Model      Domain   seq-f  seq-t    hmm-f hmm-t      score   E-value
-------    -------  -----  -----    ----- -----      -----   -------
ank        1/9       66     99..      1    33 []      3.2       12
ank        2/9      100    132..      1    33 []     34.0    3.4e-06
ank        3/9      133    165..      1    33 []     44.5    2.4e-09
ank        4/9      168    198..      1    33 []     34.6    2.3e-06
ank        5/9      199    233..      1    33 []     28.1    0.00021
ank        6/9      234    268..      1    33 []     15.4       0.28
ank        7/9      269    302..      1    33 []     20.6      0.037
ank        8/9      306    338..      1    33 []      3.3       11
ank        9/9      339    371..      1    33 []     35.4    1.3e-06
pkinase    1/1      463    716..      1   273 [.    201.9    9.9e-57

Alignments of top-scoring domains:
ank: domain 1 of 9, from 66 to 99: score 3.2, E = 12
                   *->nGnTPLHlAaryg.nvevvklLLehGAdvnartk<-*
                      nG++ LH1+++ g++ + ++ L+ +G + t+
     sequence13     66 NGLSLLHLCCICGgKKSHIRTLMLKGLRPSRLTR      99 ank: domain 2 of 9, from 100 to 132: score 34.0, E = 3.4e-06
                   *->nGnTPLHlAarygnvevvklLLehGAdvnartk<-*
                      nG+T+LH1A++++n e++ LL GAd+   + +
     sequence13    100 NGFTALHLAVYKDNAELITSLLHSGADIQQVGY     132 ank: domain 3 of 9, from 133 to 165: score 44.5, E = 2.4e-09
                   *->nGnTPLHlAarygnvevvklLLehGAdvnartk<-*
                      G+T+LH+A ++g++e +++LL+hGA+vn+++
     sequence13    133 GGLTALHIATIAGHLEAADVLLQHGANVNIQDA     165 ank: domain 4 of 9, from 168 to 198: score 34.6, E = 2.3e-06
                   *->nGnTPLHlAarygnvevvklLLehGAdvnartk<-*
                      +TPLH+Aa+yg+ +v +lLL+ GAdvn+  +
     sequence13    168 --FTPLHIAAYYGHEQVTRLLLKFGADVNVSGE     198 ank: domain 5 of 9, from 199 to 233: score 28.1, E = 0.00021
                   *->nGnTPLHlAarygnvevvklLLe..hGAdvnartk<-*
                      G+ PLH1A+ +g ++++klL+e++ Advna+++
     sequence13    199 VGDRPLHLASAKGFLNIAKLLMEegSKADVNAQDN     233
```

Fig. 4

```
ank: domain 6 of 9, from 234 to 268: score 15.4, E = 0.28
                 *->nGnTPLHlAarygnvevvklLLe..hGAdvnartk<-*
                    + PLH ++r g+ ++vk+LL+++     ++++++
  sequence13    234    EDHVPLHFCSRFGHHDIVKYLLQsdLEVQPHVVNI    268 ank: domain 7 of 9, from 269 to 302: score 20.6, E = 0.037
                 *->nGnTPLHlAarygnvevvklLLe.hGAdvnartk<-*
                    G+TPLHlA+++g+ ev+k  ++  G+    + +
  sequence13    269    YGDTPLHLACYNGKFEVAKEIIQiSGTESLTKEN    302 ank: domain 8 of 9, from 306 to 338: score 3.3, E = 11
                 *->nGnTPLHlAaryg.nvevvklLLe.hGAdvnartk<-*
                    T+ H A+ yg+++++vk+LL+++   ++n + +
  sequence13    306    --ETAFHSACTYGkSIDLVKFLLDqNVININHQGR    338 ank: domain 9 of 9, from 339 to 371: score 35.4, E = 1.3e-06
                 *->nGnTPLHlAarygnvevvklLLehGAdvnartk<-*
                    +G+T LH A+++g++++v++LL++GAd n +
  sequence13    339  DGHTGLHSACYHGHIRLVQFLLDNGADMNLVAC    371 pkinase: domain 1 of 1, from 463 to 716: score 201.9, E = 9.9e-57
                 *->yelleklGeGsfGkVykakhktgkivAvKilk......kesls..lr
                    +e++e++G+GsfGkVyk++ + +kivA+K  + ++  +k++++   r
  sequence13    463    IEFHEIIGSGSFGKVYKGRCR-NKIVAIKRYRantycsKSDVDmfCR 508

EiqilkrlsHpNIvrllgvfedtddhlylvmEymegGdLfdylrrng.pl
                    E++il +l+Hp ++++ g++ ++++ + +v++y  gG+Lf++l+++++ l
  sequence13    509 EVSILCQLNHPCVIQFVGACLNDPSQFAIVTQYISGGSLFSLLHEQKrIL 558 sekeakkialQilrGleYLHsng..ivHRDLKpeNILldengtvKiaDFG
                    + +  + ia ++++G+eYLH+   ++i+HRDL + NILl e+g+  +aDFG
  sequence13    559 DLQSKLIIAVDVAKGMEYLHNLTqpIIHRDLNSHNILLYEDGHAVVADFG 608

LArll.....eklttfvGTpwYmmAPEvileg.rgysskvDvWSlGviLy
                    +r+l++ ++ ++t  G +++m APEv  + + y+ k+Dv S+   L+
  sequence13    609 ESRFLqsldeDNMTKQPGNLRWM-APEV-FTQcTRYTIKADVFSYALCLW 656
                    ElltggplfpgadlpaftggdevdqliifvlklPfsdelpktridpleel
                    E+ltg                                  ++Pf +    +p ++
  sequence13    657 EILTG-----------------------EIPFAH------LKPAAAA 674 frikkr..rlplpsncSeelkdLlkkcLnkDPskRpGsatakeil<-*
                    ++ +++ r+p+ ++++++ +L1 + +n P+ Rp  + e++
  sequence13    675 ADMAYHhiRPPIGYSIPKPISSLLIRGWNACPEGRP---EFSEVV    716
```

Fig. 4 cont.

CARK PROTEIN AND NUCLEIC ACID MOLECULES AND USES THEREFOR

RELATED APPLICATIONS

This application claims priority to U.S. provisional Application No. 60/111,938, filed on Dec. 11, 1998, incorporated herein in its entirety by this reference.

BACKGROUND OF THE INVENTION

Phosphate tightly associated with protein has been known since the late nineteenth century. Since then, a variety of covalent linkages of phosphate to proteins have been found. The most common involve esterification of phosphate to serine, threonine, and tyrosine with smaller amounts being linked to lysine, arginine, histidine, aspartic acid, glutamic acid, and cysteine. The occurrence of phosphorylated proteins implies the existence of one or more protein kinases capable of phosphorylating amino acid residues on proteins, and also of protein phosphatases capable of hydrolyzing phosphorylated amino acid residues on proteins.

Protein kinases play critical roles in the regulation of biochemical and morphological changes associated with cellular growth and division (D'Urso, G. et al. (1990) *Science* 250: 786–791; Birchmeier. C. et al. (1993) *Bioessays* 15: 185–189). They serve as growth factor receptors and signal transducers and have been implicated in cellular transformation and malignancy (Hunter, T. et al. (1992) *Cell* 70: 375–387; Posada, J. et al. (1992) *Mol. Biol. Cell* 3: 583–592; Hunter, T. et al. (1994) *Cell* 79: 573–582). For example, protein kinases have been shown to participate in the transmission of signals from growth-factor receptors (Sturgill, T. W. et al. (1988) *Nature* 344: 715–718; Gomez, N. et al. (1991) *Nature* 353: 170–173), control of entry of cells into mitosis (Nurse, P. (1990) Nature 344: 503–508; Maller, J. L. (1991) *Curr. Opin. Cell Biol.* 3: 269–275) and regulation of actin bundling (Husain-Chishti, A. et al. (1988) *Nature* 334: 718–721). Protein kinases can be divided into two main groups based on either amino acid sequence similarity or specificity for either serine/threonine or tyrosine residues. A small number of dual-specificity kinases are structurally like the serine/threonine-specific group. Within the broad classification, kinases can be further subdivided into families whose members share a higher degree of catalytic domain amino acid sequence identity and also have similar biochemical properties. Most protein kinase family members also share structural features outside the kinase domain that reflect their particular cellular roles. These include regulatory domains that control kinase activity or interaction with other proteins (Hanks, S. K. et al. (1988) *Science* 241: 42–52). For example, kinases which contain ankyrin repeat domains have been identified, such as the Integrin-linked kinase (ILK).

ILK is an ankyrin repeat containing serine-threonine protein kinase which interacts with integrin $\beta_1$ and $\beta_3$ heterodimeric transmembrane glycoprotein subunit cytoplasmic domains. Integrins communicate with cell surface and cytoplasmic molecules such as cytoskeletal and catalytic signaling proteins (Hannigan G. E. et al. (1981) *Nature* 379:91–96, Schwartz M. A. et al. (1995) *Annu. Rev. Cell Dev. Biol.* 11:549–599). Overexpression of ILK increases the expression of cyclin A, cyclin $D_1$ and Cdk4 proteins by overriding the adhesion-dependent regulation of cell cycle progression through $G_1$ into S phase. This activity suggests that ILK may be an important regulator of integrin-mediated cell cycle progression (Radeva G. et al. (1997) *J. Biol. Chem.* 272:13937–13944). Overexpression of ILK also stimulates fibronectin matrix assembly in epithelial cells (Wu C. et al. (1998) *J. Biol. Chem.* 273:528–536).

SUMMARY OF THE INVENTION

The present invention is based, at least in part, on the discovery of novel ankyrin repeat containing kinases, referred herein as "Cardiac-related Ankyrin-Repeat Protein Kinase" ("CARK") nucleic acid and protein molecules. The CARK molecules of the present invention are useful as modulating agents for regulating a variety of cellular processes, e.g., cardiac cellular processes. Accordingly, in one aspect, this invention provides isolated nucleic acid molecules encoding CARK proteins or biologically active portions thereof, as well as nucleic acid fragments suitable as primers or hybridization probes for the detection of CARK-encoding nucleic acids.

In one embodiment, a CARK nucleic acid molecule of the invention is at least 50%, 55%, 60%, 65%, 70%, 75%, 80%, 85%, 90%, 95%, 98%, or more identical to the nucleotide sequence (e.g., to the entire length of the nucleotide sequence) shown in SEQ ID NO:1 or 3 or the nucleotide sequence of the DNA insert of the plasmid deposited with ATCC as Accession Number PTA-1530, or a complement thereof.

In a preferred embodiment, the isolated nucleic acid molecule includes the nucleotide sequence shown SEQ ID NO:1 or 3, or a complement thereof. In another embodiment, the nucleic acid molecule includes SEQ ID NO:3 and nucleotides 1–47 of SEQ ID NO:1. In another embodiment, the nucleic acid molecule includes SEQ ID NO:3 and nucleotides 2553–3025 of SEQ ID NO:1. In another preferred embodiment, the nucleic acid molecule consists of the nucleotide sequence shown in SEQ ID NO:1 or 3. In another preferred embodiment, the nucleic acid molecule includes a fragment of at least 467 nucleotides (e.g., 467 contiguous nucleotides) of the nucleotide sequence of SEQ ID NO:1 or 3, or a complement thereof.

In another embodiment, a CARK nucleic acid molecule includes a nucleotide sequence encoding a protein having an amino acid sequence sufficiently homologous to the amino acid sequence of SEQ ID NO:2 or an amino acid sequence encoded by the DNA insert of the plasmid deposited with ATCC as Accession Number PTA-1530. In a preferred embodiment, a CARK nucleic acid molecule includes a nucleotide sequence encoding a protein having an amino acid sequence at least 50%, 55%, 60%, 65%, 70%, 75%, 80%, 85%, 90%, 95%, 98% or more homologous to the entire length of the amino acid sequence of SEQ ID NO:2 or the amino acid sequence encoded by the DNA insert of the plasmid deposited with ATCC as Accession Number PTA-1530.

In another preferred embodiment, an isolated nucleic acid molecule encodes the amino acid sequence of human CARK. In yet another preferred embodiment, the nucleic acid molecule includes a nucleotide sequence encoding a protein having the amino acid sequence of SEQ ID NO:2 or the amino acid sequence encoded by the DNA insert of the plasmid deposited with ATCC as Accession Number PTA-1530. In yet another preferred embodiment, the nucleic acid molecule is at least 467 nucleotides in length. In a further preferred embodiment, the nucleic acid molecule is at least 467 nucleotides in length an d encodes a protein having a CARK activity (as described herein).

Another embodiment of the invention features nucleic acid molecules, preferably CARK nucleic acid molecules, which specifically detect CARK nucleic acid molecules relative to nucleic acid molecules encoding non-CARK proteins. For example, in one embodiment, such a nucleic acid molecule is at least 250–300, 300–350, 350–400, 400–450, 467, 467–500, 500–550, or 550–600 or more nucleotides in length and hybridizes under stringent conditions to a nucleic acid molecule comprising the nucleotide sequence shown in SEQ ID NO:1 or 3, the nucleotide sequence of the DNA insert of the plasmid deposited with ATCC as Accession Number PTA-1530, or a complement thereof.

In preferred embodiments, the nucleic acid molecules are at least 15 (e.g., contiguous) nucleotides in length and hybridize under stringent conditions to nucleotides 1–47, 94–294, 318–338, 1145–1364, 1833–1921, 2051–2267, 2290–2543, or 3018–3025 of SEQ ID NO:1. In other preferred embodiments, the nucleic acid molecules comprise nucleotides 1–47, 94–294, 318–338, 1145–1364, 1833–1921, 2051–2267, 2290–2543, or 3018–3025 of SEQ ID NO:1.

In other preferred embodiments, the nucleic acid molecule encodes a naturally occurring allelic variant of a polypeptide comprising the amino acid sequence of SEQ ID NO:2 or an amino acid sequence encoded by the DNA insert of the plasmid deposited with ATCC as Accession Number PTA-1530, wherein the nucleic acid molecule hybridizes to a nucleic acid molecule comprising SEQ ID NO:1 or 3 under stringent conditions.

Another embodiment of the invention provides an isolated nucleic acid molecule which is antisense to a CARK nucleic acid molecule, e.g., the coding strand of a CARK nucleic acid molecule.

Another aspect of the invention provides a vector comprising a CARK nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably a CARK protein, by culturing in a suitable medium, a host cell, e.g., a mammalian host cell such as a non-human mammalian cell, of the invention containing a recombinant expression vector, such that the protein is produced.

Another aspect of this invention features isolated or recombinant CARK proteins and polypeptides. In one embodiment, the isolated protein, preferably a CARK protein, includes at least one ankyrin repeat domain and preferably two, three, four, five, six, seven, eight, or, most preferably, nine ankyrin repeat domains. In another embodiment, the isolated protein, preferably a CARK protein, includes a protein kinase domain. In a preferred embodiment, the protein, preferably a CARK protein, includes at least one ankyrin repeat domain and preferably two, three, four, five, six, seven, eight, or, most preferably, nine ankyrin repeat domains, and has an amino acid sequence at least about 50%, 55%, 60%, 65%, 70%, 75%, 80%, 85%, 90%, 95%, 98% or more homologous to the amino acid sequence of SEQ ID NO:2 or the amino acid sequence encoded by the DNA insert of the plasmid deposited with ATCC as Accession Number PTA-1530. In another preferred embodiment, the protein, preferably a CARK protein, includes a protein kinase domain and has an amino acid sequence at least about 50%, 55%, 60%, 65%, 70%, 75%, 80%, 85%, 90%, 95%, 98% or more homologous to the amino acid sequence of SEQ ID NO:2 or the amino acid sequence encoded by the DNA insert of the plasmid deposited with ATCC as Accession Number PTA-1530. In yet another preferred embodiment, the protein, preferably a CARK protein, includes at least one ankyrin repeat domain and preferably two, three, four, five, six, seven, eight, or, most preferably, nine ankyrin repeat domains, a protein kinase domain, and has an amino acid sequence at least about 50%, 55%, 60%, 65%, 70%, 75%, 80%, 85%, 90%, 95%, 98% or more homologous to the amino acid sequence of SEQ ID NO:2 or the amino acid sequence encoded by the DNA insert of the plasmid deposited with ATCC as Accession Number PTA-1530.

In another preferred embodiment, the protein, preferably a CARK protein, includes at least one ankyrin repeat domain and preferably two, three, four, five, six, seven, eight, or, most preferably, nine ankyrin repeat domains and has a CARK activity, as described herein. In yet another preferred embodiment, the protein, preferably a CARK protein, includes a protein kinase domain and has a CARK activity, as described herein. In a further preferred embodiment, the protein, preferably a CARK protein, includes at least one ankyrin repeat domain and preferably two, three, four, five, six, seven, eight, or, most preferably, nine ankyrin repeat domains, a protein kinase domain, and has a CARK activity, as described herein.

In yet another preferred embodiment, the protein, preferably a CARK protein, includes at least one ankyrin repeat domain and preferably two, three, four, five, six, seven, eight, or, most preferably, nine ankyrin repeat domains and is encoded by a nucleic acid molecule having a nucleotide sequence which hybridizes under stringent hybridization conditions to a nucleic acid molecule comprising the nucleotide sequence of SEQ ID NO:1 or 3. In a further embodiment, the protein, preferably a CARK protein, includes a protein kinase domain and is encoded by a nucleic acid molecule having a nucleotide sequence which hybridizes under stringent hybridization conditions to a nucleic acid molecule comprising the nucleotide sequence of SEQ ID NO:1 or 3. In another preferred embodiment, the protein, preferably a CARK protein, includes at least one ankyrin repeat domain and preferably two, three, four, five, six, seven, eight, or, most preferably, nine ankyrin repeat domains, a protein kinase domain, and is encoded by a nucleic acid molecule having a nucleotide sequence which hybridizes under stringent hybridization conditions to a nucleic acid molecule comprising the nucleotide sequence of SEQ ID NO:1 or 3.

In another embodiment, the invention features fragments of the protein having the amino acid sequence of SEQ ID NO:2, wherein the fragment comprises at least 15 amino acids (e.g., contiguous amino acids) of the amino acid sequence of SEQ ID NO:2 or an amino acid sequence encoded by the DNA insert of the plasmid deposited with the ATCC as Accession Number PTA-1530. In another embodiment, the protein, preferably a CARK protein, has the amino acid sequence of SEQ ID NO:2, respectively.

In another embodiment, the invention features an isolated protein, preferably a CARK protein, which is encoded by a nucleic acid molecule consisting of a nucleotide sequence at least about 50%, 55%, 60%, 65%, 70%, 75%, 80%, 85%, 90%, 95%, 98% or more homologous to a nucleotide sequence of SEQ ID NO:1 or 3, or a complement thereof.

This invention further features an isolated protein, preferably a CARK protein, which is encoded by a nucleic acid molecule consisting of a nucleotide sequence which hybridizes under stringent hybridization conditions to a nucleic acid molecule comprising the nucleotide sequence of SEQ ID NO:1 or 3, or a complement thereof.

The proteins of the present invention or portions thereof, e.g., biologically active portions thereof, can be operatively linked to a non-CARK polypeptide (e.g., heterologous amino acid sequences) to form fusion proteins. The invention further features antibodies, such as monoclonal or polyclonal antibodies, that specifically bind proteins of the invention, preferably CARK proteins. In addition, the CARK proteins or biologically active portions thereof can be incorporated into pharmaceutical compositions, which optionally include pharmaceutically acceptable carriers.

In another aspect, the present invention provides a method for detecting the presence of a CARK nucleic acid molecule, protein or polypeptide in a biological sample by contacting the biological sample with an agent capable of detecting a CARK nucleic acid molecule, protein or polypeptide such that the presence of a CARK nucleic acid molecule, protein or polypeptide is detected in the biological sample.

In another aspect, the present invention provides a method for detecting the presence of CARK activity in a biological sample by contacting the biological sample with an agent capable of detecting an indicator of CARK activity such that the presence of CARK activity is detected in the biological sample.

In another aspect, the invention provides a method for modulating CARK activity comprising contacting a cell capable of expressing CARK with an agent that modulates CARK activity such that CARK activity in the cell is modulated. In one embodiment, the agent inhibits CARK activity. In another embodiment, the agent stimulates CARK activity.

In one embodiment, the agent is an antibody that specifically binds to a CARK protein. In another embodiment, the agent modulates expression of CARK by modulating transcription of a CARK gene or translation of a CARK mRNA. In yet another embodiment, the agent is a nucleic acid molecule having a nucleotide sequence that is antisense to the coding strand of a CARK mRNA or a CARK gene.

In one embodiment, the methods of the present invention are used to treat a subject having a disorder characterized by aberrant or unwanted CARK protein or nucleic acid expression or activity by administering an agent which is a CARK modulator to the subject.

In one embodiment, the CARK modulator is a CARK protein. In another embodiment the CARK modulator is a CARK nucleic acid molecule. In yet another embodiment, the CARK modulator is a peptide, peptidomimetic, or other small molecule. In a preferred embodiment, the disorder characterized by aberrant or unwanted CARK protein or nucleic acid expression is a cardiovascular disorder.

The present invention also provides a diagnostic assay for identifying the presence or absence of a genetic alteration characterized by at least one of (i) aberrant modification or mutation of a gene encoding a CARK protein; (ii) misregulation of the gene; and (iii) aberrant post-translational modification of a CARK protein, wherein a wild-type form of the gene encodes a protein with a CARK activity.

In another aspect the invention provides a method for identifying a compound that binds to or modulates the activity of a CARK protein, by providing an indicator composition comprising a CARK protein having CARK activity, contacting the indicator composition with a test compound, and determining the effect of the test compound on CARK activity in the indicator composition to identify a compound that modulates the activity of a CARK protein.

Other features and advantages of the invention will be apparent from the following detailed description and claims.

BRIEF DESCRIPTION OF THE DRAWINGS

FIG. 1 depicts the cDNA sequence and predicted amino acid sequence of human CARK. The nucleotide sequence corresponds to nucleic acids 1 to 3025 of SEQ ID NO:1. The amino acid sequence corresponds to amino acids 1 to 835 of SEQ ID NO:2. The coding region without the 5' and 3' untranslated regions of the human CARK gene is shown in SEQ ID NO:3.

FIG. 3 depicts an alignment of the CARK protein with the A. Thaliana kinase 2 (Accession No. Z97337), A. Thaliana kinase 3 (Accession No. AC003113), Arabidopsis thaliana (Accession No. AL031135), C. elegans kinase (Accession No. AF024491), D. discoideum protein tyrosine kinase (Accession No. A35670), D. discoideum protein tyrosine kinase (Accession No. U01064), H. sapiens serine/threonine kinase (Accession No. Z48615), human raf1 (Accession No. W13107), human Raf1 kinase (Accession No. R98215), and soybean kinase (Accession No. M67449) using the Clustal method with a PAM250 residue weight table.

FIG. 4 depicts the results of a search which was performed against the HMM database and which resulted in the identification of nine ankyrin repeat domains and a protein kinase domain in the human CARK protein.

DETAILED DESCRIPTION OF THE INVENTION

Figure 2:
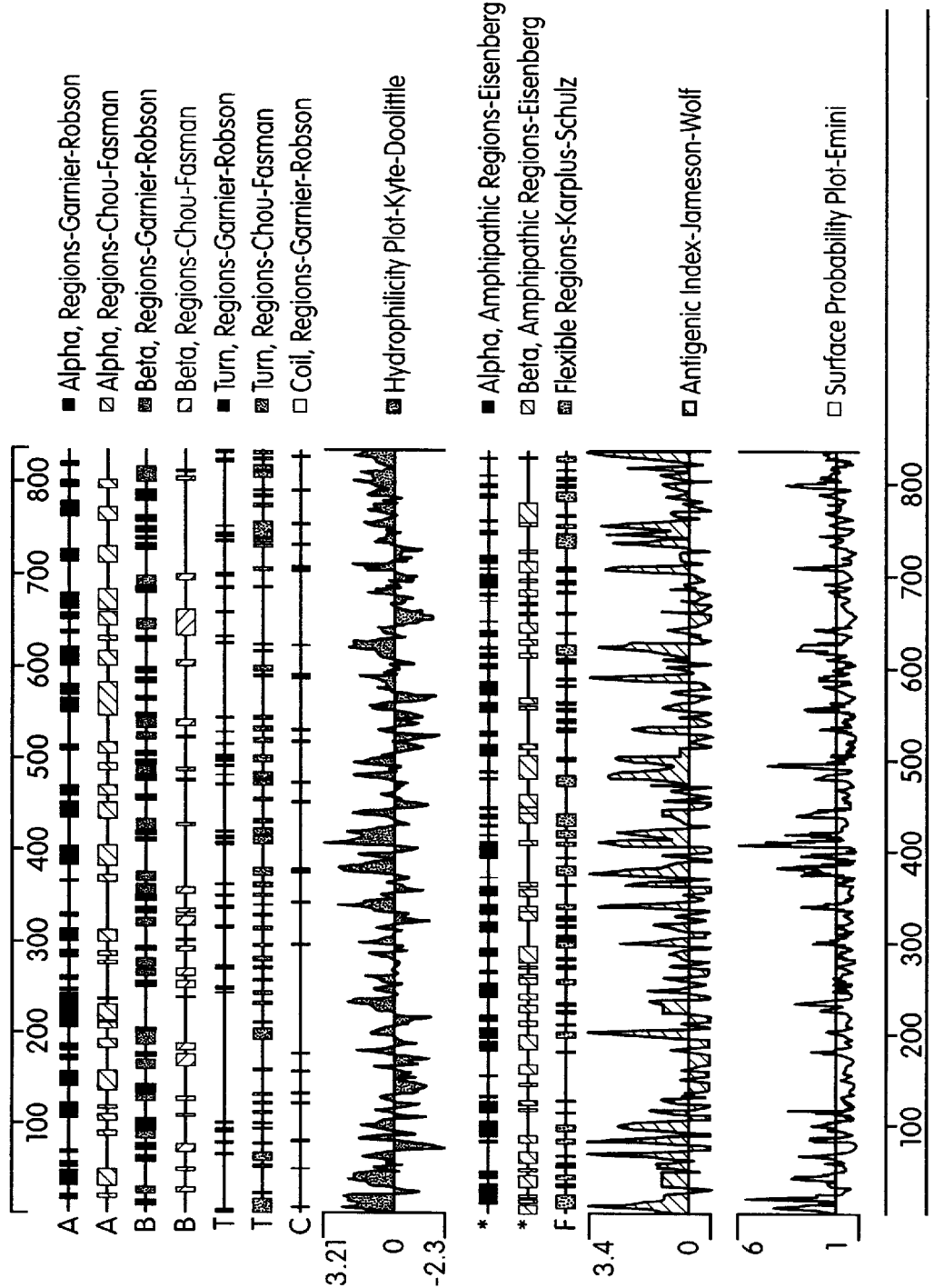
FIG. 2 depicts a structural, hydrophobicity, and antigenicity analysis of the human CARK protein.

The present invention is based, at least in part, on the discovery of novel molecules, referred to herein as "Cardiac-related Ankyrin-Repeat Protein Kinase" or "CARK" nucleic acid and protein molecules, which play a role in or finction in signalling pathways associated with cellular growth or differentiation. In one embodiment, the CARK molecules modulate the activity of one or more proteins involved in cellular growth or differentiation, e.g., cardiac cell growth or differentiation. In another embodiment, the CARK molecules of the present invention are capable of modulating the phosphorylation state of a CARK molecule or one or more proteins involved in cellular growth or differentiation, e.g., cardiac cell growth or differentiation.

In a preferred embodiment, the CARK molecules are protein kinases, e.g., serine/threonine protein kinases, which are expressed and/or finction in cells of the cardiovascular system, e.g., cells of the heart, the blood vessels, and/or the blood.

As used herein, the term "protein kinase" includes a protein or polypeptide which is capable of modulating its own phosphorylation state or the phosphorylation state of another protein or polypeptide. Protein kinases (described in, for example, Hanks S. K. et al. (1995) FASEB J. 9:576–596) can have a specificity for (i.e., a specificity to phosphorylate) serine/threonine residues, tyrosine residues, or both serine/threonine and tyrosine residues, e.g., the dual specificity kinases. There are a number of conserved regions in the catalytic domain of protein kinases. One of these regions, located in the N-terminal extremity of the catalytic domain, is a glycine-rich stretch of residues in the vicinity of a lysine residue, which is believed to be involved in ATP binding. Another region, located in the central part of the catalytic domain, contains a conserved aspartic acid residue which is important for the catalytic activity of the enzyme (Knighton D. R. et al. (1991) Science 253:407–414). Two signature patterns have been described for this region: one specific for serine/ threonine kinases and one for tyrosine kinases. Protein kinase polypeptides of the present invention preferably include one of the following consensus sequences:

[LIV]-G- {P}-G-{P}-[FYWMGSTNH]-[SGA]-{PW}-[LIVCAT]-{PD}-x [GSTACLIVMFY]-x(5, 18)-[LIVMFYWCSTAR]-[AIVP]-[LIVMFAGCKR]-K (SEQ ID NO:4)

[K binds ATP]

[LIVMFYC]-x-[HY]-x-D-[LIVMFY]-K-x(2)-N-[LIVMFYCT](3) (SEQ ID NO:5)

[D is an active site residue]

[LIVMFYC]-x-[HY]-x-D-[LIVMFY]-[RSTAC]-x(2)-N-[LIVMFYC](3) (SEQ ID NO:6)

[D is an active site residue]

Protein kinases play a role in signalling pathways associated with cellular growth and differentiation. For example, protein kinases are involved in the regulation of signal transmission from cellular receptors, e.g., growth-factor receptors; entry of cells into mitosis; and the regulation of cytoskeleton function, e.g., actin bundling. Thus, the CARK molecules of the present invention may be involved in: 1) the regulation of transmission of signals from cellular receptors, e.g., cardiac cell growth factor receptors; 2) the modulation of the entry of cells, e.g., cardiac precursor cells, into mitosis; 3) the modulation of cellular differentiation; 4) the modulation of cell death; and 5) the regulation of cytoskeleton function, e.g., actin bundling.

Inhibition or over stimulation of the activity of protein kinases involved in signaling pathways associated with cellular growth can lead to perturbed cellular growth, which can in turn lead to cellular growth related disorders. As used herein, a "cellular growth related disorder" includes a disorder, disease, or condition characterized by a deregulation, e.g., an upregulation or a downregulation, of cellular growth. Cellular growth deregulation may be due to a deregulation of cellular proliferation, cell cycle progression, cellular differentiation and/or cellular hypertrophy. Examples of cellular growth related disorders include cardiovascular disorders such as heart failure, hypertension, atrial fibrillation, dilated cardiomyopathy, idiopathic cardiomyopathy, or angina; proliferative disorders or differentiative disorders such as cancer, e.g., melanoma, prostate cancer, cervical cancer, breast cancer, colon cancer, or sarcoma.

As used herein, the term "cardiovascular disorder" includes a disease, disorder, or state involving the cardiovascular system, e.g., the heart, the blood vessels, and/or the blood.

A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, coronary artery disease, valvular disease, arrhythmias, and cardiomyopathies.

As used herein, the term "congestive heart failure" includes a condition characterized by a diminished capacity of the heart to supply the oxygen demands of the body. Symptoms and signs of congestive heart failure include diminished blood flow to the various tissues of the body, accumulation of excess blood in the various organs, e.g., when the heart is unable to pump out the blood returned to it by the great veins, exertional dyspnea, fatigue, and/or peripheral edema, e.g., peripheral edema resulting from left ventricular dysfunction.

Congestive heart failure may be acute or chronic. The manifestation of congestive heart failure usually occurs secondary to a variety of cardiac or systemic disorders that share a temporal or permanent loss of cardiac function. Examples of such disorders include hypertension, coronary artery disease, valvular disease, and cardiomyopathies, e.g., hypertrophic, dilative, or restrictive cardiomyopathies. Congestive heart failure is described in, for example, Cohn J. N. et al. (1998) *American Family Physician* 57:1901–04, the contents of which are incorporated herein by reference.

The present invention is based, at least in part, on the discovery of novel molecules, referred to herein as CARK protein and nucleic acid molecules, which comprise a family of molecules having certain conserved structural and functional features.

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

For example, the family of CARK proteins comprise at least one, and preferably two, three, four, five, six, seven, eight, or most preferably, nine ankyrin repeat domains. As used herein, the term "ankyrin repeat domain" includes a protein domain involved in protein:protein interactions, having an amino acid sequence of about 20–40 amino acid residues and having a bit score for the alignment of the sequence to the ankyrin repeat domain (HMM) of at least 3. Preferably, an ankyrin repeat domain includes at least about 25–40, more preferably about 25–35 amino acid residues, or most preferably about 30–35 amino acids and has a bit score for the alignment of the sequence to the ankyrin repeat domain (HMM) of at least 5, 10, 20, 30, 40, 50, or greater. The ankyrin repeat domain (HMM) has been assigned the PFAM Accession PF00023 (http://genome.wustl.edu/Pfam/.html). Ankyrin repeats are described in, for example, Otto E. et al. (1991) *J. Biol. Chem.* 114:241–253, Hatada E. N. et al. (1992) *PNAS USA* 89:2489–2493, and Blank V. P. et al. (1992) *Trends Genet.* 8:144–149, the contents of which are incorporated herein by reference.

To identify the presence of an ankyrin repeat domain in a CARK protein, and make the determination that a protein of interest has a particular profile, the amino acid sequence of the protein is searched against a database of HMMs (e.g., the Pfam database, release 2.1) using the default parameters (http://www.sanger.ac.uk/Software/Pfam/HMM_search). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3)405–420 and a detailed description of HMMs can be found, for example, in Gribskov et al.(1990) *Meth. Enzymol.* 183:146–159; Gribskov et al.(1987) *Proc. Natl. Acad. Sci. USA* 84:4355–4358; Krogh et al.(1994) *J. Mol.*

Biol. 235:1501–1531; and Stultz et al.(1993) *Protein Sci.* 2:305–314, the contents of which are incorporated herein by reference. A search was performed against the HMM database resulting in the identification of nine ankyrin repeat domains in the amino acid sequence of human CARK (SEQ ID NO:2) at about residues 66–99, 100–132, 133–165, 168–198, 199–233, 234–268, 269–302, 306–338, and 339–371 of SEQ ID NO:2. The results of the search are set forth in FIG. 4.

In a further preferred embodiment, an ankyrin repeat domain includes at least about 25–40, more preferably about 25–35 amino acid residues, or about 30–35 amino acids and has at least 50–60% homology, preferably about 60–70%, more preferably about 70–80%, or about 80–90% homology with an ankyrin repeat domain of human CARK (e.g., residues 66– 99, 100–132, 133–165, 168–198, 199–233, 234–268, 269–302, 306–338, and 339–371 of SEQ ID NO:2).

In another embodiment, a CARK of the present invention is identified based on the presence of a "protein kinase domain" in the protein or corresponding nucleic acid molecule. As used herein, the term "protein kinase domain" includes a protein domain having an amino acid sequence of about 200–400 amino acid residues and having a bit score for the alignment of the sequence to the protein kinase domain (HMM) of at least 200. Preferably, a protein kinase domain includes at least about 200–300, and more preferably about 250–300 amino acid residues, and has a bit score for the alignment of the sequence to the protein kinase domain (HMM) of at least 210, 220, 230, 250, 300 or greater. The protein kinase domain (HMM) has been assigned the PFAM Accession PF00069 (http://genome.wustl.edu/Pfam/.html).

To identify the presence of a protein kinase domain in a CARK protein, and make the determination that a protein of interest has a particular profile, the amino acid sequence of the protein is searched against a database of HMMs as described above. A search was performed against the HMM database resulting in the identification of a protein kinase domain in the amino acid sequence of human CARK (SEQ ID NO:2) at about residues 463–716 of SEQ ID NO:2. The results of the search are set forth in FIG. 4.

In another preferred embodiment, a protein kinase domain includes at least about 200–400, more preferably about 200–300 amino acid residues, or about 250–300 amino acids and has at least 50–60% homology, preferably about 60–70%, more preferably about 70–80%, or about 80–90% homology with a protein kinase domain of human CARK (e.g., residues 463–716 of SEQ ID NO:2).

Accordingly, CARK proteins having at least 50–60% homology, preferably about 60–70%, more preferably about 70–80%, or about 80–90% homology with an ankyrin repeat domain or a protein kinase domain of human CARK are within the scope of the invention.

Isolated proteins of the present invention, preferably CARK proteins, have an amino acid sequence sufficiently homologous to the amino acid sequence of SEQ ID NO:2 or are encoded by a nucleotide sequence sufficiently homologous to SEQ ID NO:1 or 3. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%–80%, and even more preferably 90–95% homology across the amino acid sequences of the domains and contain at least one and preferably two structural domains or motifs, are defined herein as sufficiently homologous. Furthermore, amino acid or nucleotide sequences which share at least 30%, 40%, or 50%, preferably 60%, more preferably 70–80%, or 90–95% homology and share a common functional activity are defined herein as sufficiently homologous.

As used interchangeably herein, a "CARK activity", "biological activity of CARK" or "functional activity of CARK", refers to an activity exerted by a CARK protein, polypeptide or nucleic acid molecule on a CARK responsive cell or on a CARK protein substrate, as determined in vivo, or in vitro, according to standard techniques. In one embodiment, a CARK activity is a direct activity, such as an association with a CARK-traget molecule. As used herein, a "target molecule" or "binding partner" is a molecule with which a CARK protein binds or interacts in nature, such that CARK-mediated function is achieved. A CARK target molecule can be a non-CARK molecule or a CARK protein or polypeptide of the present invention. In an exemplary embodiment, a CARK target molecule is a CARK ligand. Alternatively, a CARK activity is an indirect activity, such as a cellular signaling activity mediated by interaction of the CARK protein with a CARK ligand. The biological activity of CARK is described herein.

Accordingly, another embodiment of the invention features isolated CARK proteins and polypeptides having a CARK activity. Preferred proteins are CARK proteins having at least one ankyrin repeat domain and preferably two, three, four, five, six, seven, eight, or, most preferably, nine ankyrin repeat domains, and, preferably, a CARK activity. Other preferred proteins are CARK proteins having a protein kinase domain and, preferably, a CARK activity. Yet other preferred proteins have at least one ankyrin repeat domain and preferably two, three, four, five, six, seven, eight, or, most preferably, nine ankyrin repeat domains, a protein kinase domain, and, preferably, a CARK activity. Additional preferred proteins have at least one ankyrin repeat domain and preferably two, three, four, five, six, seven, eight, or, most preferably, nine ankyrin repeat domains, a protein kinase domain, and are, preferably, encoded by a nucleic acid molecule having a nucleotide sequence which hybridizes under stringent hybridization conditions to a nucleic acid molecule comprising the nucleotide sequence of SEQ ID NO:1 or 3.

The nucleotide sequence of the isolated human CARK cDNA and the predicted amino acid sequence of the human CARK polypeptide are shown in FIG. 1 and in SEQ ID NOs: 1 and 2, respectively. A plasmid containing the nucleotide sequence encoding human CARK was deposited with the American Type Culture Collection (ATCC), 10801 University Boulevard, Manassas, Va. 20110-2209, on Mar. 21, 2000 and assigned Accession Number PTA-1530. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. § 112.

The human CARK gene, which is approximately 3025 nucleotides in length, encodes a protein having a molecular weight of approximately 96 kD and which is approximately 835 amino acid residues in length.

Various aspects of the invention are described in further detail in the following subsections:

I. Isolated Nucleic Acid Molecules

One aspect of the invention pertains to isolated nucleic acid molecules that encode CARK proteins or biologically active portions thereof, as well as nucleic acid fragments sufficient for use as hybridization probes to identify CARK-encoding nucleic acid molecules (e.g., CARK mRNA) and fragments for use as PCR primers for the amplification or mutation of CARK nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated CARK nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1 or 3,or the nucleotide sequence of the DNA insert of the plasmid deposited with ATCC as Accession Number PTA-1530, or a portion thereof, can be isolated using standard molecular biology techniques and the sequence information provided herein. Using all or portion of the nucleic acid sequence of SEQ ID NO:1 or 3, or the nucleotide sequence of the DNA insert of the plasmid deposited with ATCC as Accession Number PTA-1530, as a hybridization probe, CARK nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:1 or 3, or the nucleotide sequence of the DNA insert of the plasmid deposited with ATCC as Accession Number PTA-1530 can be isolated by the polymerase chain reaction (PCR) using synthetic oligonucleotide primers designed based upon the sequence of SEQ ID NO:1 or 3, or the nucleotide sequence of the DNA insert of the plasmid deposited with ATCC as Accession Number PTA-1530.

A nucleic acid of the invention can be amplified using CDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to CARK nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1 corresponds to the human CARK cDNA. This cDNA comprises sequences encoding the human CARK protein (i.e., "the coding region", from nucleotides 48–2552), as well as 5' untranslated sequences (nucleotides 1–47) and 3' untranslated sequences (nucleotides 2553–3025). Alternatively, the nucleic acid molecule can comprise only the coding region of SEQ ID NO:1 (e.g., nucleotides 48–2552, corresponding to SEQ ID NO:3).

In another preferred embodiment, an isolated nucleic acid molecule of the invention comprises a nucleic acid molecule which is a complement of the nucleotide sequence shown in SEQ ID NO:1 or 3, or the nucleotide sequence of the DNA insert of the plasmid deposited with ATCC as Accession Number PTA-1530, or a portion of any of these nucleotide sequences.

A nucleic acid molecule which is complementary to the nucleotide sequence shown in SEQ ID NO:1 or 3, or the nucleotide sequence of the DNA insert of the plasmid deposited with ATCC as Accession Number PTA-1530, is one which is sufficiently complementary to the nucleotide sequence shown in SEQ ID NO:1 or 3, or the nucleotide sequence of the DNA insert of the plasmid deposited with ATCC as Accession Number PTA-1530, such that it can hybridize to the nucleotide sequence shown in SEQ ID NO:1 or 3, or the nucleotide sequence of the DNA insert of the plasmid deposited with ATCC as Accession Number PTA-1530, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95%, 98% or more homologous to the entire length of the nucleotide sequence shown in SEQ ID NO:1 or 3, or the entire length of the nucleotide sequence of the DNA insert of the plasmid deposited with ATCC as Accession Number PTA-1530, or a portion of any of these nucleotide sequences.

Moreover, the nucleic acid molecule of the invention can comprise only a portion of the nucleic acid sequence of SEQ ID NO:1 or 3, or the nucleotide sequence of the DNA insert of the plasmid deposited with ATCC as Accession Number PTA-1530, for example, a fragment which can be used as a probe or primer or a fragment encoding a portion of a CARK protein, e.g., a biologically active portion of a CARK protein. The nucleotide sequence determined from the cloning of the CARK gene allows for the generation of probes and primers designed for use in identifying and/or cloning other CARK family members, as well as CARK homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1 or 3, or the nucleotide sequence of the DNA insert of the plasmid deposited with ATCC as Accession Number PTA-1530, of an anti-sense sequence of SEQ ID NO:1 or 3, or the nucleotide sequence of the DNA insert of the plasmid deposited with ATCC as Accession Number PTA-1530, or of a naturally occurring allelic variant or mutant of SEQ ID NO:1 or 3, or the nucleotide sequence of the DNA insert of the plasmid deposited with ATCC as Accession Number PTA-1530. In an exemplary embodiment, a nucleic acid molecule of the present invention comprises a nucleotide sequence which is greater than 250–300, 300–350, 350–400, 400–450, 467, 467–500, 500–550, 550–600, 600–650, 650–700, 700–750, 750–800, 800–850, 850–900, 900–950, 950–1000, or more nucleotides in length and hybridizes under stringent hybridization conditions to a nucleic acid molecule of SEQ ID NO:1 or 3, or the nucleotide sequence of the DNA insert of the plasmid deposited with ATCC as Accession Number PTA-1530.

Probes based on the CARK nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a CARK protein, such as by measuring a level of a CARK-encoding nucleic acid in a sample of cells from a subject e.g., detecting CARK mRNA levels or determining whether a genomic CARK gene has been mutated or deleted.

A nucleic acid fragment encoding a "biologically active portion of a CARK protein" can be prepared by isolating a portion of the nucleotide sequence of SEQ ID NO:1 or 3, or the nucleotide sequence of the DNA insert of the plasmid deposited with ATCC as Accession Number PTA-1530, which encodes a polypeptide having a CARK biological activity (the biological activities of the CARK proteins are described herein), expressing the encoded portion of the CARK protein (e.g., by recombinant expression in vitro) and assessing the activity of the encoded portion of the CARK protein.

The invention further encompasses nucleic acid molecules that differ from the nucleotide sequence shown in SEQ ID NO:1 or 3, or the nucleotide sequence of the DNA insert of the plasmid deposited with ATCC as Accession Number PTA-1530, due to degeneracy of the genetic code and thus encode the same CARK proteins as those encoded by the nucleotide sequence shown in SEQ ID NO:1 or 3, or the nucleotide sequence of the DNA insert of the plasmid deposited with ATCC as Accession Number PTA-1530. In another embodiment, an isolated nucleic acid molecule of the invention has a nucleotide sequence encoding a protein having an amino acid sequence shown in SEQ ID NO:2.

In addition to the CARK nucleotide sequences shown in SEQ ID NO:1 or 3, or the nucleotide sequence of the DNA insert of the plasmid deposited with ATCC as Accession Number PTA-1530, it will be appreciated by those skilled in the art that DNA sequence polymorphisms that lead to changes in the amino acid sequences of the CARK proteins may exist within a population (e.g., the human population). Such genetic polymorphism in the CARK genes may exist among individuals within a population due to natural allelic variation. As used herein, the terms "gene" and "recombinant gene" refer to nucleic acid molecules which include an open reading frame encoding a CARK protein, preferably a mammalia CARK protein, and can further include non-coding regulatory sequences, and introns.

Allelic variants of human CARK include both functional and non-functional CARK proteins. Functional allelic variants are naturally occurring amino acid sequence variants of the human CARK protein that maintain the ability to bind a CARK ligand and/or modulate cellular mechanisms associated with cell growth or differentiation. Functional allelic variants will typically contain only conservative substitution of one or more amino acids of SEQ ID NO:2 or substitution, deletion or insertion of non-critical residues in non-critical regions of the protein.

Non-functional allelic variants are naturally occurring amino acid sequence variants of the human CARK protein that do not have the ability to either bind a CARK ligand and/or modulate celular mechanisms associated with cell growth or differentiation. Non-functional allelic variants will typically contain a non-conservative substitution, a deletion, or insertion or premature truncation of the amino acid sequence of SEQ ID NO:2 or a substitution, insertion or deletion in critical residues or critical regions.

The present invention further provides non-human orthologues of the human CARK protein. Orthologues of the human CARK protein are proteins that are isolated from non-human organisms and possess the same CARK ligand binding and/or modulation of celular mechanisms associated with cell growth or differentiation of the human CARK protein. Orthologues of the human CARK protein can readily be identified as comprising an amino acid sequence that is substantially homologous to SEQ ID NO:2.

Moreover, nucleic acid molecules encoding other CARK family members and, thus, which have a nucleotide sequence which differs from the CARK sequences of SEQ ID NO:1 or 3, or the nucleotide sequence of the DNA insert of the plasmid deposited with ATCC as Accession Number PTA-1530 are intended to be within the scope of the invention. For example, another CARK cDNA can be identified based on the nucleotide sequence of human CARK. Moreover, nucleic acid molecules encoding CARK proteins from different species, and which, thus, have a nucleotide sequence which differs from the CARK sequences of SEQ ID NO:1 or 3, or the nucleotide sequence of the DNA insert of the plasmid deposited with ATCC as Accession Number PTA-1530 are intended to be within the scope of the invention. For example, a mouse CARK cDNA can be identified based on the nucleotide sequence of a human CARK.

Nucleic acid molecules corresponding to natural allelic variants and homologues of the CARK cDNAs of the invention can be isolated based on their homology to the CARK nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the CARK cDNAs of the invention can further be isolated by mapping to the same chromosome or locus as the CARK gene.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1 or 3, or the nucleotide sequence of the DNA insert of the plasmid deposited with ATCC as Accession Number PTA-1530. In other embodiment, the nucleic acid is at least 30, 50, 100, 150, 200, 250, 300, 350, 400, 450, 467, 500, 550, 600, 650, 700, 750, 800, 850, 900, or 950 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50° C., preferably at 55° C., more preferably at 60° C., and even more preferably at 65° C. Preferably, an isolated nucleic acid molecule of the invention that hybridizes under stringent conditions to the sequence of SEQ ID NO:1 or 3 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the CARK sequences that may exist in the population, the skilled artisan will further appreciate that changes can be introduced by mutation into the nucleotide sequences of SEQ ID NO:1 or 3, or the nucleotide sequence of the DNA insert of the plasmid deposited with ATCC as Accession Number PTA-1530, thereby leading to changes in the amino acid sequence of the encoded CARK proteins, without altering the functional ability of the CARK proteins. For example, nucleotide substitutions leading to amino acid substitutions at "non-essential" amino acid residues can be made in the sequence of SEQ ID NO:1 or 3, or the nucleotide sequence of the DNA insert of the plasmid deposited with ATCC as Accession Number PTA-1530. A "non-essential" amino acid residue is a residue that can be altered from the wild-type sequence of CARK (e.g., the sequence of SEQ ID NO:2) without altering the biological activity, whereas an "essential" amino acid residue is required for biological activity. For example, amino acid residues that are conserved among the CARK proteins of the present invention, e.g., those present in the active site of the protein kinase domain, are predicted to be particularly unamenable to alteration. Furthermore, additional amino acid residues that are conserved between the CARK proteins of the present invention and other ankyrin repeat containing kinases are not likely to be amenable to alteration.

Accordingly, another aspect of the invention pertains to nucleic acid molecules encoding CARK proteins that contain changes in amino acid residues that are not essential for activity. Such CARK proteins differ in amino acid sequence from SEQ ID NO:2, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 95%, 98% or more homologous to SEQ ID NO:2.

An isolated nucleic acid molecule encoding a CARK protein homologous to the protein of SEQ ID NO:2 can be created by introducing one or more nucleotide substitutions, additions or deletions into the nucleotide sequence of SEQ ID NO:1 or 3, or the nucleotide sequence of the DNA insert of the plasmid deposited with ATCC as Accession Number PTA-1530, such that one or more amino acid substitutions, additions or deletions are introduced into the encoded protein. Mutations can be introduced into SEQ ID NO:1 or 3, or the nucleotide sequence of the DNA insert of the plasmid deposited with ATCC as Accession Number PTA-1530, by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a CARK protein is preferably replaced with another amino acid residue from the same side chain family. Alternatively, in another embodiment, mutations can be introduced randomly along all or part of a CARK coding sequence, such as by saturation mutagenesis, and the resultant mutants can be screened for CARK biological activity to identify mutants that retain activity. Following mutagenesis of SEQ ID NO:1 or 3, or the nucleotide sequence of the DNA insert of the plasmid deposited with ATCC as Accession Number PTA-1530, the encoded protein can be expressed recombinantly and the activity of the protein can be determined.

In a preferred embodiment, a mutant CARK protein can be assayed for the ability to 1) regulate transmission of signals from cellular receptors, e.g., cardiac cell growth factor receptors; 2) modulate the entry of cells, e.g., cardiac precursor cells, into mitosis; 3) modulate cellular differentiation; 4) modulate cell death; and 5) regulate cytoskeleton function, e.g., actin bundling.

In addition to the nucleic acid molecules encoding CARK proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid.

The antisense nucleic acid can be complementary to an entire CARK coding strand, or to only a portion thereof. In one embodiment, an antisense nucleic acid molecule is antisense to a "coding region" of the coding strand of a nucleotide sequence encoding CARK. The term "coding region" refers to the region of the nucleotide sequence comprising codons which are translated into amino acid residues (e.g., the coding region of human CARK corresponds to SEQ ID NO:3). In another embodiment, the antisense nucleic acid molecule is antisense to a "noncoding region" of the coding strand of a nucleotide sequence encoding CARK. The term "noncoding region" refers to 5' and 3' sequences which flank the coding region that are not translated into amino acids (i.e., also referred to as 5' and 3' untranslated regions).

Given the coding strand sequences encoding CARK disclosed herein (e.g., SEQ ID NO:3), antisense nucleic acids of the invention can be designed according to the rules of Watson and Crick base pairing. The antisense nucleic acid molecule can be complementary to the entire coding region of CARK mRNA, but more preferably is an oligonucleotide which is antisense to only a portion of the coding or noncoding region of CARK mRNA. For example, the antisense oligonucleotide can be complementary to the region surrounding the translation start site of CARK mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a CARK protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An o:-anomeric nucleic acid molecule forms specific double-stranded hybrids with complementary RNA in which, contrary to the usual β-units, the strands run parallel to each other (Gaultier et al. (1987) Nucleic Acids. Res. 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) FEBS Lett. 215:327–330).

In still another embodiment, an antisense nucleic acid of the invention is a ribozyme.

Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave CARK mRNA transcripts to thereby inhibit translation of CARK mRNA. A ribozyme having specificity for a CARK-encoding nucleic acid can be designed based upon the nucleotide sequence of a CARK cDNA disclosed herein (i.e., SEQ ID NO:1 or 3, or the nucleotide sequence of the DNA insert of the plasmid deposited with ATCC as Accession Number PTA-1530). For example, a derivative of a Tetrahymena L-19 IVS RNA can be constructed in which the nucleotide sequence of the active site is complementary to the nucleotide sequence to be cleaved in a CARK-encoding mRNA. See, e.g., Cech et al. U.S. Pat. No. 4,987,071; and Cech et al. U.S. Pat. No. 5,116,742. Alternatively, CARK mRNA can be used to select a catalytic RNA having a specific ribonuclease activity from a pool of RNA molecules. See, e.g., Bartel, D. and Szostak, J. W. (1993) *Science* 261:1411–1418.

Alternatively, CARK gene expression can be inhibited by targeting nucleotide sequences complementary to the regulatory region of the CARK (e.g., the CARK promoter and/or enhancers) to form triple helical structures that prevent transcription of the CARK gene in target cells. See generally, Helene, C. (1991) *Anticancer Drug Des.* 6(6):569–84; Helene, C. et al. (1992) *Ann. N. Y Acad. Sci.* 660:27–36; and Maher, L. J. (1992) *Bioassays* 14(12):807–15.

In yet another embodiment, the CARK nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *Proc. Natl. Acad. Sci.* 93: 14670–675.

PNAs of CARK nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of CARK nucleic acid molecules can also be used in the analysis of single base pair mutations in a gene, (e.g., by PNA-directed PCR clamping);

as 'artificial restriction enzymes' when used in combination with other enzymes, (e.g., S1 nucleases (Hyrup B.

(1996) supra)); or as probes or primers for DNA sequencing or hybridization (Hyrup B. et al. (1996) supra; Perry-O'Keefe supra).

In another embodiment, PNAs of CARK can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of CARK nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. W088/09810) or the blood-brain barrier (see, e.g., PCT Publication No. W089/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated CARK Proteins and Anti-CARK Antibodies

One aspect of the invention pertains to isolated CARK proteins, and biologically active portions thereof, as well as polypeptide fragments suitable for use as immunogens to raise anti-CARK antibodies. In one embodiment, native CARK proteins can be isolated from cells or tissue sources by an appropriate purification scheme using standard protein purification techniques. In another embodiment, CARK proteins are produced by recombinant DNA techniques. Alternative to recombinant expression, a CARK protein or polypeptide can be synthesized chemically using standard peptide synthesis techniques.

An "isolated" or "purified" protein or biologically active portion thereof is substantially free of cellular material or other contaminating proteins from the cell or tissue source from which the CARK protein is derived, or substantially free from chemical precursors or other chemicals when chemically synthesized. The language "substantially free of cellular material" includes preparations of CARK protein in which the protein is separated from cellular components of the cells from which it is isolated or recombinantly produced. In one embodiment, the language "substantially free of cellular material" includes preparations of CARK protein having less than about 30% (by dry weight) of non-CARK protein (also referred to herein as a "contaminating protein"), more preferably less than about 20% of non-CARK protein, still more preferably less than about 10% of non-CARK protein, and most preferably less than about 5% non-CARK protein. When the CARK protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of CARK protein in which the protein is separated from chemical precursors or other chemicals which are involved in the synthesis of the protein. In one embodiment, the language "substantially free of chemical precursors or other chemicals" includes preparations of CARK protein having less than about 30% (by dry weight) of chemical precursors or non-CARK chemicals, more preferably less than about 20% chemical precursors or non-CARK chemicals, still more preferably less than about 10% chemical precursors or non-CARK chemicals, and most preferably less than about 5% chemical precursors or non-CARK chemicals.

As used herein, a "biologically active portion" of a CARK protein includes a fragment of a CARK protein which participates in an interaction between a CARK molecule and a non-CARK molecule. Biologically active portions of a CARK protein include peptides comprising amino acid sequences sufficiently homologous to or derived from the amino acid sequence of the CARK protein, e.g., the amino acid sequence shown in SEQ ID NO:2, which include less amino acids than the full length CARK proteins, and exhibit at least one activity of a CARK protein. Typically, biologically active portions comprise a domain or motif with at least one activity of the CARK protein, e.g., modulating signalling pathways associated with cellular growth and differentiation. A biologically active portion of a CARK protein can be a polypeptide which is, for example, 10, 25, 50, 100, 200 or more amino acids in length. Biologically active portions of a CARK protein can be used as targets for developing agents which modulate a CARK mediated activity, e.g., the modulation of signalling pathways associated with cellular growth and differentiation.

In one embodiment, a biologically active portion of a CARK protein comprises at least one ankyrin repeat domain, and/or at least one protein kinase domain. It is to be understood that a preferred biologically active portion of a CARK protein of the present invention may contain at least one ankyrin repeat domain. Another preferred biologically active portion of a CARK protein may contain at least two, three, four, five, six, seven, eight, or nine ankyrin repeat domains. Yet another preferred biologically active portion of a CARK protein may contain at least one protein kinase domain. Moreover, other biologically active portions, in which other regions of the protein are deleted, can be prepared by recombinant techniques and evaluated for one or more of the functional activities of a native CARK protein.

In a preferred embodiment, the CARK protein has an amino acid sequence shown in SEQ ID NO:2. In other embodiments, the CARK protein is substantially homologous to SEQ ID NO:2, and retains the functional activity of the protein of SEQ ID NO:2, yet differs in amino acid sequence due to natural allelic variation or mutagenesis, as described in detail in subsection I above. Accordingly, in another embodiment, the CARK protein is a protein which comprises an amino acid sequence at least about 50%, 55%, 60%, 65%, 70%, 75%, 80%, 85%, 90%, 95%, 98% or more homologous to SEQ ID NO:2.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the CARK amino acid sequence of SEQ ID NO:2 having 177 amino acid residues, at least 80, preferably at least 100, more preferably at least 120, even more preferably at least 140, and even more preferably at least 150, 160 or 170 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a finction of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to CARK nucleic acid molecules of the invention. BLAST protein searches can be performed with the XBLAST program, score=50, wordlength=3 to obtain amino acid sequences homologous to CARK protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

The invention also provides CARK chimeric or fusion proteins. As used herein, a CARK "chimeric protein" or "fusion protein" comprises a CARK polypeptide operatively linked to a non-CARK polypeptide. An "CARK polypeptide" refers to a polypeptide having an amino acid sequence corresponding to CARK, whereas a "non-CARK polypeptide" refers to a polypeptide having an amino acid sequence corresponding to a protein which is not substantially homologous to the CARK protein, e.g., a protein which is different from the CARK protein and which is derived from the same or a different organism. Within a CARK fusion protein the CARK polypeptide can correspond to all or a portion of a CARK protein. In a preferred embodiment, a CARK fusion protein comprises at least one biologically active portion of a CARK protein. In another preferred embodiment, a CARK fusion protein comprises at least two biologically active portions of a CARK protein. Within the fusion protein, the term "operatively linked" is intended to indicate that the CARK polypeptide and the non-CARK polypeptide are fused in-frame to each other. The non-CARK polypeptide can be fused to the N-terminus or C-terminus of the CARK polypeptide.

For example, in one embodiment, the fusion protein is a GST-CARK fusion protein in which the CARK sequences are fused to the C-terminus of the GST sequences. Such fusion proteins can facilitate the purification of recombinant CARK.

In another embodiment, the fusion protein is a CARK protein containing a heterologous signal sequence at its N-terminus. In certain host cells (e.g., mammalian host cells), expression and/or secretion of CARK can be increased through use of a heterologous signal sequence.

The CARK fusion proteins of the invention can be incorporated into pharmaceutical compositions and administered to a subject in vivo. The CARK fusion proteins can be used to affect the bioavailability of a CARK substrate. Use of CARK fusion proteins may be useful therapeutically for the treatment of disorders caused by, for example, (i) aberrant modification or mutation of a gene encoding a CARK protein; (ii) mis-regulation of the CARK gene; and (iii) aberrant post-translational modification of a CARK protein.

Moreover, the CARK-fusion proteins of the invention can be used as immunogens to produce anti-CARK antibodies in a subject, to purify CARK ligands and in screening assays to identify molecules which inhibit the interaction of CARK with a CARK substrate.

Preferably, a CARK chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). A CARK-encoding nucleic acid can be cloned into such an expression vector such that the fusion moiety is linked in-frame to the CARK protein.

The present invention also pertains to variants of the CARK proteins which function as either CARK agonists (mimetics) or as CARK antagonists. Variants of the CARK proteins can be generated by mutagenesis, e.g., discrete point mutation or truncation of a CARK protein. An agonist of the CARK proteins can retain substantially the same, or a subset, of the biological activities of the naturally occurring form of a CARK protein. An antagonist of a CARK protein can inhibit one or more of the activities of the naturally occurring form of the CARK protein by, for example, competitively modulating a CARK-mediated activity of a CARK protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the CARK protein.

In one embodiment, variants of a CARK protein which function as either CARK agonists (mimetics) or as CARK antagonists can be identified by screening combinatorial libraries of mutants, e.g., truncation mutants, of a CARK protein for CARK protein agonist or antagonist activity. In one embodiment, a variegated library of CARK variants is generated by combinatorial mutagenesis at the nucleic acid level and is encoded by a variegated gene library. A variegated library of CARK variants can be produced by, for example, enzymatically ligating a mixture of synthetic oligonucleotides into gene sequences such that a degenerate set of potential CARK sequences is expressible as individual polypeptides, or alternatively, as a set of larger fusion proteins (e.g., for phage display) containing the set of CARK sequences therein. There are a variety of methods which can be used to produce libraries of potential CARK variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential CARK sequences. Methods for synthesizing degenerate oligonucleotides are known in the art (see, e.g., Narang, S. A. (1983) Tetrahedron 39:3; Itakura et al. (1984) Annu. Rev. Biochem. 53:323; Itakura et al. (1984) Science 198:1056; Ike et al. (1983) Nucleic Acid Res. 11:477.

In addition, libraries of fragments of a CARK protein coding sequence can be used to generate a variegated population of CARK fragments for screening and subsequent selection of variants of a CARK protein. In one embodiment, a library of coding sequence fragments can be generated by treating a double stranded PCR fragment of a CARK coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with SI nuclease, and ligating the resulting fragment library into an expression vector. By this method, an expression library can be derived which encodes N-terminal, C-terminal and internal fragments of various sizes of the CARK protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of CARK proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify CARK variants (Arkin and Yourvan (1992) Proc. Natl. Acad. Sci. USA 89:7811–7815; Delgrave et al. (1993) Protein Engineering 6(3):327–331).

In one embodiment, cell based assays can be exploited to analyze a variegated CARK library. For example, a library of expression vectors can be transfected into a cell line, e.g., a cardiac cell line, which ordinarily responds to a particular ligand in a CARK-dependent manner. The transfected cells are then contacted with the ligand and the effect of expression of the mutant on signaling by the ligand can be detected, e.g., by monitoring intracellular calcium, IP3, or diacylglycerol concentration, phosphorylation profile of intracellular proteins, cell proliferation and/or migration, or the activity of a CARK-regulated transcription factor. Plasmid DNA can then be recovered from the cells which score for inhibition, or alternatively, potentiation of signaling by the ligand, and the individual clones further characterized.

An isolated CARK protein, or a portion or fragment thereof, can be used as an immunogen to generate antibodies that bind CARK using standard techniques for polyclonal and monoclonal antibody preparation. A full-length CARK protein can be used or, alternatively, the invention provides antigenic peptide fragments of CARK for use as immunogens. The antigenic peptide of CARK comprises at least 8 amino acid residues of the amino acid sequence shown in SEQ ID NO:2 and encompasses an epitope of CARK such that an antibody raised against the peptide forms a specific immune complex with CARK. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of CARK that are located on the surface of the protein, e.g., hydrophilic regions, as well as regions with high antigenicity (see, for example, FIG. 2).

A CARK immunogen typically is used to prepare antibodies by immunizing a suitable subject, (e.g., rabbit, goat, mouse or other mammal) with the immunogen. An appropriate immunogenic preparation can contain, for example, recombinantly expressed CARK protein or a chemically synthesized CARK polypeptide. The preparation can further include an adjuvant, such as Freund's complete or incomplete adjuvant, or similar immunostimulatory agent. Immunization of a suitable subject with an immunogenic CARK preparation induces a polyclonal anti-CARK antibody response.

Accordingly, another aspect of the invention pertains to anti-CARK antibodies. The term "antibody" as used herein refers to immunoglobulin molecules and immunologically active portions of immunoglobulin molecules, i.e., molecules that contain an antigen binding site which specifically binds (immunoreacts with) an antigen, such as CARK. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind CARK. The term "monoclonal antibody" or "monoclonal antibody composition", as used herein, refers to a population of antibody molecules that contain only one species of an antigen binding site capable of immunoreacting with a particular epitope of CARK. A monoclonal antibody composition thus typically displays a single binding affinity for a particular CARK protein with which it immunoreacts.

Polyclonal anti-CARK antibodies can be prepared as described above by immunizing a suitable subject with a CARK immunogen. The anti-CARK antibody titer in the immunized subject can be monitored over time by standard techniques, such as with an enzyme linked immunosorbent assay (ELISA) using immobilized CARK. If desired, the antibody molecules directed against CARK can be isolated from the mammal (e.g., from the blood) and further purified by well known techniques, such as protein A chromatography to obtain the IgG fraction. At an appropriate time after immunization, e.g., when the anti-CARK antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem* .255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, New York (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a CARK immunogen as described above, and the culture supernatants of the resulting hybridoma cells are screened to identify a hybridoma producing a monoclonal antibody that binds CARK.

Any of the many well known protocols used for fusing lymphocytes and immortalized cell lines can be applied for the purpose of generating an anti-CARK monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, Monoclonal Antibodies, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind CARK, e.g., using a standard ELISA assay.

Alternative to preparing monoclonal antibody-secreting hybridomas, a monoclonal anti-CARK antibody can be identified and isolated by screening a recombinant combinatorial immunoglobulin library (e.g., an antibody phage display library) with CARK to thereby isolate immunoglobulin library members that bind CARK. Kits for generating and screening phage display libraries are commercially available (e.g., the Pharmacia *Recombinant Phage Antibody System, Catalog No.* 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBOJ* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-CARK antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCTIUS86/02269; Akira, et al. European Patent Application 184,187; Taniguchi, M., European Patent Application 171, 496; Morrison et al. European Patent Application 173,494;

Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyan et al. (1988) *Science* 239:1534; and Beidler et al. (1988) *J. Immunol.* 141:4053–4060.

An anti-CARK antibody (e.g., monoclonal antibody) can be used to isolate CARK by standard techniques, such as affinity chromatography or immunoprecipitation. An anti-CARK antibody can facilitate the purification of natural CARK from cells and of recombinantly produced CARK expressed in host cells. Moreover, an anti-CARK antibody can be used to detect CARK protein (e.g., in a cellular lysate or cell supernatant) in order to evaluate the abundance and pattern of expression of the CARK protein. Anti-CARK antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Recombinant Expression Vectors and Host Cells

Another aspect of the invention pertains to vectors, preferably expression vectors, containing a nucleic acid encoding a CARK protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990).

Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., CARK proteins, mutant forms of CARK proteins, fusion proteins, and the like).

The recombinant expression vectors of the invention can be designed for expression of CARK proteins in prokaryotic or eukaryotic cells. For example, CARK proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5

(Pharmacia, Piscataway, N.J.) which fuse glutathione S-transferase (GST), maltose E binding protein, or protein A, respectively, to the target recombinant protein.

Purified fusion proteins can be utilized in CARK activity assays, (e.g., direct assays or competitive assays described in detail below), or to generate antibodies specific for CARK proteins, for example. In a preferred embodiment, a CARK fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion E. coli expression vectors include pTrc (Amann et al., (1988) Gene 69:301–315) and pET 11d (Studier et al., Gene Expression Technology: Methods in Enzymology 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS 174(DE3) from a resident prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman, S., Gene Expression Technology: Methods in Enzymology 185, Academic Press, San Diego, Calif. (1990) 119–128). Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111–2118). Such alteration of nucleic acid sequences of the invention can be carried out by standard DNA synthesis techniques.

In another embodiment, the CARK expression vector is a yeast expression vector. Examples of vectors for expression in yeast S. cerivisae include pYepSec1 (Baldari, et al., (1987) Embo J. 6:229–234), pMFa (Kurjan and Herskowitz, (1982) Cell 30:933–943), pJRY88 (Schultz et al., (1987) Gene 54:113–123), pYES2 (Invitrogen Corporation, San Diego, Calif.), and picZ (InVitrogen Corp, San Diego, Calif.).

Alternatively, CARK proteins can be expressed in insect cells using baculovirus expression vectors. Baculovirus vectors available for expression of proteins in cultured insect cells (e.g., Sf 9 cells) include the pAc series (Smith et al. (1983) Mol. Cell Biol. 3:2156–2165) and the pVL series (Lucklow and Summers (1989) Virology 170:31–39).

In yet another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187–195). When used in mammalian cells, the expression vector's control finctions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) Science 249:374–379) and the oc-fetoprotein promoter (Campes and Tilghman (1989) Genes Dev. 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to CARK mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1(1) 1986.

Another aspect of the invention pertains to host cells into which a CARK nucleic acid molecule of the invention is introduced, e.g., a CARK nucleic acid molecule within a recombinant expression vector or a CARK nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a CARK protein can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed, Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a CARK protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a CARK protein. Accordingly, the invention further provides methods for producing a CARK protein using the host cells of the invention. In one embodiment, the method comprises culturing the host cell of the invention (into which a recombinant expression vector encoding a CARK protein has been introduced) in a suitable medium such that a CARK protein is produced. In another embodiment, the method further comprises isolating a CARK protein from the medium or the host cell.

The host cells of the invention can also be used to produce non-human transgenic animals. For example, in one embodiment, a host cell of the invention is a fertilized oocyte or an embryonic stem cell into which CARK-coding sequences have been introduced. Such host cells can then be used to create non-human transgenic animals in which exogenous CARK sequences have been introduced into their genome or homologous recombinant animals in which endogenous CARK sequences have been altered. Such animals are useful for studying the function and/or activity of a CARK and for identifying and/or evaluating modulators of CARK activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous CARK gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a CARK-encoding nucleic acid into the male pronuclei of a fertilized oocyte, e.g., by microinjection, retroviral infection, and allowing the oocyte to develop in a pseudopregnant female foster animal. The CARK cDNA sequence of SEQ ID NO:1 can be introduced as a transgene into the genome of a non-human animal. Alternatively, a nonhuman homologue of a human CARK gene, such as a mouse or rat CARK gene, can be used as a transgene. Alternatively, a CARK gene homologue, such as another CARK family member, can be isolated based on hybridization to the CARK cDNA sequences of SEQ ID NO:1 or 3, or the DNA insert of the plasmid deposited with ATCC as Accession Number PTA-1530 (described further in subsection I above) and used as a transgene. Intronic sequences and polyadenylation signals can also be included in the transgene to increase the efficiency of expression of the transgene. A tissue-specific regulatory sequence(s) can be operably linked to a CARK transgene to direct expression of a CARK protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of a CARK transgene in its genome and/or expression of CARK mRNA in tissues or cells of the animals. A transgenic founder animal can then be used to breed additional animals carrying the transgene. Moreover, transgenic animals carrying a transgene encoding a CARK protein can further be bred to other transgenic animals carrying other transgenes.

To create a homologous recombinant animal, a vector is prepared which contains at least a portion of a CARK gene into which a deletion, addition or substitution has been introduced to thereby alter, e.g., functionally disrupt, the CARK gene. The CARK gene can be a human gene (e.g., the cDNA of SEQ ID NO:3), but more preferably, is a non-human homologue of a human CARK gene (e.g., a cDNA isolated by stringent hybridization with the nucleotide sequence of SEQ ID NO:1). For example, a mouse CARK gene can be used to construct a homologous recombination nucleic acid molecule, e.g., a vector, suitable for altering an endogenous CARK gene in the mouse genome. In a preferred embodiment, the homologous recombination nucleic acid molecule is designed such that, upon homologous recombination, the endogenous CARK gene is functionally disrupted (i.e., no longer encodes a functional protein; also referred to as a "knock out" vector). Alternatively, the homologous recombination nucleic acid molecule can be designed such that, upon homologous recombination, the endogenous CARK gene is mutated or otherwise altered but still encodes functional protein (e.g., the upstream regulatory region can be altered to thereby alter the expression of the endogenous CARK protein). In the homologous recombination nucleic acid molecule, the altered portion of the CARK gene is flanked at its 5' and 3' ends by additional nucleic acid sequence of the CARK gene to allow for homologous recombination to occur between the exogenous CARK gene carried by the homologous recombination nucleic acid molecule and an endogenous CARK gene in a cell, e.g., an embryonic stem cell. The additional flanking CARK nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced CARK gene has homologously recombined with the endogenous CARK gene are selected (see e.g., Li, E. et al. (1992) *Cell* 69:915). The selected cells can then injected into a blastocyst of an animal (e.g., a mouse) to form aggregation chimeras (see e.g., Bradley, A. in Teratocarcinomas and Embryonic Stem Cells: A Practical Approach, E. J. Robertson, ed. (IRL, Oxford, 1987) pp. 113–152). A chimeric embryo can then be implanted into a suitable pseudopregnant female foster animal and the embryo brought to term. Progeny harboring the homologously recombed DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) Nature 385:810–813 and PCT International Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The CARK nucleic acid molecules, fragments of CARK proteins, and anti-CARK antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a CARK protein or an anti-CARK antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules, oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Patent 5,328,470) or by stereotactic injection (see e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a CARK protein of the invention has one or more of the following activities: 1) it regulates transmission of signals from cellular receptors, e.g., cardiac cell growth factor receptors; 2) it modulates the entry of cells, e.g., cardiac precursor cells, into mitosis; 3) it modulates cellular differentiation; 4) it modulates cell death; and 5) it regulates cytoskeleton function, e.g., actin bundling, and, thus, can be used to, for example, 1) regulate transmission of signals from cellular receptors, e.g., cardiac cell growth factor receptors; 2) modulate the entry of cells, e.g., cardiac precursor cells, into mitosis; 3) modulate cellular differentiation; 4) modulate cell death; and 5) regulate cytoskeleton function, e.g., actin bundling.

The isolated nucleic acid molecules of the invention can be used, for example, to 35 express CARK protein (e.g., via a recombinant expression vector in a host cell in gene therapy applications), to detect CARK mRNA (e.g., in a biological sample) or a genetic alteration in a CARK gene, and to modulate CARK activity, as described further below.

The CARK proteins can be used to treat disorders characterized by insufficient or excessive production of a CARK substrate or production of CARK inhibitors. In addition, the CARK proteins can be used to screen for naturally occurring CARK substrates, to screen for drugs or compounds which modulate CARK activity, as well as to treat disorders characterized by insufficient or excessive production of CARK protein or production of CARK protein forms which have decreased, aberrant or unwanted activity compared to CARK wild type protein (e.g., cellular proliferation or differentiation associated disorders). Moreover, the anti-CARK antibodies of the invention can be used to detect and isolate CARK proteins, regulate the bioavailability of CARK proteins, and modulate CARK activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to CARK proteins, have a stimulatory or inhibitory effect on, for example, CARK expression or CARK activity, or have a stimulatory or inhibitory effect on, for example, the expression or activity of CARK substrate.

In one embodiment, the invention provides assays for screening candidate or test compounds which are substrates of a CARK protein or polypeptide or biologically active portion thereof. In another embodiment, the invention provides assays for screening candidate or test compounds which bind to or modulate the activity of a CARK protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner USP '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a CARK protein or biologically active portion thereof is contacted with a test compound and the ability of the test compound to modulate CARK activity is determined. Determining the ability of the test compound to modulate CARK activity can be accomplished by monitoring, for example, intracellular calcium, IP3, or diacylglycerol concentration, phosphorylation profile of intracellular proteins, cell proliferation and/or migration, or the activity of a CARK-regulated transcription factor. The cell, for example, can be of mammalian origin, e.g., a cardiac cell.

The ability of the test compound to modulate CARK binding to a substrate or to bind to CARK can also be determined. Determining the ability of the test compound to modulate CARK binding to a substrate can be accomplished, for example, by coupling the CARK substrate with a radioisotope or enzymatic label such that binding of the CARK substrate to CARK can be determined by detecting the labeled CARK substrate in a complex. Determining the ability of the test compound to bind CARK can be accomplished, for example, by coupling the compound with a radioisotope or enzymatic label such that binding of the compound to CARK can be determined by detecting the labeled CARK compound in a complex. For example, compounds (e.g., CARK substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a CARK substrate) to interact with CARK without the labeling of any of the interactants. For example, a microphysiometer can be used to detect the interaction of a compound with CARK without the labeling of either the compound or the CARK. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and CARK.

In another embodiment, an assay is a cell-based assay comprising contacting a cell expressing a CARK target molecule (e.g., a CARK substrate) with a test compound and determining the ability of the test compound to modulate (e.g. stimulate or inhibit) the activity of the CARK target molecule. Determining the ability of the test compound to modulate the activity of a CARK target molecule can be accomplished, for example, by determining the ability of the CARK protein to bind to or interact with the CARK target molecule.

Determining the ability of the CARK protein or a biologically active fragment thereof, to bind to or interact with a CARK target molecule can be accomplished by one of the methods described above for determining direct binding. In a preferred embodiment, determining the ability of the CARK protein to bind to or interact with a CARK target molecule can be accomplished by determining the activity of the target molecule. For example, the activity of the target molecule can be determined by detecting induction of a cellular second messenger of the target (i.e., intracellular $Ca^{2+}$, diacylglycerol, $IP_3$, and the like), detecting catalytic/enzymatic activity of the target an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which a CARK protein or biologically active portion thereof is contacted with a test compound and the ability of the test compound to bind to the CARK protein or biologically active portion thereof is determined. Preferred biologically active portions of the CARK proteins to be used in assays of the present invention include fragments which participate in interactions with non-CARK molecules, e.g., fragments with high surface probability scores (see, for example, FIG. 2). Binding of the test compound to the CARK protein can be determined either directly or indirectly as described above. In a preferred embodiment, the assay includes contacting the CARK protein or biologically active portion thereof with a known compound which binds CARK to form an assay mixture, contacting the assay mixture with a test compound, and determining the ability of the test compound to interact with a CARK protein, wherein determining the ability of the test compound to interact with a CARK protein comprises determining the ability of the test compound to preferentially bind to CARK or biologically active portion thereof as compared to the known compound.

In another embodiment, the assay is a cell-free assay in which a CARK protein or biologically active portion thereof is contacted with a test compound and the ability of the test compound to modulate (e.g., stimulate or inhibit) the activity of the CARK protein or biologically active portion thereof is determined. Determining the ability of the test compound to modulate the activity of a CARK protein can be accomplished, for example, by determining the ability of the CARK protein to bind to a CARK target molecule by one of the methods described above for determining direct binding. Determining the ability of the CARK protein to bind to a CARK target molecule can also be accomplished using a technology such as real-time Biomolecular Interaction Analysis (BIA). Sjolander, S. and Urbaniczky, C. (1991) Anal. Chem. 63:2338–2345 and Szabo et al. (1995) Curr. Opin. Struct. Biol. 5:699–705. As used herein, "BIA" is a technology for studying biospecific interactions in real time, without labeling any of the interactants (e.g., BlAcore). Changes in the optical phenomenon of surface plasmon resonance (SPR) can be used as an indication of real-time reactions between biological molecules.

In an alternative embodiment, determining the ability of the test compound to modulate the activity of a CARK protein can be accomplished by determining the ability of the CARK protein to further modulate the activity of a downstream effector of a CARK target molecule. For example, the activity of the effector molecule on an appropriate target can be determined or the binding of the effector to an appropriate target can be determined as previously described.

In yet another embodiment, the cell-free assay involves contacting a CARK protein or biologically active portion thereof with a known compound which binds the CARK protein to form an assay mixture, contacting the assay mixture with a test compound, and determining the ability of the test compound to interact with the CARK protein, wherein determining the ability of the test compound to interact with the CARK protein comprises determining the ability of the CARK protein to preferentially bind to or modulate the activity of a CARK target molecule.

The cell-free assays of the present invention are amenable to use of both soluble and/or membrane-bound forms of isolated proteins (e.g., CARK proteins or biologically active portions thereof). In the case of cell-free assays in which a membrane-bound form of an isolated protein is used it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesito, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy- 1-propane sulfonate (CHAPSO), or N-dodecyl=N,N-dimethyl-3-ammonio-1-propane sulfonate.

In more than one embodiment of the above assay methods of the present invention, it may be desirable to immobilize either CARK or its target molecule to facilitate separation of complexed from uncomplexed forms of one or both of the proteins, as well as to accommodate automation of the assay. Binding of a test compound to a CARK protein, or interaction of a CARK protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/CARK transferase/CARK fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or CARK protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of CARK binding or activity determined using standard techniques.

Other techniques for immobilizing proteins on matrices can also be used in the screening assays of the invention. For example, either a CARK protein or a CARK target molecule can be immobilized utilizing conjugation of biotin and streptavidin. Biotinylated CARK protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with CARK protein or target molecules but which do not interfere with binding of the CARK protein to its target molecule can be derivatized to the wells of the plate, and unbound target or CARK protein trapped in the wells by antibody conjugation. Methods for detecting such complexes, in addition to those described above for the GST-immobilized complexes, include immunodetection of complexes using antibodies reactive with the CARK protein or target molecule, as well as enzyme-linked assays which rely on detecting an enzymatic activity associated with the CARK protein or target molecule.

In another embodiment, modulators of CARK expression are identified in a method wherein a cell is contacted with a candidate compound and the expression of CARK mRNA or protein in the cell is determined. The level of expression of CARK mRNA or protein in the presence of the candidate compound is compared to the level of expression of CARK mRNA or protein in the absence of the candidate compound. The candidate compound can then be identified as a modulator of CARK expression based on this comparison. For example, when expression of CARK mRNA or protein is greater (statistically significantly greater) in the presence of the candidate compound than in its absence, the candidate compound is identified as a stimulator of CARK mRNA or protein expression.

Alternatively, when expression of CARK mRNA or protein is less (statistically significantly less) in the presence of the candidate compound than in its absence, the candidate compound is identified as an inhibitor of CARK mRNA or protein expression. The level of CARK mRNA or protein expression in the cells can be determined by methods described herein for detecting CARK mRNA or protein.

In yet another aspect of the invention, the CARK proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent W094/10300), to identify other proteins, which bind to or interact with CARK ("CARK-binding proteins" or "CARK-bp") and are involved in CARK activity. Such CARK-binding proteins are also likely to be involved in the propagation of signals by the CARK proteins or CARK targets as, for example, downstream elements of a CARK-mediated signaling pathway. Alternatively, such CARK-binding proteins are likely to be CARK inhibitors.

The two-hybrid system is based on the modular nature of most transcription factors, which consist of separable DNA-binding and activation domains. Briefly, the assay utilizes two different DNA constructs. In one construct, the gene that codes for a CARK protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a CARK-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the CARK protein.

In another aspect, the invention pertains to a combination of two or more of the assays described herein. For example, a modulating agent can be identified using a cell-based or a cell free assay, and the ability of the agent to modulate the activity of a CARK protein can be confirmed in vivo, e.g., in an animal such as an animal model for a cardiovascular disorder.

This invention further pertains to novel agents identified by the above-described screening assays. Accordingly, it is within the scope of this invention to further use an agent identified as described herein in an appropriate animal model. For example, an agent identified as described herein (e.g., a CARK modulating agent, an antisense CARK nucleic acid molecule, a CARK-specific antibody, or a CARK-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the CARK nucleotide sequences, described herein, can be used to map the location of the CARK genes on a chromosome. The mapping of the CARK sequences to chromosomes is an important first step in correlating these sequences with genes associated with disease.

Briefly, CARK genes can be mapped to chromosomes by preparing PCR primers (preferably 15–25 bp in length) from the CARK nucleotide sequences. Computer analysis of the CARK sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the CARK sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the CARK nucleotide sequences to design oligonucleotide primers, sublocalization can be achieved with panels of fragments from specific chromosomes. Other mapping strategies which can similarly be used to map a CARK sequence to its chromosome include in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific CDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the CARK gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The CARK sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the CARK nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The CARK nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from CARK nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial CARK Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e.

another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding iregions, making it easier to differentiate individuals using this technique. Examples of polynucleotide reagents include the CARK nucleotide sequences or portions thereof, e.g., fragments derived from the noncoding regions of SEQ ID NO:1 having a length of at least 20 bases, preferably at least 30 bases.

The CARK nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such CARK probes can be used to identify tissue by species and/or by organ type.

In a similar fashion, these reagents, e.g., CARK primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining CARK protein and/or nucleic acid expression as well as CARK activity, in the context of a biological sample (e.g., blood, serum, cells, tissue) to thereby determine whether an individual is afflicted with a disease or disorder, or is at risk of developing a disorder, associated with aberrant or unwanted CARK expression or activity. The invention also provides for prognostic (or predictive) assays for determining whether an individual is at risk of developing a disorder associated with CARK protein, nucleic acid expression or activity. For example, mutations in a CARK gene can be assayed in a biological sample. Such assays can be used for prognostic or predictive purpose to thereby phophylactically treat an individual prior to the onset of a disorder characterized by or associated with CARK protein, nucleic acid expression or activity.

Another aspect of the invention pertains to monitoring the influence of agents (e.g., drugs, compounds) on the expression or activity of CARK in clinical trials.

These and other agents are described in further detail in the following sections.

1. Diagnostic Assays

An exemplary method for detecting the presence or absence of CARK protein or nucleic acid in a biological sample involves obtaining a biological sample from a test subject and contacting the biological sample with a compound or an agent capable of detecting CARK protein or nucleic acid (e.g., mRNA, genomic DNA) that encodes CARK protein such that the presence of CARK protein or nucleic acid is detected in the biological sample. A preferred agent for detecting CARK mRNA or genomic DNA is a labeled nucleic acid probe capable of hybridizing to CARK mRNA or genomic DNA. The nucleic acid probe can be, for example, a full-length CARK nucleic acid, such as the nucleic acid of SEQ ID NO:1 or 3, or the DNA insert of the plasmid deposited with ATCC as Accession Number PTA-1530, or a portion thereof, such as an oligonucleotide of at least 15, 30, 50, 100, 250 or 500 nucleotides in length and sufficient to specifically hybridize under stringent conditions to CARK mRNA or genomic DNA. Other suitable probes for use in the diagnostic assays of the invention are described herein.

A preferred agent for detecting CARK protein is an antibody capable of binding to CARK protein, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include issues, cells and biological fluids isolated from a subject, as well as tissues, cells and fluids resent within a subject. That is, the detection method of the invention can be used to detect CARK mRNA, protein, or genomic DNA in a biological sample in vitro as well as in vivo. For example, in vitro techniques for detection of CARK mRNA include Northern hybridizations and in situ hybridizations. In vitro techniques for detection of CARK protein include enzyme linked immunosorbent assays (ELISAs), Western blots, immunoprecipitations and immunofluorescence. In vitro techniques for detection of CARK genomic DNA include Southern hybridizations. Furthermore, in vivo techniques for detection of CARK protein include introducing into a subject a labeled anti-CARK antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting CARK protein, mRNA, or genomic DNA, such that the presence of CARK protein, mRNA or genomic DNA is detected in the biological sample, and comparing the presence of CARK protein, mRNA or genomic DNA in the control sample with the presence of CARK protein, mRNA or genomic DNA in the test sample.

The invention also encompasses kits for detecting the presence of CARK in a biological sample. For example, the kit can comprise a labeled compound or agent capable of detecting CARK protein or mRNA in a biological sample; means for determining the amount of CARK in the sample; and means for comparing the amount of CARK in the sample with a standard. The compound or agent can be packaged in a suitable container. The kit can further comprise instructions for using the kit to detect CARK protein or nucleic acid.

2. Prognostic Assays

The diagnostic methods described herein can furthermore be utilized to identify subjects having or at risk of developing a disease or disorder associated with aberrant or unwanted CARK expression or activity. As used herein, the term "aberrant" includes a CARK expression or activity which deviates from the wild type CARK expression or activity. Aberrant expression or activity includes increased or decreased expression or activity, as well as expression or activity which does not follow the wild type developmental pattern of expression or the subcellular pattern of expression. For example, aberrant CARK expression or activity is intended to include the cases in which a mutation in the CARK gene causes the CARK gene to be under-expressed or over-expressed and situations in which such mutations result in a non-functional CARK protein or a protein which does not function in a wild-type fashion, e.g., a protein which does not interact with a CARK ligand or one which interacts with a non-CARK ligand. As used herein, the term "unwanted" includes an unwanted phenomenon involved in a biological response such as proliferation or differentiation. For example, the term unwanted includes a CARK expression or activity which is undesirable in a subject.

The assays described herein, such as the preceding diagnostic assays or the following assays, can be utilized to identify a subject having or at risk of developing a disorder associated with a misregulation in CARK protein activity or nucleic acid expression, such as a cardiovascular disorder. Alternatively, the prognostic assays can be utilized to identify a subject having or at risk for developing a disorder associated with a misregulation in CARK protein activity or nucleic acid expression, such as a cardiovascular disorder. Thus, the present invention provides a method for identifying a disease or disorder associated with aberrant or unwanted CARK expression or activity in which a test sample is obtained from a subject and CARK protein or nucleic acid (e.g., mRNA or genomic DNA) is detected, wherein the presence of CARK protein or nucleic acid is diagnostic for a subject having or at risk of developing a disease or disorder associated with aberrant or unwanted CARK expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted CARK expression or activity. For example, such methods can be used to determine whether a subject can be effectively treated with an agent for a cardiovascular disorder. Thus, the present invention provides methods for determining whether a subject can be effectively treated with an agent for a disorder associated with aberrant or unwanted CARK expression or activity in which a test sample is obtained and CARK protein or nucleic acid expression or activity is detected (e.g., wherein the abundance of CARK protein or nucleic acid expression or activity is diagnostic for a subject that can be administered the agent to treat a disorder associated with aberrant or unwanted CARK expression or activity).

The methods of the invention can also be used to detect genetic alterations in a CARK gene, thereby determining if a subject with the altered gene is at risk for a disorder characterized by misregulation in CARK protein activity or nucleic acid expression, such as a cardiovascular disorder. In preferred embodiments, the methods include detecting, in a sample of cells from the subject, the presence or absence of a genetic alteration characterized by at least one of an alteration affecting the integrity of a gene encoding a CARK-protein, or the mis-expression of the CARK gene. For example, such genetic alterations can be detected by ascertaining the existence of at least one of 1) a deletion of one or more nucleotides from a CARK gene; 2) an addition of one or more nucleotides to a CARK gene; 3) a substitution of one or more nucleotides of a CARK gene, 4) a chromosomal rearrangement of a CARK gene; 5) an alteration in the level of a messenger RNA transcript of a CARK gene, 6) aberrant modification of a CARK gene, such as of the methylation pattern of the genomic DNA, 7) the presence of a non-wild type splicing pattern of a messenger RNA transcript of a CARK gene, 8) a non-wild type level of a CARK-protein, 9) allelic loss of a CARK gene, and 10) inappropriate post-translational modification of a CARK-protein. As described herein, there are a large number of assays known in the art which can be used for detecting alterations in a CARK gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the CARK-gene (see Abravaya et al. (1995) *Nucleic Acids Res* .23:675–682). This method can include the steps of collecting a sample of cells from a subject, isolating nucleic acid (e.g., genomic, mRNA or both) from the cells of the sample, contacting the nucleic acid sample with one or more primers which specifically hybridize to a CARK gene under conditions such that hybridization and amplification of the CARK-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a CARK gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in CARK can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in CARK can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the CARK gene and detect mutations by comparing the sequence of the sample CARK with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the CARK gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type CARK sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with SI nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamnide gels to determine the site of mutation. See, for example, Cotton et al. (1988) *Proc. NatlAcadSci USA* 85:4397; Saleeba et al. (1992) Methods Enzymol. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in CARK cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a CARK sequence, e.g., a wild-type CARK sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in CARK genes. For example, single strand conformation polymorphism (SSCP) may be used to detect differences in electrophoretic mobility between mutant and wild type nucleic acids (orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control CARK nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a CARK gene. Furthermore, any cell type or tissue in which CARK is expressed may be utilized in the prognostic assays described herein.

3. Monitoring of Effects During Clinical Trials

Monitoring the influence of agents (e.g., drugs) on the expression or activity of a CARK protein (e.g., the modulation signalling pathways associated with cellular growth and differentiation) can be applied not only in basic drug screening, but also in clinical trials.

For example, the effectiveness of an agent determined by a screening assay as described herein to increase CARK gene expression, protein levels, or upregulate CARK activity, can be monitored in clinical trials of subjects exhibiting decreased CARK gene expression, protein levels, or downregulated CARK activity. Alternatively, the effectiveness of an agent determined by a screening assay to decrease CARK gene expression, protein levels, or downregulate CARK activity, can be monitored in clinical trials of subjects exhibiting increased CARK gene expression, protein levels, or upregulated CARK activity. In such clinical trials, the expression or activity of a CARK gene, and preferably, other genes that have been implicated in, for example, a CARK-associated disorder can be used as a "read out" or markers of the phenotype of a particular cell.

For example, and not by way of limitation, genes, including CARK, that are modulated in cells by treatment with an agent (e.g., compound, drug or small molecule) which modulates CARK activity (e.g., identified in a screening assay as described herein) can be identified. Thus, to study the effect of agents on CARK-associated disorders (e.g., disorders characterized by deregulated cellular growth or differentiation), for example, in a clinical trial, cells can be isolated and RNA prepared and analyzed for the levels of expression of CARK and other genes implicated in the CARK-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of CARK or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a CARK protein, mRNA, or genomic DNA in the preadministration sample; (iii) obtaining one or more post-administration samples from the subject; (iv) detecting the level of expression or activity of the CARK protein, mRNA, or genomic DNA in the post-administration samples; (v) comparing the level of expression or activity of the CARK protein, mRNA, or genomic DNA in the pre-administration sample with the CARK protein, mRNA, or genomic DNA in the post administration sample or samples; and (vi) altering the administration of the agent to the subject accordingly. For example, increased administration of the agent may be desirable to increase the expression or activity of CARK to higher levels than detected, i.e., to increase the effectiveness of the agent. Alternatively, decreased administration of the agent may be desirable to decrease expression or activity of CARK to lower levels than detected, i.e. to decrease the effectiveness of the agent. According to such an embodiment, CARK expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant or unwanted CARK expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the CARK molecules of the present invention or CARK modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted CARK expression or activity, by administering to the subject a CARK or an agent which modulates CARK expression or at least one CARK activity. Subjects at risk for a disease which is caused or contributed to by aberrant or unwanted CARK expression or activity can be identified by, for example, any or a combination of diagnostic or prognostic assays as described herein. Administration of a prophylactic agent can occur prior to the manifestation of symptoms characteristic of the CARK aberrancy, such that a disease or disorder is prevented or, alternatively, delayed in its progression. Depending on the type of CARK aberrancy, for example, a CARK, CARK agonist or CARK antagonist agent can be used for treating the subject. The appropriate agent can be determined based on screening assays described herein.

2. Therapeutic Methods

Another aspect of the invention pertains to methods of modulating CARK expression or activity for therapeutic purposes. Accordingly, in an exemplary embodiment, the modulatory method of the invention involves contacting a cell with a CARK or agent that modulates one or more of the activities of CARK protein activity associated with the cell. An agent that modulates CARK protein activity can be an agent as described herein, such as a nucleic acid or a protein, a naturally-occurring target molecule of a CARK protein (e.g., a CARK substrate), a CARK antibody, a CARK agonist or antagonist, a peptidomimetic of a CARK agonist or antagonist, or other small molecule. In one embodiment, the agent stimulates one or more CARK activities. Examples of such stimulatory agents include active CARK protein and a nucleic acid molecule encoding CARK that has been introduced into the cell. In another embodiment, the agent inhibits one or more CARK activities. Examples of such inhibitory agents include antisense CARK nucleic acid molecules, anti-CARK antibodies, and CARK inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a CARK protein or nucleic acid molecule. In one embodiment, the method involves administering an agent (e.g., an agent identified by a screening assay described herein), or combination of agents that modulates (e.g., upregulates or downregulates) CARK expression or activity. In another embodiment, the method involves administering a CARK protein or nucleic acid molecule as therapy to compensate for reduced, aberrant, or unwanted CARK expression or activity.

Stimulation of CARK activity is desirable in situations in which CARK is abnormally downregulated and/or in which increased CARK activity is likely to have a beneficial effect. For example, stimulation of CARK activity is desirable in situations in which a CARK is downregulated and/or in which increased CARK activity is likely to have a beneficial effect. Likewise, inhibition of CARK activity is desirable in situations in which CARK is abnormally upregulated and/or in which decreased CARK activity is likely to have a beneficial effect.

3. Pharmacogenomics

The CARK molecules of the present invention, as well as agents, or modulators which have a stimulatory or inhibitory effect on CARK activity (e.g., CARK gene expression) as identified by a screening assay described herein can be administered to individuals to treat (prophylactically or therapeutically) CARK-associated disorders (e.g., cardiovascular disorders) associated with aberrant or unwanted CARK activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to dminister a CARK molecule or CARK modulator as well as tailoring the dosage and/or therapeutic regimen of treatment with a CARK molecule or CARK modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10–11):983–985 and Linder, M. W. et al. (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a CARK protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses.

Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a CARK molecule or CARK modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a CARK molecule or CARK modulator, such as a modulator identified by one of the exemplary screening assays described herein.

This invention is further illustrated by the following examples which should not be construed as limiting. The contents of all references, patents and published patent applications cited throughout this application are incorporated herein by reference.

EXAMPLES

Example 1

Identification and Characterization of Human CARK cDNA

In this example, the identification and characterization of the gene encoding human CARK (also referred to as clone fchrfO13fO3) is described. Isolation of the human CARK cDNA The invention is based, at least in part, on the discovery of the human gene encoding CARK. The human CARK was isolated from a cDNA library which was prepared from tissue obtained from subjects suffering from congestive heart failure of ischemic and idiopathic origin. Briefly, a cardiac tissue sample was obtained from a biopsy of four patients suffering from congestive heart failure. mRNA was isolated from the cardiac tissue and a cDNA library was prepared therefrom using art known methods (described in, for example, *Molecular Cloning A Laboratory Manual*, 2nd Ed., ed. by Sambrook, Fritsch and Maniatis (Cold Spring Harbor Laboratory Press: 1989). Positive clones were isolated from these libraries using appropriate primers.

The sequence of the positive clone was determined and found to contain an open reading frame. The nucleotide sequence encoding the human CARK protein comprises about 3025 nucleic acids, and has the nucleic acid sequence shown in FIG. 1 and set forth as SEQ ID NO:1. The protein encoded by this nucleic acid comprises about 835 amino acids, and has the amino acid sequence shown in FIG. 1 and set forth as SEQ ID NO:2.

Analysis of Human CARK

A BLASTP 1.4 search (Altschul et al. (1990) *J. Mol. Biol.* 215:403) of the protein sequence of human CARK revealed that CARK is similar to the C. elegans protein containing similarity to ankyrin repeats and protein kinase motifs (Accession No. AF024491). This protein is approximately 42% identical (over CARK amino acids 126–370), 60% identical (over CARK amino acids 421–548), 65% identical (over CARK amino acids 582–686), 32% identical (over CARK amino acids 60–222), 75% identical (over CARK amino acids 381–404), 36% identical (over CARK amino acids 122–167), 48% identical (over CARK amino acids 10–36), 38% identical (over CARK amino acids 91–126), 52% identical (over CARK amino acids 556–678), 24% identical (over CARK amino acids 315–368), 25% identical (over CARK amino acids 74–161), and 29% identical (over CARK amino acids 219–259) at the amino acid level.

A BLASTN 1.4.9 search (Altschul et al. (1990) J. Mol. Biol. 215:403) of the nucleotide sequence of human CARK revealed that CARK is similar to Homo sapiens cDNAclone 1320937 (Accession No. AA758546). The CARK nucleic acid molecule is 100% identical to Homo sapiens cDNA-clone 1320937 (Accession No. AA758546) over nucleotides 2544 to 3010.

Analysis of primary and secondary protein structures, as shown in FIG. 2, was performed as follows: alpha, beta turn and coil regions, Garnier-Robson algorithm (Garnier et al. (1978) *J Mol Biol* 120:97); alpha, beta, and turn regions, Chou-Fasman algorithm (Chou and Fasman (1978) *Adv in Enzymol Mol* 47:45–148); hydrophilicity and hydrophobicity plots, Kyte-Doolittle algorithm (Kyte and Doolittle (1982) *J Mol Biol* 157:105–132); alpha amphipathic and beta amphipathic regions, Eisenberg algorithm (Eisenberg et al. (1982) *Nature* 299:371–374); flexible regions, Karplus-Schulz algorithm (Karplus and Schulz (1985) Naturwissens-Chafen 72:212–213); antigenic index, Jameson-Wolf algorithm (Jameson and Wolf (1988) CABIOS 4:121–136); surface probability plot, Emini algorithm (Emini et al. (1985) *J Virol* 55:836–839).

The CARK protein was aligned with the A. Thaliana kinase 2 (Accession No.Z97337), *A. Thaliana* kinase 3 (Accession No. AC003113), Arabidopsis thaliana (Accession No. AL031135), *C. elegans* kinase (Accession No. AF024491), D. discoideum protein tyrosine kinase (Accession No. A35670), *D. discoideum* protein tyrosine kinase (Accession No. U01064), *H. sapiens* serine/threonine kinase (Accession No. Z48615), human raf1 (Accession No. W13107), human Raf1 kinase (Accession No. R98215), and soybean kinase (Accession No. M67449) using the Clustal method with a PAM250 residue weight table. This alignment is shown in FIG. 3.

Tissue Distribution of CARK mRNA

This Example describes the tissue distribution of CARK mRNA, as determined by Northern blot hybridization.

Northern blot hybridization with the RNA sample was performed under standard conditions and washed under stringent conditions, i.e., 0.2×SSC at 65° C. A DNA probe corresponding to fchrf013f03 was used. The DNA was radioactively labeled with $^{32}P$ dCTP using the Prime-It kit (Stratagene, La Jolla, Calif.) according to the instructions of the supplier. Filters containing human mRNA, human muscle mRNA, and rat mRNA (MultiTissue Northern blots #7760-1, #7765-1, and #7764-1, respectively, from Clontech, Palo Alto, Calif.) were probed in ExpressHyb hybridization solution (Clontech) and washed at high stringency conditions according to the manufacturer's recommendations.

On the human mRNA blot which contained mRNA from heart, brain, placenta, lung, liver, skeletal muscle, kidney, and pancreas, CARK message was strongly detected in heart and faintly in skeletal muscle. On the human muscle mRNA blot which contained mRNA from skeletal muscle, uterus, colon, small intestine, bladder, heart, stomach, and prostate, CARK message was strongly detected in the heart. On the rat mRNA blot which contained mRNA from heart, brain, spleen, lung, liver, skeletal muscle, kidney and testis, CARK message was strongly detected in the heart.

Example 2

Expression of Recombinant CARK Protein in Bacterial Cells

In this example, CARK is expressed as a recombinant glutathione-S-transferase (GST) fusion polypeptide in *E.*

*coli* and the fusion polypeptide is isolated and characterized. Specifically, CARK is fused to GST and this fusion polypeptide is expressed in *E. coli*, e.g., strain PEB199. Expression of the GST-CARK fusion protein in PEB199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 3
Expression of Recombinant CARK Protein in COS Cells

To express the CARK gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire CARK protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the CARK DNA sequence is amplified by PCR using two primers. The 5' primer contains the restriction site of interest followed by approximately twenty nucleotides of the CARK coding sequence starting from the initiation codon; the 3' end sequence contains complementary sequences to the other restriction site of interest, a translation stop codon, the HA tag or FLAG tag and the last 20 nucleotides of the CARK coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the CARK gene is inserted in the correct orientation. The ligation mixture is transformed into *E. coli* cells (strains HB 101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the CARK-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. The expression of the CARK polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the CARK coding sequence is cloned directly into the polylinker of the pCDNA/Amp vector using the appropriate restriction sites. The resulting plasmid is transfected into COS cells in the manner described above, and the expression of the CARK polypeptide is detected by radiolabelling and immunoprecipitation using a CARK specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. An isolated nucleic acid molecule comprising the nucleotide sequence set forth in SEQ ID NO:1, or a complement thereof.

2. An isolated nucleic acid molecule comprising the nucleotide sequence set forth in SEQ ID NO:3, or a complement thereof.

3. An isolated nucleic acid molecule consisting of the nucleotide sequence set forth in SEQ ID NO:1, or a complement thereof.

4. An isolated nucleic acid molecule consisting of the nucleotide sequence set forth in SEQ ID NO:3, or a complement thereof.

5. An isolated nucleic acid molecule which encodes a polypeptide comprising the amino acid sequence set forth in SEQ ID NO:2, or a complement thereof.

6. An isolated nucleic acid molecule which encodes a polypeptide consisting of the amino acid sequence set forth in SEQ ID NO:2, or a complement thereof.

7. An isolated nucleic acid molecule comprising the nucleotide sequence contained in the plasmid deposited with ATCC® as Accession Number PTA-1530, or a complement thereof.

8. An isolated nucleic acid molecule which encodes a naturally occurring allelic variant of a polypeptide comprising the amino acid sequence of SEQ ID NO:2, , wherein the nucleic acid molecule hybridizes to a complement of a nucleic acid molecule consisting of SEQ ID NO:1 or 3 at 6×SSC at 45° C., followed by one or more washes in 0.2×SSC, 0.1% SDS at 50–65° C.

9. An isolated nucleic acid molecule which encodes a naturally occurring allelic variant of a polypeptide consisting of the amino acid sequence of SEQ ID NO:2, wherein the nucleic acid molecule hybridizes to a complement of a nucleic acid molecule consisting of SEQ ID NO:1 or 3 at 6×SSC at 45° C., followed by one or more washes in 0.2×SSC, 0.1% SDS at 50–65° C.

10. An isolated nucleic acid molecule comprising a nucleotide sequence which is at least 90% identical to the nucleotide sequence of SEQ ID NO:1 or 3, or a complement thereof.

11. An isolated nucleic acid molecule consisting of a nucleotide sequence which is at least 90% identical to the nucleotide sequence of SEQ ID NO:1 or 3, or a complement thereof.

12. An isolated nucleic acid molecule which encodes a polypeptide comprising an amino acid sequence at least about 90% identical to the amino acid sequence of SEQ ID NO:2.

13. An isolated nucleic acid molecule which encodes a polypeptide consisting of an amino acid sequence at least about 90% identical to the amino acid sequence of SEQ ID NO:2.

14. An isolated nucleic acid molecule comprising the nucleic acid molecule of claim 1, and a nucleotide sequence encoding a heterologous polypeptide.

15. A vector comprising the nucleic acid molecule of claim 1.

16. The vector of claim 15, which is an expression vector.

17. An isolated host cell transfected with the vector of claim 15.

18. A method of expressing a polypeptide comprising the step of culturing the isolated host cell of claim 17 under conditions in which the nucleic acid molecule is expressed, thereby expressing the polypeptide.

19. A method of producing a polypeptide comprising the step of culturing the isolated host cell of claim 17 under conditions in which the nucleic acid molecule is expressed and isolating said polypeptide from the culture medium.

20. A kit comprising the nucleic acid molecule of claim 1 and instructions for use.

21. An isolated nucleic acid molecule comprising the nucleic acid molecule of claim 2, and a nucleotide sequence encoding a heterologous polypeptide.

22. An isolated nucleic acid molecule comprising the nucleic acid molecule of claim 3, and a nucleotide sequence encoding a heterologous polypeptide.

23. An isolated nucleic acid molecule comprising the nucleic acid molecule of claim 4, and a nucleotide sequence encoding a heterologous polypeptide.

24. An isolated nucleic acid molecule comprising the nucleic acid molecule of claim 5, and a nucleotide sequence encoding a heterologous polypeptide.

25. An isolated nucleic acid molecule comprising the nucleic acid molecule of claim 6, and a nucleotide sequence encoding a heterologous polypeptide.

26. An isolated nucleic acid molecule comprising the nucleic acid molecule of claim 7, and a nucleotide sequence encoding a heterologous polypeptide.

27. An isolated nucleic acid molecule comprising the nucleic acid molecule of claim 8, and a nucleotide sequence encoding -a heterologous polypeptide.

28. An isolated nucleic acid molecule comprising the nucleic acid molecule of claim 9, and a nucleotide sequence encoding a heterologous polypeptide.

29. An isolated nucleic acid molecule comprising the nucleic acid molecule of claim 10, and a nucleotide sequence encoding a heterologous polypeptide.

30. An isolated nucleic acid molecule comprising the nucleic acid molecule of claim 11, and a nucleotide sequence encoding a heterologous polypeptide.

31. An isolated nucleic acid molecule comprising the nucleic acid molecule of claim 12, and a nucleotide sequence encoding a heterologous polypeptide.

32. An isolated nucleic acid molecule comprising the nucleic acid molecule of claim 13, and a nucleotide sequence encoding a heterologous polypeptide.

33. A vector comprising the nucleic acid molecule of claim 2.

34. The vector of claim 33, which is an expression vector.

35. An isolated host cell transfected with the vector of claim 33.

36. A method of expressing a polypeptide comprising the step of culturing the isolated host cell of claim 35 under conditions in which the nucleic acid molecule is expressed, thereby expressing the polypeptide.

37. A method gf producing a polypeptide comprising the step of culturing the isolated host cell of claim 35 under conditions in which the nucleic acid molecule is expressed and isolating said polypeptide from the culture medium.

38. A vector comprising the nucleic acid molecule of claim 3.

39. The vector of claim 38, which is an expression vector.

40. An isolated host cell transfected with the vector of claim 38.

41. A method of expressing a polypeptide comprising the step of culturing the isolated host cell of claim 40 under conditions in which the nucleic acid molecule is expressed, thereby expressing the polypeptide.

42. A method Qfproducing a polypeptide comprising the step of culturing the isolated host cell of claim 40 under conditions in which the nucleic acid molecule is expressed and isolating said polypeptide from the culture medium.

43. A vector comprising the nucleic acid molecule of claim 4.

44. The vector of claim 43, which is an expression vector.

45. An isolated host cell transfected with the vector of claim 43.

46. A method of expressing a polypeptide comprising the step of culturing the isolated host cell of claim 45 under conditions in which the nucleic acid molecule is expressed, thereby expressing the polypeptide.

47. A method gf producing a polypeptide comprising the step of culturing the isolated host cell of claim 45 under conditions in which the nucleic acid molecule is expressed and isolating said polypeptide from the culture medium.

48. A vector comprising the nucleic acid molecule of claim 5.

49. The vector of claim 48, which is an expression vector.

50. An isolated host cell transfected with the vector of claim 48.

51. A method of expressing a polypeptide comprising the step of culturing the isolated host cell of claim 50 under conditions in which the nucleic acid molecule is expressed, thereby expressing the polypeptide.

52. A method Qf producing a polypeptide comprising the step of culturing the isolated host cell of claim 50 under conditions in which the nucleic acid molecule is expressed and isolating said polypeptide from the culture medium.

53. A vector comprising the nucleic acid molecule of claim 6.

54. The vector of claim 53, which is an expression vector.

55. An isolated host cell transfected with the vector of claim 53.

56. A method of expressing a polypeptide comprising the step of culturing the isolated host cell of claim 55 under conditions in which the nucleic acid molecule is expressed, thereby expressing the polypeptide.

57. A method of producing a polypeptide comprising the step of culturing the isolated host cell of claim 55 under conditions in which the nucleic acid molecule is expressed and isolating said polypeptide from the culture medium.

58. A vector comprising the nucleic acid molecule of claim 7.

59. The vector of claim 58, which is an expression vector.

60. An isolated host cell transfected with the vector of claim 58.

61. A method of expressing a polypeptide comprising the step of culturing the isolated host cell of claim 60 under conditions in which the nucleic acid molecule is expressed, thereby expressing the polypeptide.

62. A method of producing a polypeptide comprising the step of culturing the isolated host cell of claim 60 under conditions in which the nucleic acid molecule is expressed and isolating said polypeptide from the culture medium.

63. A vector comprising the nucleic acid molecule of claim 8.

64. The vector of claim 63, which is an expression vector.

65. An isolated host cell transfected with the vector of claim 63.

66. A method of expressing a polypeptide comprising the step of culturing the isolated host cell of claim 65 under conditions in which the nucleic acid molecule is expressed, thereby expressing the polypeptide.

67. A method of producing a polypeptide comprising the step of culturing the isolated host cell of claim 65 under conditions in which the nucleic acid molecule is expressed and isolating said polypeptide from the culture medium.

68. A vector comprising the nucleic acid molecule of claim 9.

69. The vector of claim 68, which is an expression vector.

70. An isolated host cell transfected with the vector of claim 68.

71. A method of expressing a polypeptide comprising the step of culturing the isolated host cell of claim 70 under conditions in which the nucleic acid molecule is expressed, thereby expressing the polypeptide.

72. A method of producing a polypeptide comprising the step of culturing the isolated host cell of claim 70 under conditions in which the nucleic acid molecule is expressed and isolating said polypeptide from the culture medium.

73. A vector comprising the nucleic acid molecule of claim 10.

74. The vector of claim 73, which is an expression vector.

75. An isolated host cell transfected with the vector of claim 73.

76. A method of expressing a polypeptide comprising the step of culturing the isolated host cell of claim 75 under conditions in which the nucleic acid molecule is expressed, thereby expressing the polypeptide.

77. A method gf producing a polypeptide comprising the step of culturing the isolated host cell of claim 75 under conditions in which the nucleic acid molecule is expressed and isolating said polypeptide from the culture medium.

78. A vector comprising the nucleic acid molecule of claim 11.

79. The vector of claim 78, which is an expression vector.

80. An isolated host cell transfected with the vector of claim 78.

81. A method of expressing a polypeptide comprising the step of culturing the isolated host cell of claim 80 Sunder conditions in which the nucleic acid molecule is expressed, thereby expressing the polypeptide.

82. A method of producing a polypeptide comprising the step of culturing the isolated host cell of claim 80 under conditions in which the nucleic acid molecule is expressed and isolating said polypeptide from the culture medium.

83. A vector comprising the nucleic acid molecule of claim 12.

84. The vector of claim 83, which is an expression vector.

85. An isolated host cell transfected with the vector of claim 83.

86. A method of expresng a polypeptide comprising the step of culturing the isolated host cell of claim 85 under conditions in which the nucleic acid molecule is expressed, thereby expressing the polypeptide.

87. A method producing a polypeptide comprising the step of culturing the isolated host cell of claim 85 under conditions in which the nucleic acid molecule is expressed and isolating said polypeptide from, the culture medium.

88. A vector comprising the nucleic acid molecule of claim 13.

89. The vector of claim 88, which is an expression vector.

90. An isolated host cell transfected with the vector of claim 88.

91. A method of expressing a polypeptide comprising the step of culturing the isolated host cell of claim 90 under conditions in which the nucleic acid molecule is expressed, thereby expressing the polypeptide.

92. A method of producing a polypeptide comprising the step of culturing the isolated host cell of claim 90 under conditions in which the nucleic acid molecule is expressed and isolating said polypeptide from the culture medium.

93. A kit comprising the nucleic acid molecule of claim 2 and instructions for use.

94. A kit comprising the nucleic acid molecule of claim 3 and instructions for use.

95. A kit comprising the nucleic acid molecule of claim 4 and instructions for use.

96. A kit comprising the nucleic acid molecule of claim 5 and instructions for use.

97. A kit comprising the nucleic acid molecule of claim 6 and instructions for use.

98. A kit comprising the nucleic acid molecule of claim 7 and instructions for use.

99. A kit comprising the nucleic acid molecule of claim 8 and instructions for use.

100. A kit comprising the nucleic acid molecule of claim 9 and instructions for use.

101. A kit comprising the nucleic acid molecule of claim 10 and instructions for use.

102. A kit comprising the nucleic acid molecule of claim 11 and instructions for use.

103. A kit comprising the nucleic acid molecule of claim 12 and instructions for use.

104. A kit comprising the nucleic acid molecule of claim 13 and instructions for use.

105. An isolated nucleic acid molecule comprising a nucleotide sequence which encodes a cardiac-ankyrin-repeat protein kinase polypeptide, wherein the nucleic acid molecule hybridizes to a complement of a nucleic acid molecule consisting of SEQ ID NO:1 or 3 at 6×SSC at 45° C., followed by one or more washes in 0.2×SSC, 0.1% SDS at 65° C.

106. An isolated nucleic acid molecule comprising a nucleotide sequence at least 350 nucleotides in length which encodes a polypeptide comprising a protein kinase domain, wherein the nucleotide sequence hybridizes to a complement of a nucleotide sequence consisting of SEQ ID NO:1 or 3 at 6×SSC at 45° C., followed by one or more washes in 0.2×SSC, 0.1% SDS at 65° C.

107. An isolated nucleic acid molecule comprising a nucleotide sequence which encodes a polypeptide comprising a protein kinase domain, wherein the nucleotide sequence hybridizes to a complement of a nucleotide sequence consisting of SEQ ID NO:1 or 3 at 6×SSC at 45° C., followed by one or more washes in 0.2×SSC, 0.1% SDS at 65° C.

108. An isolated nucleic acid molecule at least 350 nucleotides in length which encodes a cardiac-ankyrin-repeat protein kinase polypeptide, wherein the nucleic acid molecule hybridizes to a complement of a nucleic acid molecule consisting of SEQ ID NO:1 or 3 at 6×SSC at 45° C., followed by one or more washes in 0.2×SSC, 0.1% SDS at 65° C.

109. An isolated nucleic acid molecule comprising a nucleotide sequence which encodes a fragment of at least 120 contiguous amino acid residues of the amino acid sequence of SEQ ID NO:2, or a complement thereof.

110. An isolated nucleic acid molecule comprising a nucleotide sequence which encodes a polypeptide comprising amino acid residues 463 to 716 of SEQ ID NO:2, or a complement thereof.

* * * * *

SEQUENCE LISTING

<160> NUMBER OF SEQ ID NOS: 6

<210> SEQ ID NO: 1
<211> LENGTH: 3025
<212> TYPE: DNA
<213> ORGANISM: Homo sapiens
<220> FEATURE:
<221> NAME/KEY: CDS
<222> LOCATION: (48)..(2552)

<400> SEQUENCE: 1

```
gtcgacccac gcgtccggcc ctggagaaag gaagaaactt ataataa atg gga aat       56
                                                    Met Gly Asn
                                                      1 tat aaa tct aga cca acc caa act tgt act gat gaa tgg aag aaa aaa      104
Tyr Lys Ser Arg Pro Thr Gln Thr Cys Thr Asp Glu Trp Lys Lys Lys
      5                  10                  15 gtc agt gaa tca tat gtt atc aca ata gaa aga tta gaa gat gac ctg      152
Val Ser Glu Ser Tyr Val Ile Thr Ile Glu Arg Leu Glu Asp Asp Leu
 20                  25                  30                  35 cag atc aag gaa aaa gaa ctg aca gaa cta agg aat ata ttt ggc tct      200
```

```
Gln Ile Lys Glu Lys Glu Leu Thr Glu Leu Arg Asn Ile Phe Gly Ser
             40                  45                  50 gat gaa gcc ttc agt aaa gtc aat tta aat tac cgc act gaa aat ggg     248
Asp Glu Ala Phe Ser Lys Val Asn Leu Asn Tyr Arg Thr Glu Asn Gly
             55                  60                  65 ctg tct cta ctt cat tta tgt tgc att tgt gga ggc aag aaa tca cat     296
Leu Ser Leu Leu His Leu Cys Cys Ile Cys Gly Gly Lys Lys Ser His
         70                  75                  80 att cga act ctt atg ttg aaa ggg ctc cgc cca tct cga ctg aca aga     344
Ile Arg Thr Leu Met Leu Lys Gly Leu Arg Pro Ser Arg Leu Thr Arg
     85                  90                  95 aat gga ttt aca gcc ttg cat tta gca gtt tac aag gat aat gca gaa     392
Asn Gly Phe Thr Ala Leu His Leu Ala Val Tyr Lys Asp Asn Ala Glu
100                 105                 110                 115 ttg atc act tct ctg ctt cac agt gga gct gat ata cag cag gtt gga     440
Leu Ile Thr Ser Leu Leu His Ser Gly Ala Asp Ile Gln Gln Val Gly
             120                 125                 130 tac ggt ggc ctc act gcc ctc cat att gct aca ata gct ggc cac cta     488
Tyr Gly Gly Leu Thr Ala Leu His Ile Ala Thr Ile Ala Gly His Leu
             135                 140                 145 gag gct gct gat gtg ctg ttg caa cat gga gct aat gtc aat att caa     536
Glu Ala Ala Asp Val Leu Leu Gln His Gly Ala Asn Val Asn Ile Gln
         150                 155                 160 gat gca gtt ttt ttc act cca ttg cat att gca gcg tac tat gga cat     584
Asp Ala Val Phe Phe Thr Pro Leu His Ile Ala Ala Tyr Tyr Gly His
     165                 170                 175 gaa cag gta act cgc ctt ctt ttg aaa ttt ggt gct gat gta aat gta     632
Glu Gln Val Thr Arg Leu Leu Leu Lys Phe Gly Ala Asp Val Asn Val
180                 185                 190                 195 agt ggt gaa gtt gga gat aga ccc ctc cac cta gca tct gca aaa gga     680
Ser Gly Glu Val Gly Asp Arg Pro Leu His Leu Ala Ser Ala Lys Gly
             200                 205                 210 ttc ttg aat att gca aaa ctc ttg atg gaa gaa ggc agc aaa gca gat     728
Phe Leu Asn Ile Ala Lys Leu Leu Met Glu Glu Gly Ser Lys Ala Asp
             215                 220                 225 gtg aat gct caa gat aat gaa gac cat gtc cca ctc cat ttc tgt tct     776
Val Asn Ala Gln Asp Asn Glu Asp His Val Pro Leu His Phe Cys Ser
         230                 235                 240 cga ttt gga cac cat gat ata gtt aag tat ctg ctg caa agt gat ttg     824
Arg Phe Gly His His Asp Ile Val Lys Tyr Leu Leu Gln Ser Asp Leu
245                 250                 255 gaa gtt caa cct cat gtt gtt aat atc tat gga gat acc ccc tta cac     872
Glu Val Gln Pro His Val Val Asn Ile Tyr Gly Asp Thr Pro Leu His
260                 265                 270                 275 ctg gca tgc tac aat ggc aaa ttt gaa gtt gcc aag gaa atc atc caa     920
Leu Ala Cys Tyr Asn Gly Lys Phe Glu Val Ala Lys Glu Ile Ile Gln
             280                 285                 290 ata tca gga aca gaa agt ctg act aag gaa aac atc ttc agt gaa aca     968
Ile Ser Gly Thr Glu Ser Leu Thr Lys Glu Asn Ile Phe Ser Glu Thr
             295                 300                 305 gct ttt cat agt gct tgt acc tat ggc aag agc att gac cta gtc aaa     1016
Ala Phe His Ser Ala Cys Thr Tyr Gly Lys Ser Ile Asp Leu Val Lys
         310                 315                 320 ttt ctt ctt gat cag aat gtc ata aac atc aac cac caa gga agg gat     1064
Phe Leu Leu Asp Gln Asn Val Ile Asn Ile Asn His Gln Gly Arg Asp
     325                 330                 335 ggg cac act gga tta cac tct gct tgc tac cac ggt cac att cgc ctg     1112
Gly His Thr Gly Leu His Ser Ala Cys Tyr His Gly His Ile Arg Leu
340                 345                 350                 355
```

-continued

| | | |
|---|---|---|
| gtt cag ttc tta ctg gat aat gga gct gat atg aat cta gtg gct tgt<br>Val Gln Phe Leu Leu Asp Asn Gly Ala Asp Met Asn Leu Val Ala Cys<br>                                  360                              365                      370 | 1160 |
| gat ccc agc agg tct agt ggt gaa aaa gat gag cag aca tgt ttg atg<br>Asp Pro Ser Arg Ser Ser Gly Glu Lys Asp Glu Gln Thr Cys Leu Met<br>                   375                                380                            385 | 1208 |
| tgg gct tat gaa aaa ggg cat gat gcc att gtc aca ctc ctg aag cat<br>Trp Ala Tyr Glu Lys Gly His Asp Ala Ile Val Thr Leu Leu Lys His<br>         390                                395                            400 | 1256 |
| tat aag aga cca caa gat gaa ttg ccc tgt aat gaa tat tct cag cct<br>Tyr Lys Arg Pro Gln Asp Glu Leu Pro Cys Asn Glu Tyr Ser Gln Pro<br>405                              410                              415 | 1304 |
| gga gga gat ggc tcc tat gtg tct gtt cca tca ccc ttg gga aag att<br>Gly Gly Asp Gly Ser Tyr Val Ser Val Pro Ser Pro Leu Gly Lys Ile<br>420                          425                              430                        435 | 1352 |
| aaa agc atg aca aaa gag aag gca gat att ctc ctc cta aga gct gga<br>Lys Ser Met Thr Lys Glu Lys Ala Asp Ile Leu Leu Leu Arg Ala Gly<br>                   440                                445                            450 | 1400 |
| ttg cct tca cat ttc cat ctt cag ctc tca gaa att gag ttc cat gag<br>Leu Pro Ser His Phe His Leu Gln Leu Ser Glu Ile Glu Phe His Glu<br>         455                                460                            465 | 1448 |
| att att ggc tca ggt tct ttt ggg aaa gta tat aaa gga cga tgc aga<br>Ile Ile Gly Ser Gly Ser Phe Gly Lys Val Tyr Lys Gly Arg Cys Arg<br>                   470                                475                            480 | 1496 |
| aat aaa ata gtg gct ata aaa cgt tat cga gcc aat acc tac tgc tcc<br>Asn Lys Ile Val Ala Ile Lys Arg Tyr Arg Ala Asn Thr Tyr Cys Ser<br>485                              490                              495 | 1544 |
| aag tca gat gtg gat atg ttt tgc cga gag gtg tcc att ctc tgc cag<br>Lys Ser Asp Val Asp Met Phe Cys Arg Glu Val Ser Ile Leu Cys Gln<br>500                              505                              510                       515 | 1592 |
| ctc aat cat ccc tgc gta att cag ttt gtg ggt gct tgc ttg aat gat<br>Leu Asn His Pro Cys Val Ile Gln Phe Val Gly Ala Cys Leu Asn Asp<br>                   520                                525                            530 | 1640 |
| ccc agc cag ttt gcc att gtc act caa tac ata tca ggg ggt tct ctg<br>Pro Ser Gln Phe Ala Ile Val Thr Gln Tyr Ile Ser Gly Gly Ser Leu<br>         535                                540                            545 | 1688 |
| ttc tcc ctc ctt cat gag cag aag agg att ctt gat ttg cag tct aaa<br>Phe Ser Leu Leu His Glu Gln Lys Arg Ile Leu Asp Leu Gln Ser Lys<br>                   550                                555                            560 | 1736 |
| tta att att gca gta gat gtt gcc aaa ggc atg gag tac ctt cac aac<br>Leu Ile Ile Ala Val Asp Val Ala Lys Gly Met Glu Tyr Leu His Asn<br>565                              570                              575 | 1784 |
| ctg aca cag cca att ata cat cgt gac ttg aac agt cac aat att ctt<br>Leu Thr Gln Pro Ile Ile His Arg Asp Leu Asn Ser His Asn Ile Leu<br>580                              585                              590                       595 | 1832 |
| ctc tat gag gat ggg cat gct gtg gtg gca gat ttt gga gaa tca aga<br>Leu Tyr Glu Asp Gly His Ala Val Val Ala Asp Phe Gly Glu Ser Arg<br>                   600                                605                            610 | 1880 |
| ttt cta cag tct ctg gat gaa gac aac atg aca aaa caa cct ggg aac<br>Phe Leu Gln Ser Leu Asp Glu Asp Asn Met Thr Lys Gln Pro Gly Asn<br>                   615                                620                            625 | 1928 |
| ctc cgt tgg atg gct cct gag gtg ttc acg cag tgc act cgg tac acc<br>Leu Arg Trp Met Ala Pro Glu Val Phe Thr Gln Cys Thr Arg Tyr Thr<br>         630                                635                            640 | 1976 |
| atc aaa gca gat gtc ttc agc tat gct ctg tgt ctg tgg gaa att ctc<br>Ile Lys Ala Asp Val Phe Ser Tyr Ala Leu Cys Leu Trp Glu Ile Leu<br>645                              650                              655 | 2024 |
| act ggc gaa att cca ttc gct cat ctc aag cca gcg gct gcg gca gca<br>Thr Gly Glu Ile Pro Phe Ala His Leu Lys Pro Ala Ala Ala Ala Ala<br>660                              665                              670                       675 | 2072 |

-continued

```
gac atg gct tac cac cac atc aga cct ccc att ggc tat tcc att ccc    2120
Asp Met Ala Tyr His His Ile Arg Pro Pro Ile Gly Tyr Ser Ile Pro
            680                 685                 690 aag ccc ata tca tct ctg ctg ata cga ggg tgg aac gca tgt cct gaa    2168
Lys Pro Ile Ser Ser Leu Leu Ile Arg Gly Trp Asn Ala Cys Pro Glu
                695                 700                 705 gga aga ccc gaa ttt tct gaa gtt gtc atg aag tta gaa gag tgt ctc    2216
Gly Arg Pro Glu Phe Ser Glu Val Val Met Lys Leu Glu Glu Cys Leu
            710                 715                 720 tgc aac att gag ctg atg tct cct gca tca agt aac agc agt ggg tct    2264
Cys Asn Ile Glu Leu Met Ser Pro Ala Ser Ser Asn Ser Ser Gly Ser
        725                 730                 735 ctc tca cct tct tct tct tct gat tgc ctg gtg aac cgg gga gga cct    2312
Leu Ser Pro Ser Ser Ser Ser Asp Cys Leu Val Asn Arg Gly Gly Pro
    740                 745                 750                 755 gc cgg agt cat gtg gca gca tta aga agt cgt ttc gaa ttg gaa tat     2360
Gly Arg Ser His Val Ala Ala Leu Arg Ser Arg Phe Glu Leu Glu Tyr
            760                 765                 770 gct cta aat gca agg tcc tat gct gct ttg tcc caa agt gct gga caa    2408
Ala Leu Asn Ala Arg Ser Tyr Ala Ala Leu Ser Gln Ser Ala Gly Gln
        775                 780                 785 tat tcc tct caa ggt ctg tct ttg gag gag atg aaa aga agt ctt caa    2456
Tyr Ser Ser Gln Gly Leu Ser Leu Glu Glu Met Lys Arg Ser Leu Gln
    790                 795                 800 tac aca ccc att gac aaa tat ggc tat gta tcc gat ccc atg agc tca    2504
Tyr Thr Pro Ile Asp Lys Tyr Gly Tyr Val Ser Asp Pro Met Ser Ser
805                 810                 815 atg cat ttt cat tct tgc cga aat agt agc agc ttt gag gac agc agc    2552
Met His Phe His Ser Cys Arg Asn Ser Ser Ser Phe Glu Asp Ser Ser
820                 825                 830                 835 tgacagcatt cggcgtatac ctaaggagag ttttttcccc gaactgacag caacgattcc   2612
aaccacggca agctggcttc caactataac attttactct caaaggtctc cttaaattgg   2672
gcttgttttt acttgtccta tttaattccc cactattagc aggctttgga tttgtgccta   2732
aggaataata tgcaaaagaa ccaagacaga atgtatatga agaattgttt ttaattttgt   2792
aaattaaaaa aaaatttaga tcgttacttg gaaatggagc ctaagtctgt ggtggacaga   2852
taataattat gttttcctgg gctgaattat gtagacttgt gtttgacagc tatgggttta   2912
tttcttagaa cattgttcat tttcttttct cattatgtta cttctagtgt tcacctctgt   2972
gattaaagat tctttggtga aatagaaaaa aaaaaaaaaa aaagggcggc cgc          3025
```

<210> SEQ ID NO: 2
<211> LENGTH: 835
<212> TYPE: PRT
<213> ORGANISM: Homo sapiens

<400> SEQUENCE: 2

```
Met Gly Asn Tyr Lys Ser Arg Pro Thr Gln Thr Cys Thr Asp Glu Trp
1               5                   10                  15

Lys Lys Lys Val Ser Glu Ser Tyr Val Ile Thr Ile Glu Arg Leu Glu
            20                  25                  30

Asp Asp Leu Gln Ile Lys Glu Lys Glu Leu Thr Glu Leu Arg Asn Ile
        35                  40                  45

Phe Gly Ser Asp Glu Ala Phe Ser Lys Val Asn Leu Asn Tyr Arg Thr
    50                  55                  60

Glu Asn Gly Leu Ser Leu Leu His Leu Cys Cys Ile Cys Gly Gly Lys
65                  70                  75                  80
```

```
Lys Ser His Ile Arg Thr Leu Met Leu Lys Gly Leu Arg Pro Ser Arg
                 85                  90                  95

Leu Thr Arg Asn Gly Phe Thr Ala Leu His Leu Ala Val Tyr Lys Asp
            100                 105                 110

Asn Ala Glu Leu Ile Thr Ser Leu Leu His Ser Gly Ala Asp Ile Gln
        115                 120                 125

Gln Val Gly Tyr Gly Gly Leu Thr Ala Leu His Ile Ala Thr Ile Ala
    130                 135                 140

Gly His Leu Glu Ala Ala Asp Val Leu Gln His Gly Ala Asn Val
145                 150                 155                 160

Asn Ile Gln Asp Ala Val Phe Phe Thr Pro Leu His Ile Ala Ala Tyr
                165                 170                 175

Tyr Gly His Glu Gln Val Thr Arg Leu Leu Leu Lys Phe Gly Ala Asp
                180                 185                 190

Val Asn Val Ser Gly Glu Val Gly Asp Arg Pro Leu His Leu Ala Ser
            195                 200                 205

Ala Lys Gly Phe Leu Asn Ile Ala Lys Leu Leu Met Glu Gly Gly Ser
    210                 215                 220

Lys Ala Asp Val Asn Ala Gln Asp Asn Glu Asp His Val Pro Leu His
225                 230                 235                 240

Phe Cys Ser Arg Phe Gly His His Asp Ile Val Lys Tyr Leu Leu Gln
                245                 250                 255

Ser Asp Leu Glu Val Gln Pro His Val Val Asn Ile Tyr Gly Asp Thr
            260                 265                 270

Pro Leu His Leu Ala Cys Tyr Asn Gly Lys Phe Glu Val Ala Lys Glu
        275                 280                 285

Ile Ile Gln Ile Ser Gly Thr Glu Ser Leu Thr Lys Glu Asn Ile Phe
    290                 295                 300

Ser Glu Thr Ala Phe His Ser Ala Cys Thr Tyr Gly Lys Ser Ile Asp
305                 310                 315                 320

Leu Val Lys Phe Leu Leu Asp Gln Asn Val Ile Asn Ile Asn His Gln
                325                 330                 335

Gly Arg Asp Gly His Thr Gly Leu His Ser Ala Cys Tyr His Gly His
            340                 345                 350

Ile Arg Leu Val Gln Phe Leu Leu Asp Asn Gly Ala Asp Met Asn Leu
        355                 360                 365

Val Ala Cys Asp Pro Ser Arg Ser Ser Gly Glu Lys Asp Glu Gln Thr
    370                 375                 380

Cys Leu Met Trp Ala Tyr Glu Lys Gly His Asp Ala Ile Val Thr Leu
385                 390                 395                 400

Leu Lys His Tyr Lys Arg Pro Gln Asp Glu Leu Pro Cys Asn Glu Tyr
                405                 410                 415

Ser Gln Pro Gly Gly Asp Gly Ser Tyr Val Ser Val Pro Ser Pro Leu
            420                 425                 430

Gly Lys Ile Lys Ser Met Thr Lys Glu Lys Ala Asp Ile Leu Leu Leu
        435                 440                 445

Arg Ala Gly Leu Pro Ser His Phe His Leu Gln Leu Ser Glu Ile Glu
    450                 455                 460

Phe His Glu Ile Ile Gly Ser Gly Ser Phe Gly Lys Val Tyr Lys Gly
465                 470                 475                 480

Arg Cys Arg Asn Lys Ile Val Ala Ile Lys Arg Tyr Arg Ala Asn Thr
                485                 490                 495
```

```
Tyr Cys Ser Lys Ser Asp Val Asp Met Phe Cys Arg Glu Val Ser Ile
            500                 505                 510
Leu Cys Gln Leu Asn His Pro Cys Val Ile Gln Phe Val Gly Ala Cys
            515                 520                 525
Leu Asn Asp Pro Ser Gln Phe Ala Ile Val Thr Gln Tyr Ile Ser Gly
            530                 535                 540
Gly Ser Leu Phe Ser Leu Leu His Glu Gln Lys Arg Ile Leu Asp Leu
545                 550                 555                 560
Gln Ser Lys Leu Ile Ile Ala Val Asp Val Ala Lys Gly Met Glu Tyr
                565                 570                 575
Leu His Asn Leu Thr Gln Pro Ile Ile His Arg Asp Leu Asn Ser His
            580                 585                 590
Asn Ile Leu Leu Tyr Glu Asp Gly His Ala Val Val Ala Asp Phe Gly
            595                 600                 605
Glu Ser Arg Phe Leu Gln Ser Leu Asp Glu Asp Asn Met Thr Lys Gln
            610                 615                 620
Pro Gly Asn Leu Arg Trp Met Ala Pro Glu Val Phe Thr Gln Cys Thr
625                 630                 635                 640
Arg Tyr Thr Ile Lys Ala Asp Val Phe Ser Tyr Ala Leu Cys Leu Trp
                645                 650                 655
Glu Ile Leu Thr Gly Glu Ile Pro Phe Ala His Leu Lys Pro Ala Ala
                660                 665                 670
Ala Ala Ala Asp Met Ala Tyr His His Ile Arg Pro Pro Ile Gly Tyr
            675                 680                 685
Ser Ile Pro Lys Pro Ile Ser Ser Leu Leu Ile Arg Gly Trp Asn Ala
            690                 695                 700
Cys Pro Glu Gly Arg Pro Glu Phe Ser Glu Val Val Met Lys Leu Glu
705                 710                 715                 720
Glu Cys Leu Cys Asn Ile Glu Leu Met Ser Pro Ala Ser Ser Asn Ser
                725                 730                 735
Ser Gly Ser Leu Ser Pro Ser Ser Ser Asp Cys Leu Val Asn Arg
            740                 745                 750
Gly Gly Pro Gly Arg Ser His Val Ala Ala Leu Arg Ser Arg Phe Glu
            755                 760                 765
Leu Glu Tyr Ala Leu Asn Ala Arg Ser Tyr Ala Ala Leu Ser Gln Ser
            770                 775                 780
Ala Gly Gln Tyr Ser Ser Gln Gly Leu Ser Leu Glu Glu Met Lys Arg
785                 790                 795                 800
Ser Leu Gln Tyr Thr Pro Ile Asp Lys Tyr Gly Tyr Val Ser Asp Pro
                805                 810                 815
Met Ser Ser Met His Phe His Ser Cys Arg Asn Ser Ser Ser Phe Glu
            820                 825                 830
Asp Ser Ser
        835

<210> SEQ ID NO: 3
<211> LENGTH: 2505
<212> TYPE: DNA
<213> ORGANISM: Homo sapiens
<220> FEATURE:
<221> NAME/KEY: CDS
<222> LOCATION: (1)..(2505)

<400> SEQUENCE: 3 atg gga aat tat aaa tct aga cca acc caa act tgt act gat gaa tgg     48
Met Gly Asn Tyr Lys Ser Arg Pro Thr Gln Thr Cys Thr Asp Glu Trp
```

-continued

| | 1 | | | | 5 | | | | 10 | | | | 15 | | | |
|---|---|---|---|---|---|---|---|---|---|---|---|---|---|---|---|---|
| aag | aaa | aaa | gtc | agt | gaa | tca | tat | gtt | atc | aca | ata | gaa | aga | tta | gaa | 96 |
| Lys | Lys | Lys | Val | Ser | Glu | Ser | Tyr | Val | Ile | Thr | Ile | Glu | Arg | Leu | Glu | |
| | | | 20 | | | | 25 | | | | 30 | | | | | |

| gat | gac | ctg | cag | atc | aag | gaa | aaa | gaa | ctg | aca | gaa | cta | agg | aat | ata | 144 |
|---|---|---|---|---|---|---|---|---|---|---|---|---|---|---|---|---|
| Asp | Asp | Leu | Gln | Ile | Lys | Glu | Lys | Glu | Leu | Thr | Glu | Leu | Arg | Asn | Ile | |
| | | 35 | | | | 40 | | | | 45 | | | | | | |

| ttt | ggc | tct | gat | gaa | gcc | ttc | agt | aaa | gtc | aat | tta | aat | tac | cgc | act | 192 |
|---|---|---|---|---|---|---|---|---|---|---|---|---|---|---|---|---|
| Phe | Gly | Ser | Asp | Glu | Ala | Phe | Ser | Lys | Val | Asn | Leu | Asn | Tyr | Arg | Thr | |
| 50 | | | | | 55 | | | | | 60 | | | | | | |

| gaa | aat | ggg | ctg | tct | cta | ctt | cat | tta | tgt | tgc | att | tgt | gga | ggc | aag | 240 |
|---|---|---|---|---|---|---|---|---|---|---|---|---|---|---|---|---|
| Glu | Asn | Gly | Leu | Ser | Leu | Leu | His | Leu | Cys | Cys | Ile | Cys | Gly | Gly | Lys | |
| 65 | | | | 70 | | | | | 75 | | | | | 80 | | |

| aaa | tca | cat | att | cga | act | ctt | atg | ttg | aaa | ggg | ctc | cgc | cca | tct | cga | 288 |
|---|---|---|---|---|---|---|---|---|---|---|---|---|---|---|---|---|
| Lys | Ser | His | Ile | Arg | Thr | Leu | Met | Leu | Lys | Gly | Leu | Arg | Pro | Ser | Arg | |
| | | | 85 | | | | | 90 | | | | | 95 | | | |

| ctg | aca | aga | aat | gga | ttt | aca | gcc | ttg | cat | tta | gca | gtt | tac | aag | gat | 336 |
|---|---|---|---|---|---|---|---|---|---|---|---|---|---|---|---|---|
| Leu | Thr | Arg | Asn | Gly | Phe | Thr | Ala | Leu | His | Leu | Ala | Val | Tyr | Lys | Asp | |
| | | | 100 | | | | | 105 | | | | | 110 | | | |

| aat | gca | gaa | ttg | atc | act | tct | ctg | ctt | cac | agt | gga | gct | gat | ata | cag | 384 |
|---|---|---|---|---|---|---|---|---|---|---|---|---|---|---|---|---|
| Asn | Ala | Glu | Leu | Ile | Thr | Ser | Leu | Leu | His | Ser | Gly | Ala | Asp | Ile | Gln | |
| | | 115 | | | | | 120 | | | | | 125 | | | | |

| cag | gtt | gga | tac | ggt | ggc | ctc | act | gcc | ctc | cat | att | gct | aca | ata | gct | 432 |
|---|---|---|---|---|---|---|---|---|---|---|---|---|---|---|---|---|
| Gln | Val | Gly | Tyr | Gly | Gly | Leu | Thr | Ala | Leu | His | Ile | Ala | Thr | Ile | Ala | |
| | 130 | | | | | 135 | | | | | 140 | | | | | |

| ggc | cac | cta | gag | gct | gct | gat | gtg | ctg | ttg | caa | cat | gga | gct | aat | gtc | 480 |
|---|---|---|---|---|---|---|---|---|---|---|---|---|---|---|---|---|
| Gly | His | Leu | Glu | Ala | Ala | Asp | Val | Leu | Leu | Gln | His | Gly | Ala | Asn | Val | |
| 145 | | | | | 150 | | | | | 155 | | | | | 160 | |

| aat | att | caa | gat | gca | gtt | ttt | ttc | act | cca | ttg | cat | att | gca | gcg | tac | 528 |
|---|---|---|---|---|---|---|---|---|---|---|---|---|---|---|---|---|
| Asn | Ile | Gln | Asp | Ala | Val | Phe | Phe | Thr | Pro | Leu | His | Ile | Ala | Ala | Tyr | |
| | | | | 165 | | | | | 170 | | | | | 175 | | |

| tat | gga | cat | gaa | cag | gta | act | cgc | ctt | ctt | ttg | aaa | ttt | ggt | gct | gat | 576 |
|---|---|---|---|---|---|---|---|---|---|---|---|---|---|---|---|---|
| Tyr | Gly | His | Glu | Gln | Val | Thr | Arg | Leu | Leu | Leu | Lys | Phe | Gly | Ala | Asp | |
| | | | 180 | | | | | 185 | | | | | 190 | | | |

| gta | aat | gta | agt | ggt | gaa | gtt | gga | gat | aga | ccc | ctc | cac | cta | gca | tct | 624 |
|---|---|---|---|---|---|---|---|---|---|---|---|---|---|---|---|---|
| Val | Asn | Val | Ser | Gly | Glu | Val | Gly | Asp | Arg | Pro | Leu | His | Leu | Ala | Ser | |
| | | | 195 | | | | | 200 | | | | | 205 | | | |

| gca | aaa | gga | ttc | ttg | aat | att | gca | aaa | ctc | ttg | atg | gaa | gaa | ggc | agc | 672 |
|---|---|---|---|---|---|---|---|---|---|---|---|---|---|---|---|---|
| Ala | Lys | Gly | Phe | Leu | Asn | Ile | Ala | Lys | Leu | Leu | Met | Glu | Glu | Gly | Ser | |
| | 210 | | | | | 215 | | | | | 220 | | | | | |

| aaa | gca | gat | gtg | aat | gct | caa | gat | aat | gaa | gac | cat | gtc | cca | ctc | cat | 720 |
|---|---|---|---|---|---|---|---|---|---|---|---|---|---|---|---|---|
| Lys | Ala | Asp | Val | Asn | Ala | Gln | Asp | Asn | Glu | Asp | His | Val | Pro | Leu | His | |
| 225 | | | | | 230 | | | | | 235 | | | | | 240 | |

| ttc | tgt | tct | cga | ttt | gga | cac | cat | gat | ata | gtt | aag | tat | ctg | ctg | caa | 768 |
|---|---|---|---|---|---|---|---|---|---|---|---|---|---|---|---|---|
| Phe | Cys | Ser | Arg | Phe | Gly | His | His | Asp | Ile | Val | Lys | Tyr | Leu | Leu | Gln | |
| | | | 245 | | | | | 250 | | | | | 255 | | | |

| agt | gat | ttg | gaa | gtt | caa | cct | cat | gtt | gtt | aat | atc | tat | gga | gat | acc | 816 |
|---|---|---|---|---|---|---|---|---|---|---|---|---|---|---|---|---|
| Ser | Asp | Leu | Glu | Val | Gln | Pro | His | Val | Val | Asn | Ile | Tyr | Gly | Asp | Thr | |
| | | 260 | | | | | 265 | | | | | 270 | | | | |

| ccc | tta | cac | ctg | gca | tgc | tac | aat | ggc | aaa | ttt | gaa | gtt | gcc | aag | gaa | 864 |
|---|---|---|---|---|---|---|---|---|---|---|---|---|---|---|---|---|
| Pro | Leu | His | Leu | Ala | Cys | Tyr | Asn | Gly | Lys | Phe | Glu | Val | Ala | Lys | Glu | |
| | | 275 | | | | | 280 | | | | | 285 | | | | |

| atc | atc | caa | ata | tca | gga | aca | gaa | agt | ctg | act | aag | gaa | aac | atc | ttc | 912 |
|---|---|---|---|---|---|---|---|---|---|---|---|---|---|---|---|---|
| Ile | Ile | Gln | Ile | Ser | Gly | Thr | Glu | Ser | Leu | Thr | Lys | Glu | Asn | Ile | Phe | |
| | | 290 | | | | | 295 | | | | | 300 | | | | |

| agt | gaa | aca | gct | ttt | cat | agt | gct | tgt | acc | tat | ggc | aag | agc | att | gac | 960 |
|---|---|---|---|---|---|---|---|---|---|---|---|---|---|---|---|---|
| Ser | Glu | Thr | Ala | Phe | His | Ser | Ala | Cys | Thr | Tyr | Gly | Lys | Ser | Ile | Asp | |
| 305 | | | | | 310 | | | | | 315 | | | | | 320 | |

| cta | gtc | aaa | ttt | ctt | ctt | gat | cag | aat | gtc | ata | aac | atc | aac | cac | caa | 1008 |

```
                Leu Val Lys Phe Leu Leu Asp Gln Asn Val Ile Asn Ile Asn His Gln
                                325                 330                 335 gga agg gat ggg cac act gga tta cac tct gct tgc tac cac ggt cac        1056
Gly Arg Asp Gly His Thr Gly Leu His Ser Ala Cys Tyr His Gly His
                340                 345                 350 att cgc ctg gtt cag ttc tta ctg gat aat gga gct gat atg aat cta        1104
Ile Arg Leu Val Gln Phe Leu Leu Asp Asn Gly Ala Asp Met Asn Leu
                355                 360                 365 gtg gct tgt gat ccc agc agg tct agt ggt gaa aaa gat gag cag aca        1152
Val Ala Cys Asp Pro Ser Arg Ser Ser Gly Glu Lys Asp Glu Gln Thr
370                 375                 380 tgt ttg atg tgg gct tat gaa aaa ggg cat gat gcc att gtc aca    ctc     1200
Cys Leu Met Trp Ala Tyr Glu Lys Gly His Asp Ala Ile Val Thr Leu
385                 390                 395                 400 ctg aag cat tat aag aga cca caa gat gaa ttg ccc tgt aat gaa    tat     1248
Leu Lys His Tyr Lys Arg Pro Gln Asp Glu Leu Pro Cys Asn Glu Tyr
                405                 410                 415 tct cag cct gga gga gat ggc tcc tat gtg tct gtt cca tca c  cc ttg      1296
Ser Gln Pro Gly Gly Asp Gly Ser Tyr Val Ser Val Pro Ser Pro Leu
                420                 425                 430 ggg aag att aaa agc atg aca aaa gag aag gca gat att ctc c  tc cta      1344
Gly Lys Ile Lys Ser Met Thr Lys Glu Lys Ala Asp Ile Leu Leu Leu
                435                 440                 445 aga gct gga ttg cct tca cat ttc cat ctt cag ctc tca ga   a att gag     1392
Arg Ala Gly Leu Pro Ser His Phe His Leu Gln Leu Ser Glu Ile Glu
450                 455                 460 ttc cat gag att att ggc tca ggt tct ttt ggg aaa gta ta  t aaa gga      1440
Phe His Glu Ile Ile Gly Ser Gly Ser Phe Gly Lys Val Tyr Lys Gly
465                 470                 475                 480 cga tgc aga aat aaa ata gtg gct ata aaa cgt tat cga   gcc aat acc      1488
Arg Cys Arg Asn Lys Ile Val Ala Ile Lys Arg Tyr Arg Ala Asn Thr
                485                 490                 495 tac tgc tcc aag tca gat gtg gat atg ttt tgc cga gag    gtg tcc att     1536
Tyr Cys Ser Lys Ser Asp Val Asp Met Phe Cys Arg Glu Val Ser Ile
                500                 505                 510 ctc tgc cag ctc aat cat ccc tgc gta att cag ttt    gtg ggt gct tgc     1584
Leu Cys Gln Leu Asn His Pro Cys Val Ile Gln Phe Val Gly Ala Cys
                515                 520                 525 ttg aat gat ccc agc cag ttt gcc att gtc act caa    tac ata tca ggg     1632
Leu Asn Asp Pro Ser Gln Phe Ala Ile Val Thr Gln Tyr Ile Ser Gly
                530                 535                 540 ggt tct ctg ttc tcc ctc ctt cat gag cag aag a  gg att ctt gat ttg      1680
Gly Ser Leu Phe Ser Leu Leu His Glu Gln Lys Arg Ile Leu Asp Leu
545                 550                 555                 560 cag tct aaa tta att att gca gta gat gtt gcc a  aa ggc atg gag tac      1728
Gln Ser Lys Leu Ile Ile Ala Val Asp Val Ala Lys Gly Met Glu Tyr
                565                 570                 575 ctt cac aac ctg aca cag cca att ata cat cg  t gac ttg aac agt cac      1776
Leu His Asn Leu Thr Gln Pro Ile Ile His Arg Asp Leu Asn Ser His
                580                 585                 590 aat att ctt ctc tat gag gat ggg cat gct gt  g gtg gca gat ttt gga      1824
Asn Ile Leu Leu Tyr Glu Asp Gly His Ala Val Val Ala Asp Phe Gly
                595                 600                 605 gaa tca aga ttt cta cag tct ctg gat gaa    gac aac atg aca aaa caa     1872
Glu Ser Arg Phe Leu Gln Ser Leu Asp Glu Asp Asn Met Thr Lys Gln
                610                 615                 620 cct ggg aac ctc cgt tgg atg gct cct gag    gtg ttc acg cag tgc act     1920
Pro Gly Asn Leu Arg Trp Met Ala Pro Glu Val Phe Thr Gln Cys Thr
625                 630                 635                 640
```

```
cgg tac acc atc aaa gca gat gtc ttc   agc tat gct ctg tgt ctg tgg     1968
Arg Tyr Thr Ile Lys Ala Asp Val Phe   Ser Tyr Ala Leu Cys Leu Trp
                645                 650                 655 gaa att ctc act ggc gaa att cca ttc   gct cat ctc aag cca gcg gct     2016
Glu Ile Leu Thr Gly Glu Ile Pro Phe   Ala His Leu Lys Pro Ala Ala
                660                 665                 670 gcg gca gca gac atg gct tac cac c ac atc aga cct ccc att ggc tat     2064
Ala Ala Ala Asp Met Ala Tyr His His Ile Arg Pro Pro Ile Gly Tyr
            675                 680                 685 tcc att ccc aag ccc ata tca tct c tg ctg ata cga ggg tgg aac gca     2112
Ser Ile Pro Lys Pro Ile Ser Ser Leu Leu Ile Arg Gly Trp Asn Ala
            690                 695             700 tgt cct gaa gga aga ccc gaa tt  t tct gaa gtt gtc atg aag tta gaa    2160
Cys Pro Glu Gly Arg Pro Glu Phe Ser Glu Val Val Met Lys Leu Glu
705                 710                 715                 720 gag tgt ctc tgc aac att gag ct  g atg tct cct gca tca agt aac agc    2208
Glu Cys Leu Cys Asn Ile Glu Leu Met Ser Pro Ala Ser Ser Asn Ser
                725                 730                 735 agt ggg tct ctc tca cct tct    tct tct tct gat tgc ctg gtg aac cgg   2256
Ser Gly Ser Leu Ser Pro Ser Ser Ser Ser Asp Cys Leu Val Asn Arg
            740                 745                 750 gga gga cct ggc cgg agt cat    gtg gca gca tta aga agt cgt ttc gaa   2304
Gly Gly Pro Gly Arg Ser His Val Ala Ala Leu Arg Ser Arg Phe Glu
            755                 760                 765 ttg gaa tat gct cta aat    gca agg tcc tat gct gct ttg tcc caa agt   2352
Leu Glu Tyr Ala Leu Asn Ala Arg Ser Tyr Ala Ala Leu Ser Gln Ser
            770                 775             780 gct gga caa tat tcc tct    caa ggt ctg tct ttg gag gag atg aaa aga   2400
Ala Gly Gln Tyr Ser Ser Gln Gly Leu Ser Leu Glu Glu Met Lys Arg
785                 790                 795                 800 agt ctt caa tac aca c  cc att gac aaa tat ggc tat gta tcc gat ccc    2448
Ser Leu Gln Tyr Thr Pro Ile Asp Lys Tyr Gly Tyr Val Ser Asp Pro
                805                 810                 815 atg agc tca atg cat t  tt cat tct tgc cga aat agt agc agc ttt gag    2496
Met Ser Ser Met His Phe His Ser Cys Arg Asn Ser Ser Ser Phe Glu
            820                 825                 830 gac agc agc                                                            2505
Asp Ser Ser
        835

<210> SEQ ID NO: 4
<211> LENGTH: 85
<212> TYPE: PRT
<213> ORGANISM: Artificial Sequence
<220> FEATURE:
<223> OTHER INFORMATION: Xaas at postions 30 and 42-59 may be any amino
      acid
<220> FEATURE:
<223> OTHER INFORMATION: Any 13 of the Xaas at postions 42 through 59
      may be absent - indicates a range of 5-18 amino acids
<220> FEATURE:
<223> OTHER INFORMATION: Description of Artificial Sequence: consensus
      sequence

<400> SEQUENCE: 4

Leu Ile Val Gly Pro Gly Pro Phe Tyr Trp Met Gly Ser Thr Asn His
  1               5                  10                  15

Ser Gly Ala Pro Trp Leu Ile Val Cys Ala Thr Pro Asp Gly Ser Thr
             20                  25                  30

Ala Cys Leu Ile Val Met Phe Tyr Xaa Xaa Xaa Xaa Xaa Xaa Xaa Xaa
         35                  40                  45

Xaa Xaa Xaa Xaa Xaa Xaa Xaa Xaa Xaa Leu Ile Val Met Phe Tyr
     50                  55                  60
```

```
Trp Cys Ser Thr Ala Arg Ala Ile Val Pro Leu Ile Val Met Phe Ala
 65                  70                  75                  80

Gly Cys Lys Arg Lys
                 85

<210> SEQ ID NO: 5
<211> LENGTH: 46
<212> TYPE: PRT
<213> ORGANISM: Artificial Sequence
<220> FEATURE:
<223> OTHER INFORMATION: Xaas at positions 8,11,20 and 21 may be any
      amino acid
<220> FEATURE:
<223> OTHER INFORMATION: Description of Artificial Sequence: consensus
      sequence

<400> SEQUENCE: 5

Leu Ile Val Met Phe Tyr Cys Xaa His Tyr Xaa Asp Leu Ile Val Met
  1               5                  10                  15

Phe Tyr Lys Xaa Xaa Asn Leu Ile Val Met Phe Tyr Cys Thr Leu Ile
                 20                  25                  30

Val Met Phe Tyr Cys Thr Leu Ile Val Met Phe Tyr Cys Thr
             35                  40                  45

<210> SEQ ID NO: 6
<211> LENGTH: 47
<212> TYPE: PRT
<213> ORGANISM: Artificial Sequence
<220> FEATURE:
<223> OTHER INFORMATION: Xaas at positions 3,11,24 and 25 may be any
      amino acid
<220> FEATURE:
<223> OTHER INFORMATION: Description of Artificial Sequence: consensus
      sequence

<400> SEQUENCE: 6

Leu Ile Val Met Phe Tyr Cys Xaa His Tyr Xaa Asp Leu Ile Val Met
  1               5                  10                  15

Phe Tyr Arg Ser Thr Ala Cys Xaa Xaa Asn Leu Ile Val Met Phe Tyr
                 20                  25                  30

Cys Leu Ile Val Met Phe Tyr Cys Leu Ile Val Met Phe Tyr Cys
             35                  40                  45
```